United States Patent
Eshetu et al.

(10) Patent No.: US 9,291,436 B2
(45) Date of Patent: Mar. 22, 2016

(54) INERT IED TRAINING KITS

(71) Applicant: DSA DETECTION LLC, North Andover, MA (US)

(72) Inventors: Abiy Eshetu, Arlington, MA (US); Timothy B. Burton, Danville, NH (US); John D. Howell, Waynesville, NC (US); Mathew F. Rutter, Boston, MA (US); Timothy James Winnett, Derry, NH (US)

(73) Assignee: DSA DETECTION LLC, North Andover, MA (US)

( * ) Notice: Subject to any disclaimer, the term of this patent is extended or adjusted under 35 U.S.C. 154(b) by 0 days.

(21) Appl. No.: 14/334,997

(22) Filed: Jul. 18, 2014

(65) Prior Publication Data

US 2015/0268016 A1 Sep. 24, 2015

Related U.S. Application Data

(60) Provisional application No. 61/931,456, filed on Jan. 24, 2014, provisional application No. 61/857,531, filed on Jul. 23, 2013.

(51) Int. Cl.

| | |
|---|---|
| *F42B 8/00* | (2006.01) |
| *F42B 4/18* | (2006.01) |
| *F42B 99/00* | (2006.01) |
| *C06B 23/00* | (2006.01) |
| *G01N 33/22* | (2006.01) |

(52) U.S. Cl.
CPC . *F42B 8/00* (2013.01); *C06B 23/00* (2013.01); *F42B 4/18* (2013.01); *F42B 99/00* (2013.01); *G01N 33/22* (2013.01)

(58) Field of Classification Search
CPC .... C06B 23/00; C06B 23/001; C06B 23/002; C06B 23/009; F41H 11/136; G01N 23/00; G01N 23/02; G01N 23/06; G01N 23/08; G01N 23/083; G01N 23/20; G01N 24/00; G01N 24/084; G01N 33/22; G01N 33/227; F42B 1/00; F42B 3/00; F42B 4/18; F42B 8/00; F42B 99/00
USPC .................................................. 102/355, 293
See application file for complete search history.

(56) References Cited

U.S. PATENT DOCUMENTS

| | | | |
|---|---|---|---|
| 3,457,329 A | | 7/1969 | Silver et al. |
| 5,182,764 A | | 1/1993 | Peschmann et al. |
| 5,319,547 A | | 6/1994 | Krug et al. |
| 5,359,936 A | | 11/1994 | Simpson et al. |
| 5,413,812 A | | 5/1995 | Simpson et al. |
| 5,648,636 A | | 7/1997 | Simpson et al. |
| 5,756,006 A | | 5/1998 | Reed, Jr. et al. |
| 5,958,299 A | | 9/1999 | Kury et al. |
| 7,694,628 B2 * | 4/2010 | Adebimpe | A01K 15/02 102/293 |
| 7,854,811 B1 * | 12/2010 | Wartman | C06B 21/0025 149/105 |
| 7,932,089 B2 * | 4/2011 | Cohen-Arazi | A01K 15/02 102/355 |

(Continued)

FOREIGN PATENT DOCUMENTS

RU   WO 2011043702 A3 *  6/2011  .............. C06B 23/00

*Primary Examiner* — James S Bergin
(74) *Attorney, Agent, or Firm* — Lando & Anastasi, LLP

(57) ABSTRACT

Disclosed herein are embodiments of simulated explosive materials and Threat Screening Kits and simulated IED Circuit Kits including simulated explosive materials. The simulated explosive materials are configured to produce an output signal consistent with the presence of an actual explosive material when scanned in an X-ray scanner.

30 Claims, 67 Drawing Sheets

(56) References Cited

U.S. PATENT DOCUMENTS

| | | | |
|---|---|---|---|
| 8,114,230 B1 * | 2/2012 | Basom | C06B 23/00 149/109.4 |
| 8,172,967 B1 * | 5/2012 | Wartman | C06B 21/0025 149/109.6 |
| 8,173,430 B2 * | 5/2012 | Cohen-Arazi | A01K 15/02 102/355 |
| 8,444,881 B2 * | 5/2013 | Adebimpe | A01K 15/02 252/408.1 |
| 8,563,316 B2 | 10/2013 | Duffy et al. | |
| 8,641,843 B2 * | 2/2014 | Hagit | A01K 15/02 149/108.8 |
| 8,857,340 B2 * | 10/2014 | Hagit et al. | 102/355 |
| 2007/0281358 A1 | 12/2007 | Cohen-Arazi et al. | |
| 2009/0194744 A1 | 8/2009 | Adebimpe | |

* cited by examiner

INERT

NITRO-DYNAMITE

60/40 8.5 oz.

HIGH EXPLOSIVES

CLASS A 1.1 EXPLOSIVES

INERT

INERT SIMULANT INERT SIMULANT INERT SIMULANT INERT SIMULANT

INERT SIMULANT INERT SIMULANT INERT SIMULANT INERT SIMULANT

EXPLOSIVE PLASTIC SEMTEX-H

INERT SIMULANT INERT SIMULANT INERT SIMULANT

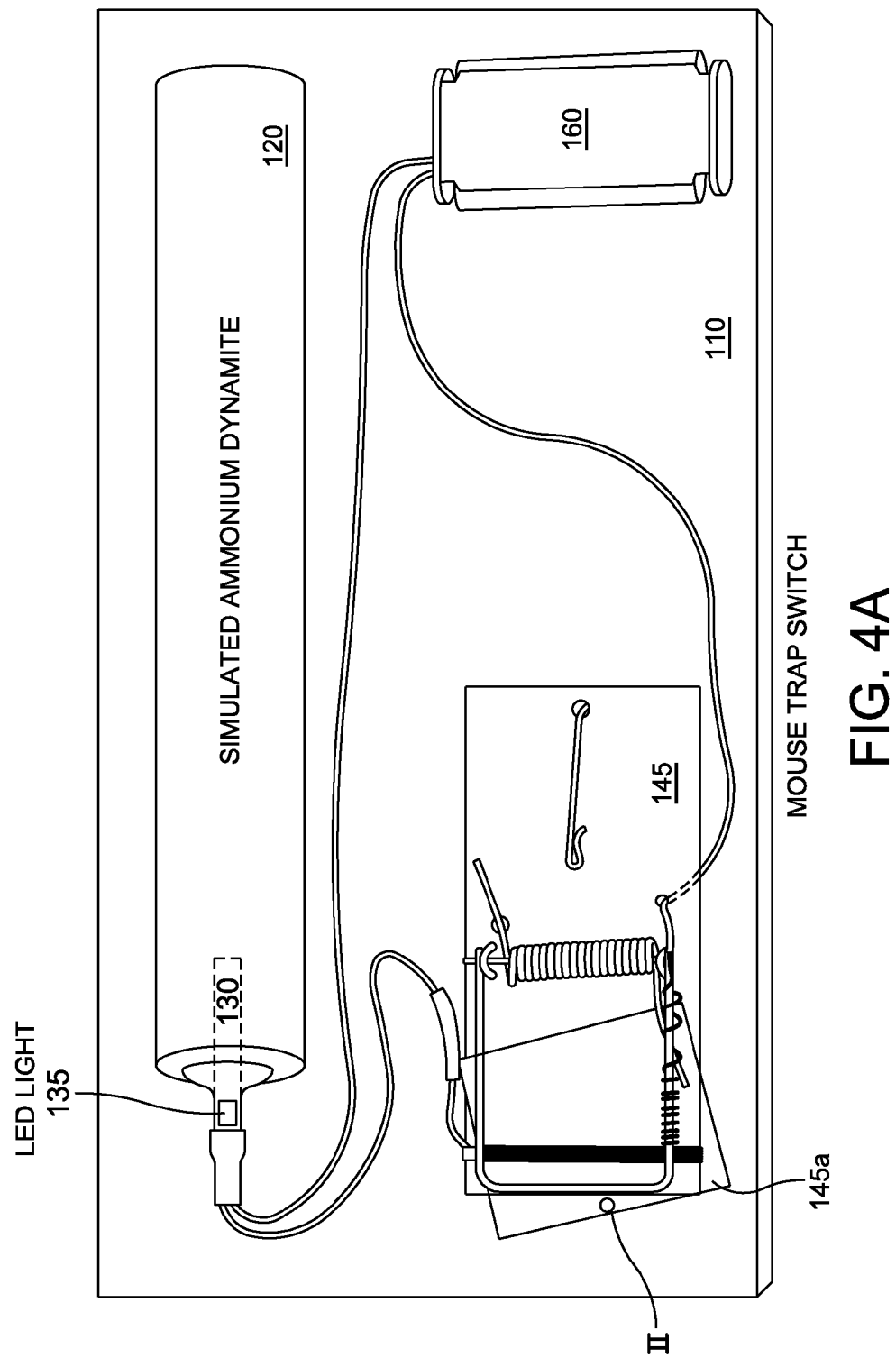

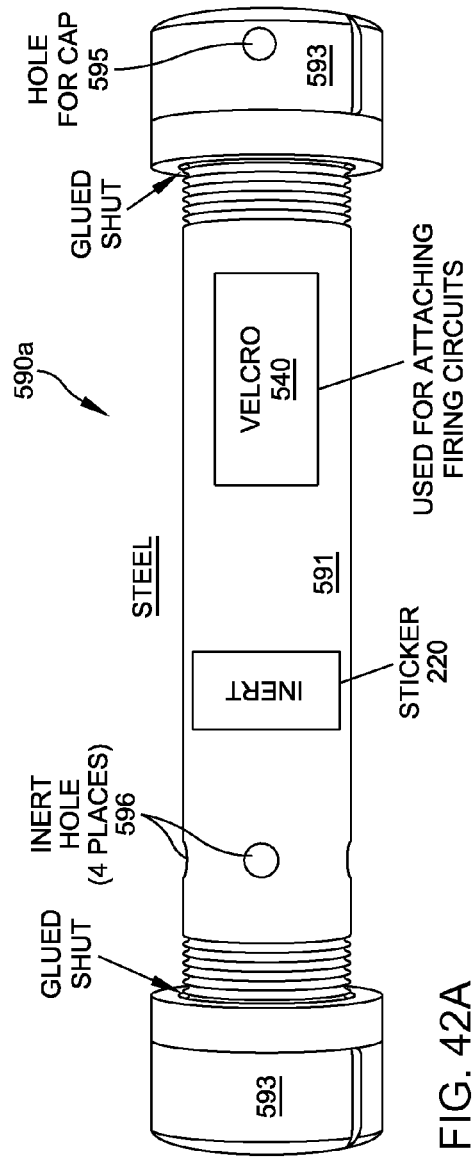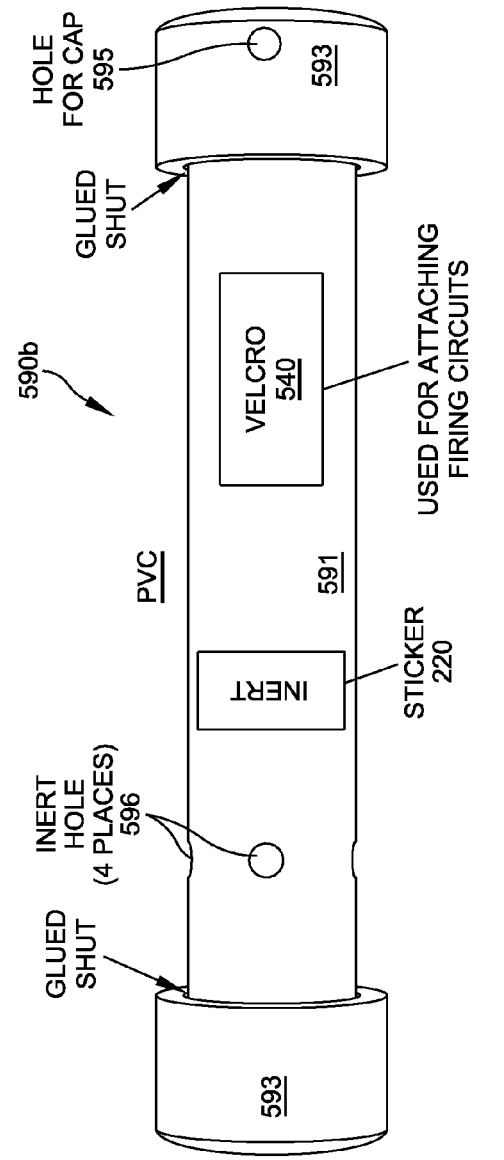
FIG. 42A
FIG. 42B
THREAT SCREEN KIT
PIPE BOMBS

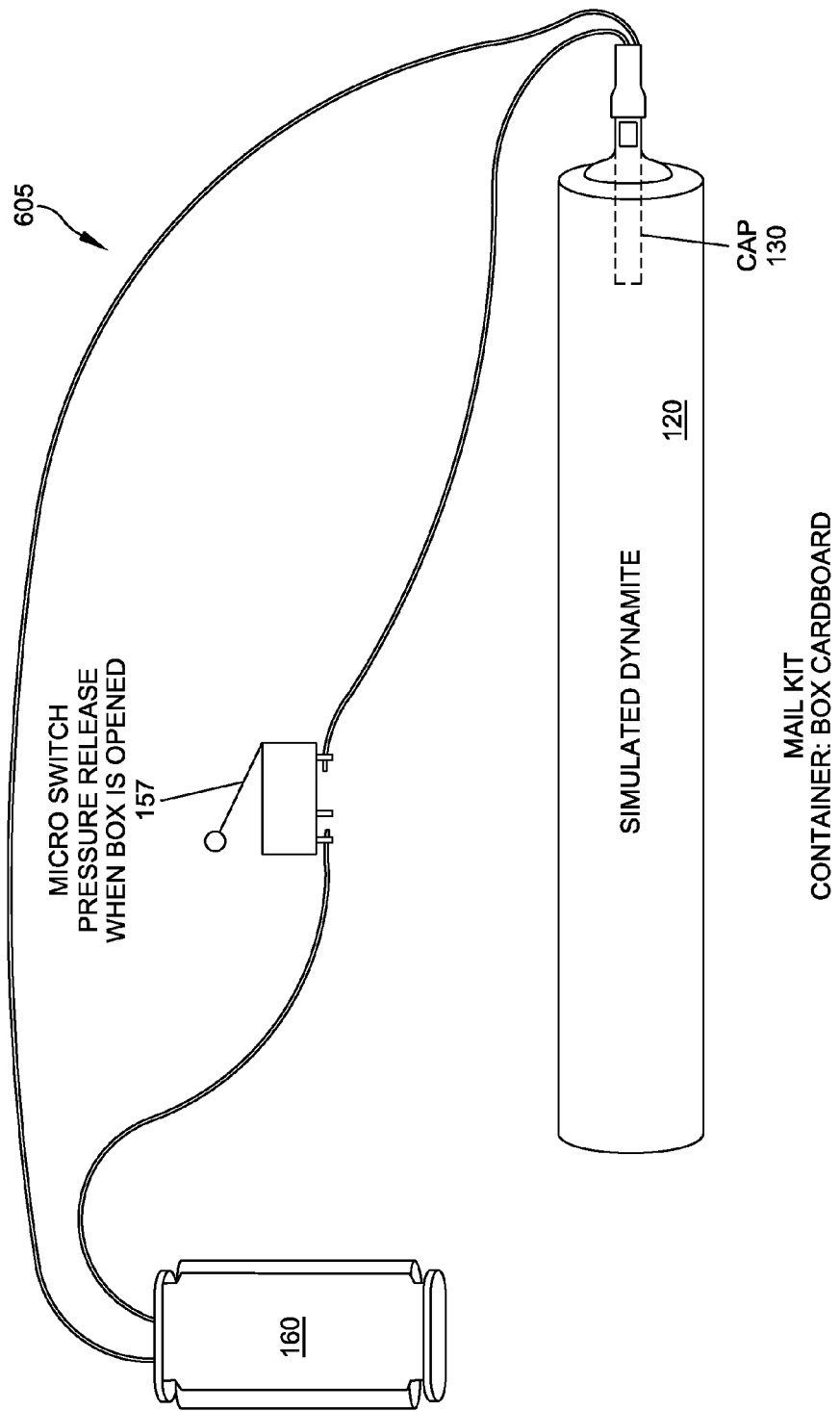

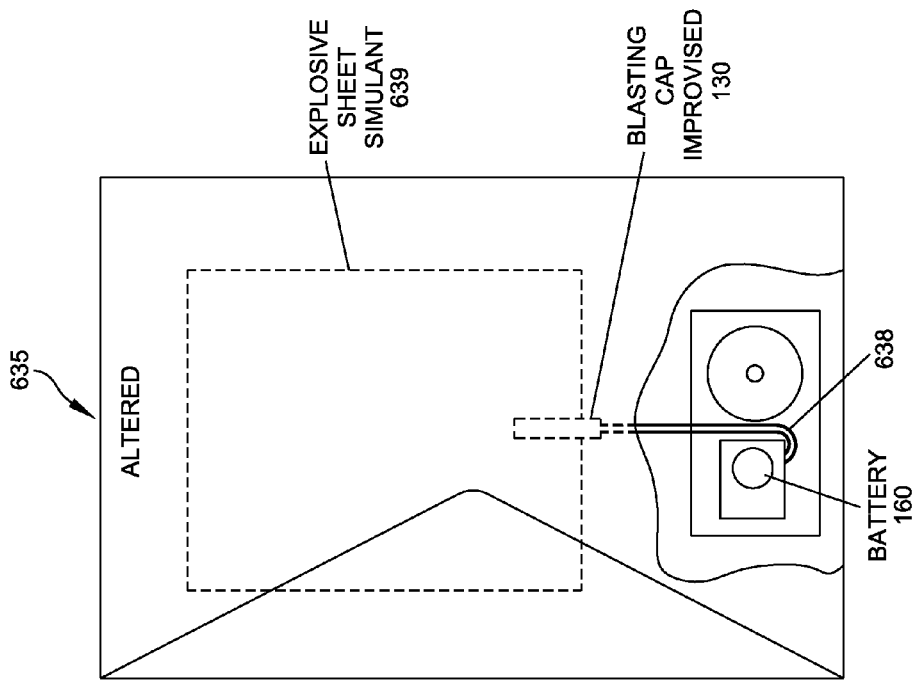
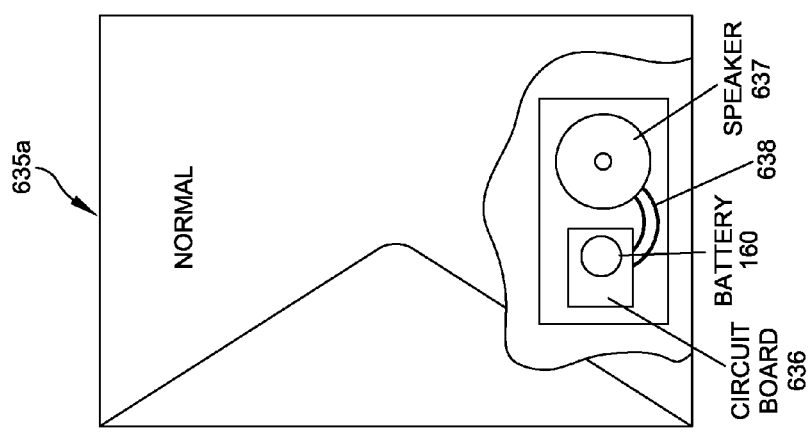
MAIL KIT
MUSICAL GREETING CARD
FIG. 49B
FIG. 49A

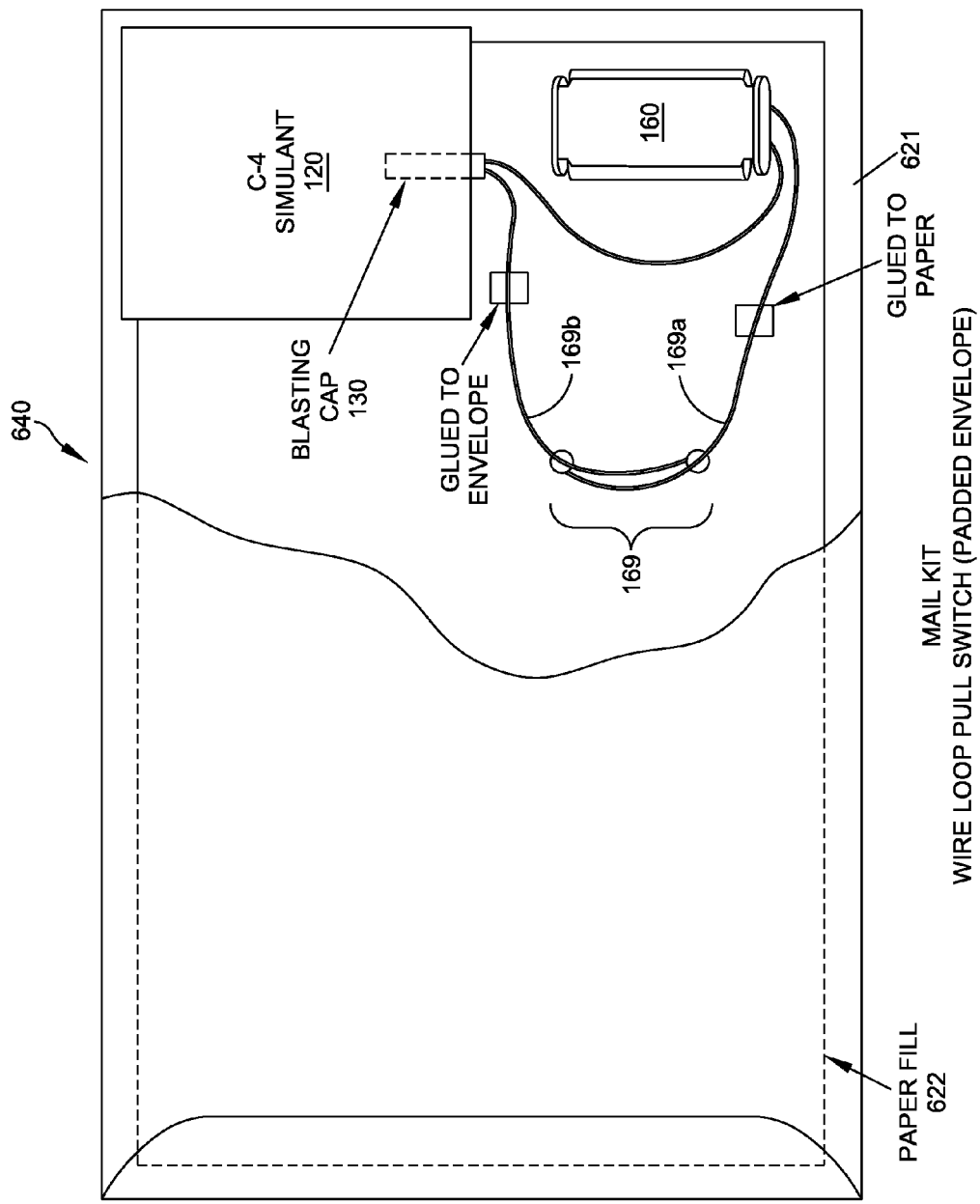

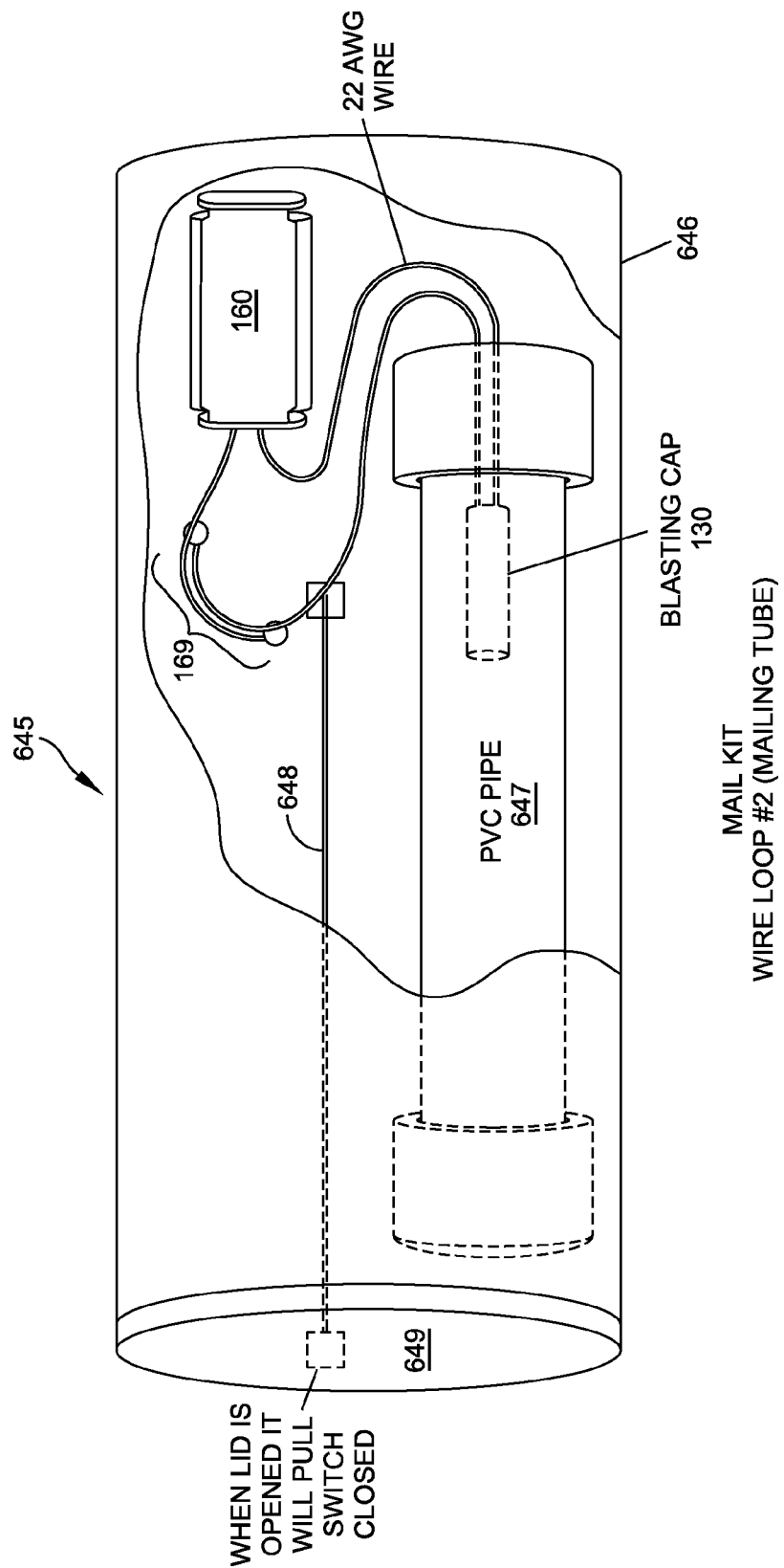

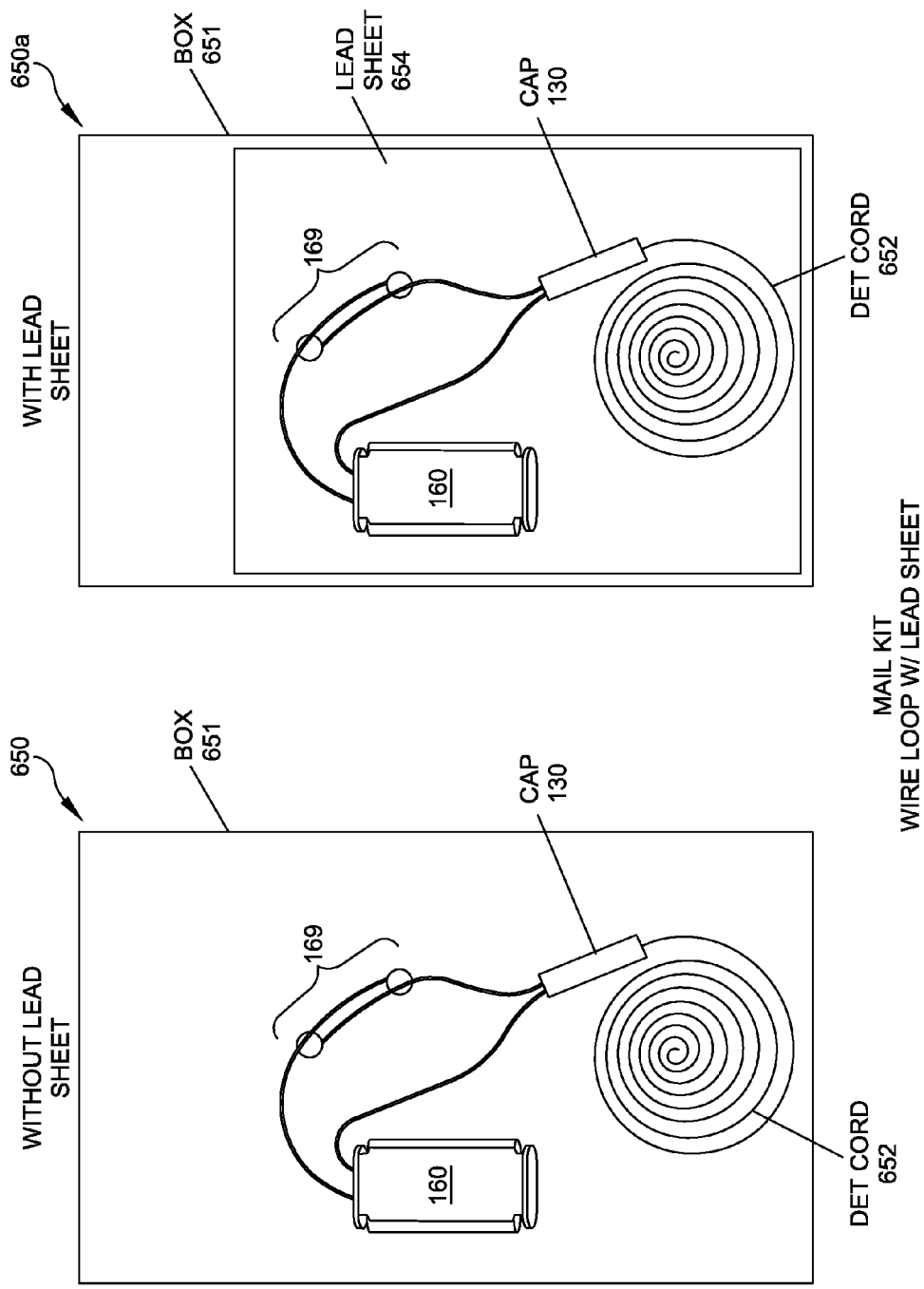

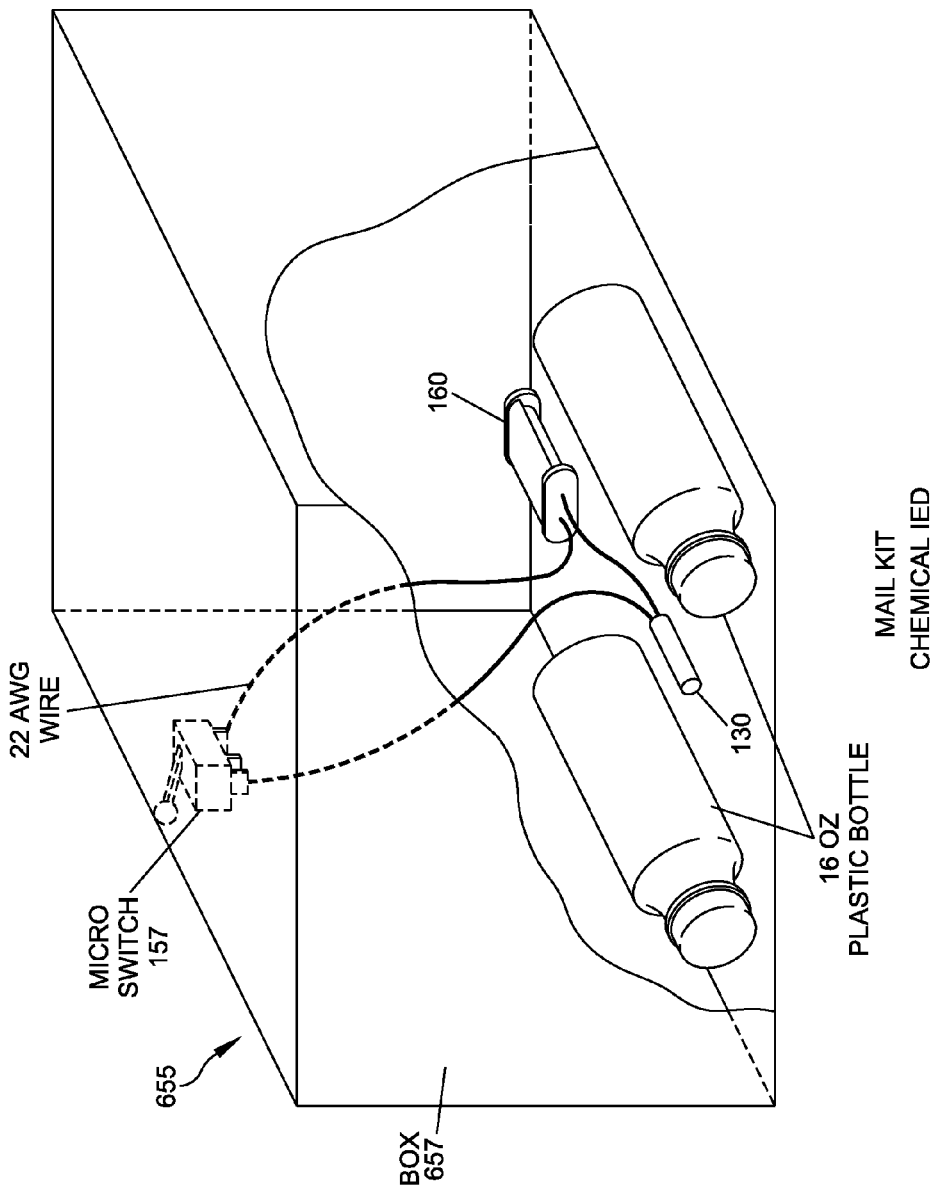

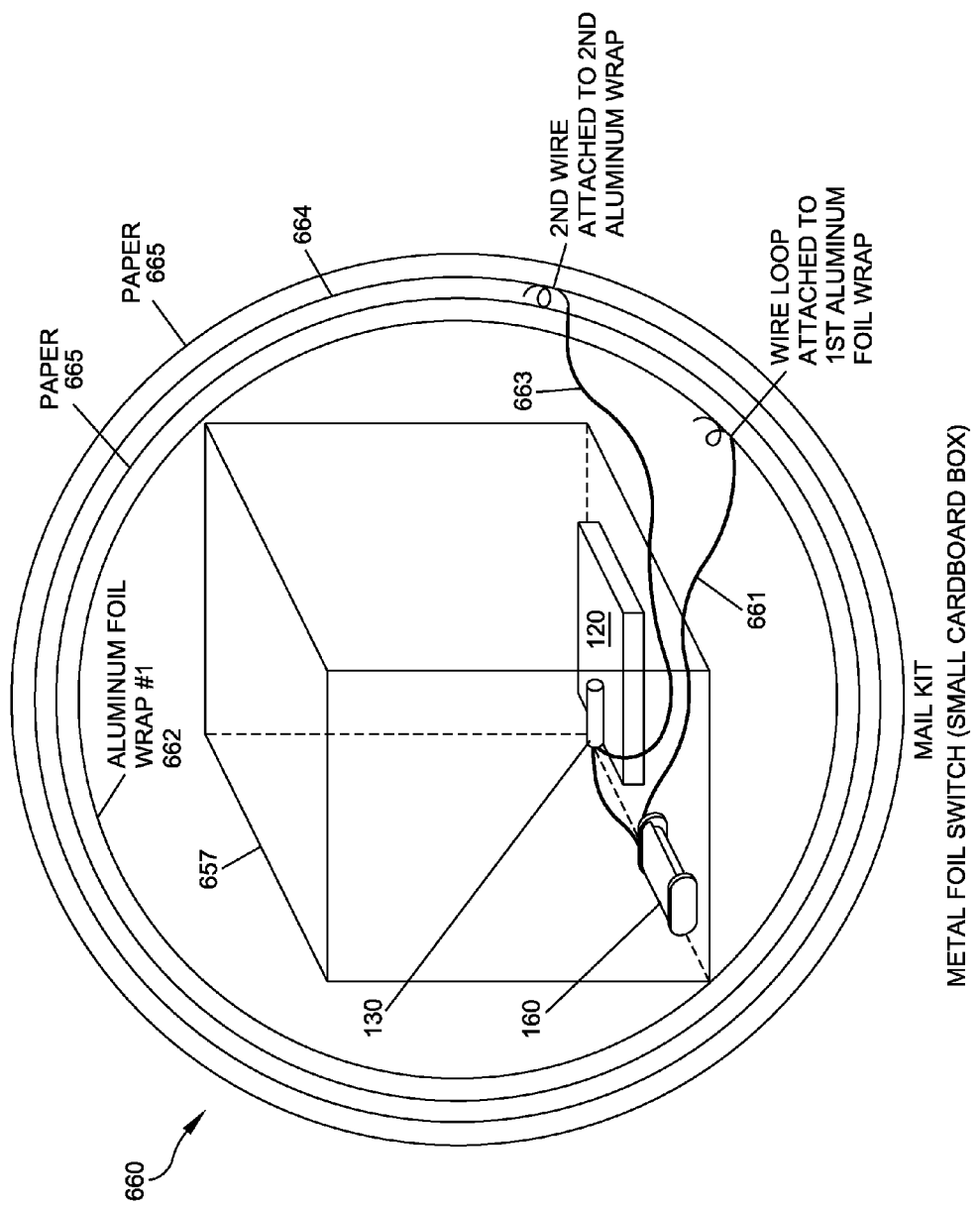

INERT IED TRAINING KITS

RELATED APPLICATIONS

This application claims priority under 35 U.S.C. §119(e) to U.S. Provisional Application Ser. No. 61/931,456, titled "INERT IED TRAINING KITS," filed on Jan. 24, 2014, and to U.S. Provisional Application Ser. No. 61/857,531, titled "INERT IED TRAINING KITS," filed on Jul. 23, 2013, each of which is herein incorporated by reference in its entirety.

BACKGROUND

1. Technical Field

Aspects and embodiments of the present invention are generally directed to inert materials and apparatus which simulate the look, feel, and/or X-ray response of explosive materials or devices such as improvised explosive devices (IEDs) or other potentially harmful devices. The inert materials and apparatus may be utilized for training of persons to identify actual harmful devices or testing X-ray devices and other instruments.

2. Discussion of Related Art

In numerous locations, most notably airports and other transportation hubs, packages, for example, passenger luggage may be screened for the presence of explosives, improvised explosive devices, or other potentially harmful devices. The screening process is often accomplished by the use of X-ray scanners. X-ray scanners may identify explosive materials by the density of the material and/or the effective atomic number ($Z_{eff}$).

The two mechanisms primarily responsible for X-Ray attenuation at the energy levels typically utilized by explosive detection equipment are photoelectric absorption and Compton scattering. The photoelectric effect attenuates X-Ray transmission by absorption of incident X-Ray photons and resultant emission of a photoelectron and corresponding X-Ray. Compton scattering attenuates X-Ray transmission by inelastic scattering of incident X-Ray photons, resulting in a recoil electron and an emitted photon with lower energy. The attenuation of transmitted X-Rays is dominated by the photoelectric effect for elements with high atomic numbers whereas the attenuation by Compton scattering is dominant for elements with lower atomic numbers.

Compared to the photoelectric effect, the attenuation due to Compton scattering is relatively invariant with respect to incident X-Ray energy. Thus, detectors utilizing multi-energy X-Rays can distinguish materials of different atomic numbers based on the relative contributions of Compton scattering and photoelectric absorption on the overall absorption. Additional information about the density of the material may be inferred from the absorption of the high energy photons. In contrast with lower energy X-Rays, the absorption of high energy X-Rays are primarily due to Compton scattering which is roughly proportional to mass per cross sectional area. Algorithms may be put in place to automatically discriminate between materials which share characteristics (effective atomic number and density) with explosive materials and those that do not, thereby aiding in the detection. These X-ray scanners may sound an alarm or otherwise provide an indication of the suspected explosive material so that a trained agent may make a further investigation and respond accordingly. The X-ray scanners may identify different suspected explosive materials by different colors on a display.

SUMMARY

In accordance with an aspect of the present disclosure, there is provided a simulated explosive material. The simulated explosive material comprises or consists of one or more inert components that has a density and effective atomic number ($Z_{eff}$) substantially similar to an explosive material. The simulated explosive material is configured to produce an output signal consistent with the presence of the explosive material when scanned in an X-ray scanner.

In some embodiments, the one or more inert components include brown sugar.

In some embodiments, the one or more inert components include a mixture of brown sugar and one or more of corn syrup, baking soda, water, or oil. The simulated explosive material may be configured to produce an output signal consistent with the presence of dynamite when scanned in an X-ray scanner.

In some embodiments, the one or more inert components include a mixture of confectioner sugar and one or more of corn starch or corn syrup. The simulated explosive material may be configured to produce an output signal consistent with the presence of one of dynamite or PE-4 when scanned in an X-ray scanner.

In some embodiments, the one or more inert components include a mixture of baking soda and one or more of corn syrup, corn starch, water, oil, or paraffin wax. The simulated explosive material may be configured to produce an output signal consistent with the presence of one of Semtex, C-4, TNT, or a plastic explosive when scanned in an X-ray scanner.

In some embodiments, the one or more inert components include a mixture of corn starch, baking soda, water, and oil. The simulated explosive material may be configured to produce an output signal consistent with the presence of a plastic explosive when scanned in an X-ray scanner.

The simulated explosive material may be configured to produce an output signal consistent with the presence of one of PE-4, TNT, nitroglycerine, or C-4 when scanned in an X-ray scanner.

In some embodiments, the one or more inert components include cane sugar.

In some embodiments, the one or more inert components include one of black sand or charcoal.

In some embodiments, the one or more inert components include a mixture of polymeric materials of varying molecular weights. These materials may include but are not limited to polyethylene, polytetrafluoroethylene, polydimethylsiloxane, polyvinylchloride and, polyvinyl acetate. The simulated explosive material may be configured to produce an output signal consistent with the presence of a variety of explosives when scanned in an X-Ray scanner.

In some embodiments, the one or more inert components include a mixture of glycerin, corn starch, alumina, hydrogen peroxide. In some embodiments, the one or more inert components further includes a colorant, for example food coloring or paint. In some embodiments, the one or more inert components include a mixture of water, charcoal, sodium chloride (NaCl) and calcium chloride ($CaCl_2$).

In some embodiments, the one or more inert components include a mixture of oxides and/or nitrides. These materials may include but are not limited to Boron Oxide, Aluminum Oxide, Silicon Oxide, aluminosilicates, Boron Nitride, Carbon Nitride, and/or other organic or inorganic ceramic materials. The simulated explosive material may be configured to produce an output signal consistent with the presence of a variety of explosives when scanned in an X-Ray scanner.

In accordance with another aspect of the present disclosure, there is provided a simulated IED Circuit Kit. The simulated IED circuit Kit comprises an explosive simulant comprising or consisting of one or more inert components and having a density and/or $Z_{eff}$ substantially similar to an explosive material, a simulated blasting cap adjacent to the explosive simulant, a trigger switch, and a power source.

In some embodiments, the trigger switch includes one or more of a mousetrap switch, a clothespin switch, a wireless doorbell receiver, a vibration switch, a reed switch, a dummy cell phone, a two-way radio, a cordless telephone, a passive infrared receiver, a pair of saw blades, a pressure activated micro switch, a tilt switch, a mercury switch, a digital clock, a mechanical clock, a kitchen timer, a servo motor, a temperature switch, a photo cell, or a wire loop switch.

In some embodiments, the explosive simulant includes one of a mixture of brown sugar and one or more of corn syrup, baking soda, water, and oil, a mixture of baking soda and one or more of corn syrup, corn starch, water, oil, and paraffin wax, a mixture of confectioner sugar and one or more of corn starch and corn syrup, a mixture of glycerin, corn starch, alumina, and hydrogen peroxide, a mixture of corn starch, baking soda, water, and oil, and a mixture corn starch, water, and oil.

In some embodiments, the explosive simulant includes one of brown sugar and cane sugar.

In some embodiments, the explosive simulant includes one of black sand or charcoal.

In some embodiments, the simulated IED Circuit Kit further comprises an arming switch in electrical communication between the power source and the simulated blasting cap.

In accordance with another aspect of the present disclosure, there is provided a simulated blasting cap. The simulated blasting cap comprises a tube and an explosive simulant disposed within the tube. The explosive simulant comprises or consists of one or more inert components having a density and/or $Z_{\mathit{eff}}$ substantially similar to an explosive material. The simulated blasting cap further comprises a bridge wire disposed within the tube.

In some embodiments, the explosive simulant may include a wooden dowel or a polymer, such as PTFE, rod.

In some embodiments, the simulated blasting cap further comprises a metal sleeve disposed within the tube.

In some embodiments, the simulated blasting cap further comprises a lead wire disposed within the tube.

In accordance with another aspect of the present disclosure, there is provided a Threat Screening Kit. The Threat Screening Kit comprises a simulated blasting cap including an explosive simulant, a power source, and a trigger mechanism in electrical communication between the simulated blasting cap and the power source.

In some embodiments, the simulated blasting cap includes a metal sleeve disposed within a tube.

In some embodiments, the simulated blasting cap includes a lead wire disposed within a tube.

In some embodiments, the trigger mechanism includes one or more of a mousetrap switch, a clothespin switch, a wireless doorbell receiver, a vibration switch, a reed switch, a cell phone dummy, a two-way radio, a cordless telephone, a passive infrared receiver, a pair of saw blades, a pressure activated micro switch, a tilt switch, a mercury switch, a digital clock, a mechanical clock, a kitchen timer, a servo motor, a temperature switch, a photo cell, and a wire loop switch.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3A illustrates an embodiment of a label for a package including an explosive simulant;

FIG. 3C illustrates an embodiment of a label for a package including an explosive simulant;

FIG. 4A illustrates an embodiment of a simulated IED Circuit Kit;

FIG. 42A illustrates an embodiment of a Threat Screening Kit;
FIG. 42B illustrates an embodiment of a Threat Screening Kit;
FIG. 43 illustrates an embodiment of a Mail Threat Kit;
FIG. 49A illustrates an embodiment of a Mail Threat Kit;
FIG. 49B illustrates an embodiment of a Mail Threat Kit;
FIG. 50 illustrates an embodiment of a Mail Threat Kit;
FIG. 51 illustrates an embodiment of a Mail Threat Kit;
FIG. 52A illustrates an embodiment of a Mail Threat Kit;
FIG. 52B illustrates an embodiment of a Mail Threat Kit;
FIG. 53 illustrates an embodiment of a Mail Threat Kit;
FIG. 54 illustrates an embodiment of a Mail Threat Kit.

DETAILED DESCRIPTION

Figure 1:
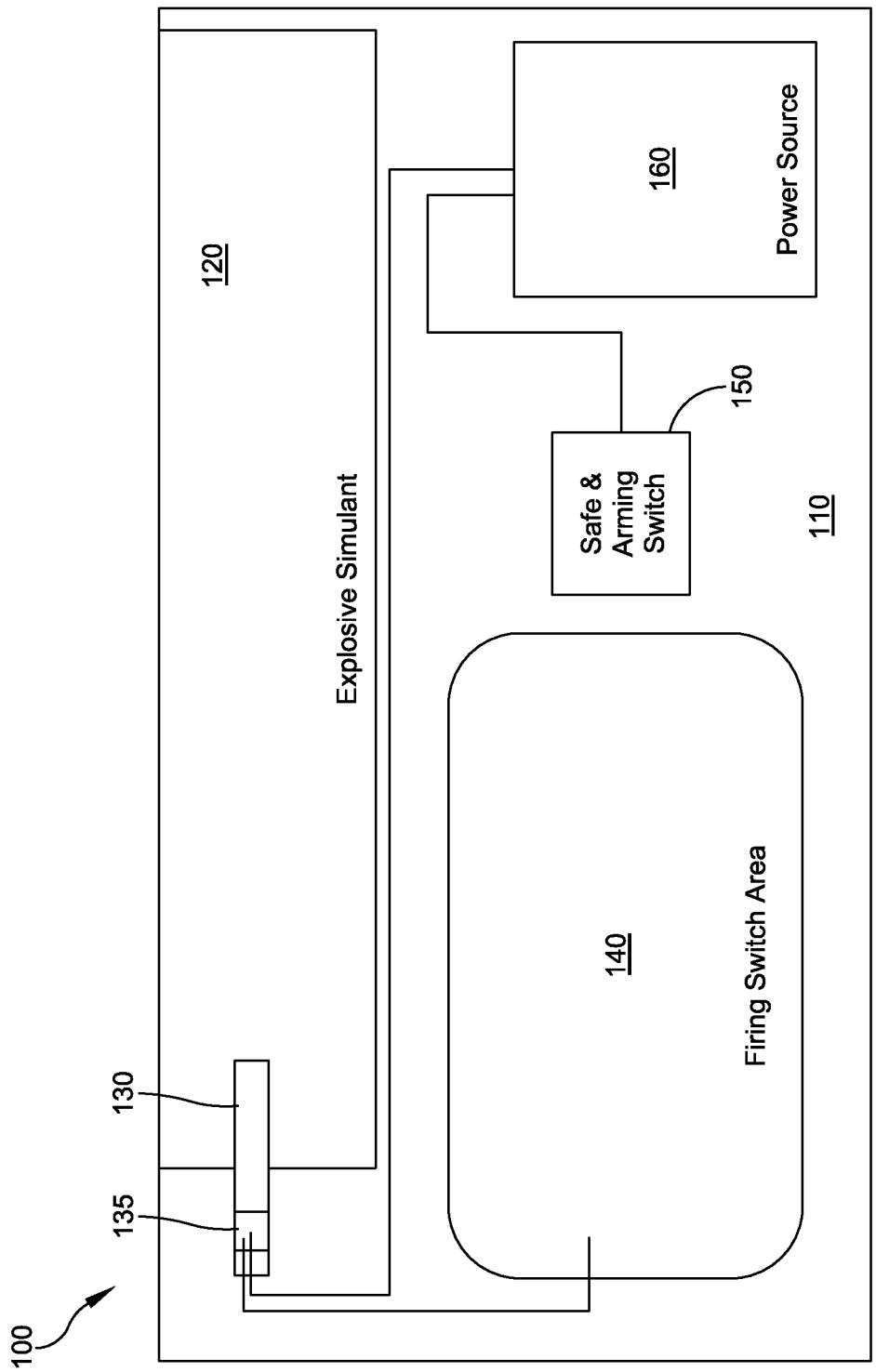
FIG. 1 illustrates the components of an embodiment of a simulated IED Circuit Kit.

Aspects and embodiments of the present invention are not limited to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," "having," "containing," "involving," and variations thereof herein is meant to encompass the items listed thereafter and equivalents thereof.

It has been discovered that many explosive materials may be simulated by one or more non-explosive and inert materials or mixtures thereof, which in some instances may be sufficiently harmless to not require a material safety data sheet (MSDS) when provided by a supplier to a customer. These inert material mixtures may have densities and/or $Z_{eff}$ sufficiently close to the explosive material which they simulate so that an X-ray scanner may produce an output signal consistent with the presence of the simulated explosive material when scanning the inert material. Many X-ray scanners provide a standardized set of colors categorizing materials of different effective atomic numbers. The inert materials may be designed to cause an X-ray scanner to classify the inert material mixtures with the same colors as the explosive materials which they are intended to simulate. The inert material mixtures may also be used to simulate explosive materials in other forms of scanners, for example, backscattering or computed tomography scanner systems. These inert material mixtures may also be colored, for example, by the addition of food coloring, and textured in a similar manner as the explosive material which they are intended to simulate. Examples of various inert materials and material mixtures and the explosive materials which they may simulate are listed in Table 1 below:

TABLE 1

| Explosive name | Abbreviation | $Z_{eff}$ | Density (g/cm³) | Simulant Material(s) |
|---|---|---|---|---|
| ANFO | ANFO | ~7 | 0.8 | Low grade Ammonium Nitrate (AN) with Polydimethylsiloxane PDMS and food coloring |
| Hexamethylene triperoxide diamine | HMTD | 7.0 | 0.88 | HMTD Simulant |
| Amonium Nitrate | AN | 7.4 | 0.9 | Low grade AN |
| Ammonium Nitrate Nitroglycerin Dynamite | Dynamite | | 1.02 | Dark Brown Sugar |
| Kinestick | Binary | | 1.1 | |
| Nitromethene | NM | 7.4 | 1.13 | Sugar, Salt and Water |

TABLE 1-continued

| Explosive name | Abbreviation | $Z_{eff}$ | Density (g/cm³) | Simulant Material(s) |
|---|---|---|---|---|
| Sensitized Nitromethane (95% Nitromethane, 5% EDA) | PLX | 7.3 | 1.13 | PLX Simulant |
| Hydrogen Peroxide (30%) | | 7.6 | 1.13 | Hydrogen Peroxide Simulant |
| Methyl Ethyl Ketone Peroxide | MEKP | 6.7 | 1.17 | Sugar, Salt and Water |
| Acetone Peroxide | AP or TATP | 6.7 | 1.18 | TAPT simulant |
| Nitrocellulose | NC | 7.1 | 1.2 | |
| Apcogel B-1 ® (Semi-Gel) | Dynamite | | 1.26 | Dark Brown Sugar |
| Extra Gelatin Nitroglycerin Dynamite | Dynamite | | 1.3 | |
| Semtex 1A | SEMTEX | 7.1 | 1.42 | Baking Soda, Corn Starch, Paraffin Wax, Water, and Vegetable Oil or Corn Starch, Baking Soda, Basic initiator, and glycerin |
| Semtex 1H | SEMTEX | 7.4 | 1.43 | |
| Semtex 10 | SEMTEX | 7.3 | 1.43 | |
| 60% Extra Gelatin | Dynamite | | 1.43 | |
| Detasheet | | 7.0 | 1.41 | Acrylic polymer blend of various Acrylate monomers and Baking Soda |
| Primasheet 1000 | | 7.1 | 1.44 | |
| FLEX X M118 | | 7.1 | 1.44 | |
| Nitroglycol | EGDN | 7.4 | 1.48 | Sugar, Salt and Water |
| PE-4 | PE-4 | 7.4 | 1.5 | Baking Soda, Corn Starch, Wax, Water, and Oil or Corn Starch, Baking Soda, Basic initiator and glycerin |
| Ethyl picrate | | 7.0 | 1.55 | Baking Soda, Corn Starch, Wax, Water, and Oil |
| TNT/RDX Booster | Booster | | 1.56 | |
| Methyl picrate | | 7.1 | 1.57 | Polyethylene, Baking Soda, Powder detergent and Glycerin |
| Urea nitrate | UN | 7.3 | 1.59 | Polyethylene, Baking Soda, Powder detergent and Glycerin |
| Nitroglycerine | NG | 7.4 | 1.59 | Sugar, Salt and Water |
| 1,3,5-Trinitrobenzene | TNB | 7.1 | 1.6 | Sugar, Salt and Water or Polyethylene, Baking Soda, Powder detergent and Glycerin, depending on phase |
| Trinitrotoluene | TNT | 7.1 | 1.6 | Baking Soda, Corn Starch, Wax, Water, and Oil |
| Ammonium Picrate | Dunnite | 7.1 | 1.72 | Baking Soda, Corn Starch, Wax, Water, and Oil |
| Erythritol Tetranitrate | ETN | 7.5 | 1.6 | Polyethylene, Baking Soda, Powder detergent and Glycerin |
| Primasheet 2000 | | 7.1 | 1.62 | Acrylic polymer blend and Baking Soda |
| Trinitrocresol | | 7.1 | 1.62 | Polyethylene, Baking Soda, Powder detergent and Glycerin |
| Composition #4 C-4 | C-4 | 7.5 | 1.64 | Baking Soda, Corn Starch, Wax, Water, and Oil or Corn Starch, Baking Soda, Basic initiator (a Chemical that initiates base catalyzed polymerization,) and glycerin |
| Ethylenedinitramine | EDNA | 7.1 | 1.65 | Polyethylene, Baking Soda, Powder detergent and Glycerin |
| Picric acid | TNP | 7.2 | 1.7 | Polyethylene, Baking Soda, Powder detergent and Glycerin |
| Pentaerythritoltetranitrate | PETN | 7.4 | 1.7 | PETN Simulant |
| Nitroguanidine | NQ | 7.1 | 1.7 | Polyethylene, Baking Soda, Powder detergent and Glycerin |
| Tetryl | | 7.2 | 1.71 | Baking Soda, Corn Starch, Wax, Water, and Oil |
| 1,3,5-Triazido-2,4,6-trinitrobenzene | TATNB | 7.1 | 1.71 | Polyethylene, Baking Soda, Powder detergent and Glycerin |
| Trinitroaniline | TNA | 7.1 | 1.72 | Polyethylene, Baking Soda, Powder detergent and Glycerin |
| Comp B TNT/RDX/wax | Comp B | 7.3 | 1.72 | Baking Soda, Corn Starch, Wax, Water, and Oil or Corn Starch, Baking Soda, Basic initiator, and glycerin |
| Mannitol hexanitrate | MHN | 7.5 | 1.73 | Polyethylene, Baking Soda, Powder detergent and Glycerin |
| Picryl chloride | | 9.9 | 1.74 | Polyethylene, Baking Soda, Powder detergent and Glycerin |
| Cyclotrimethylenetrinitramine | RDX | 7.6 | 1.76 | RDX Simulant |
| Triaminotrinitrobenzene | TATB | 7.1 | 1.8 | Polyethylene, Baking Soda, Powder detergent and Glycerin |
| Cyclotetramethylene-tetranitramine | HMX | 7.2 | 1.91 | Polyethylene, Baking Soda, Powder detergent and Glycerin |
| Hexanitrohexaazaisowurtzitane | HNIW or CL-20 | 7.3 | 2.04 | Polyethylene, Baking Soda, Powder detergent and Glycerin |

TABLE 1-continued

| Explosive name | Abbreviation | $Z_{eff}$ | Density (g/cm³) | Simulant Material(s) |
|---|---|---|---|---|
| Potassium Chlorate | | 15.5 | 2.34 | Sodium and potassium chloride |
| Aluminum metal | | 13 | 2.7 | Various metal oxides |
| Lead styphnate | | 59.9 | 3.02 | Lead |
| Silver azide | | 41.1 | 4 | |
| Mercury fulminate | | 69.2 | 4.42 | |
| Lead azide | | 71.1 | 4.71 | |

Table 1 lists the densities and effective atomic numbers of various explosive materials with the corresponding abbreviations and various products using these materials. Examples of inert materials and inert material mixtures which may be used to simulate the explosive materials, for example, by closely matching their densities and/or effective atomic numbers ($Z_{eff}$) are listed in the rightmost column. In some embodiments, butylated hydroxytoluene (BHT) may be included as an additional ingredient in one or more of the formulations listed above. The BHT may function as a preservative for the materials included in one or more of the formulations listed above. Further, coloring agents, for example, food coloring, may be added to various of the formulations listed above so that the inert materials and/or inert material mixtures may closely match both the look and feel of an explosive material which they are intended to mimic.

$Z_{eff}$ may be calculated according to the formula $$Z_{eff} = \sum_i (\alpha_i \cdot Z_i^{n-1})^{\frac{1}{n-1}}$$

where $Z_i$ is the atomic number of element i, $\alpha_i$ is the fraction of the total electrons contained by element i and n is a weighting factor equal to, for example, 3.9. Some references may utilize slightly different values of n when calculating $Z_{eff}$ for a material or may use a different formula.

Examples

A number of simulant mixtures may be prepared. These mixtures may be packaged in cardboard tubes, plastic tubes, vacuum sealed plastic film, or other packages. The densities of the simulant mixtures were measured and types of explosive for which the simulant mixtures would be useful in simulating were identified.

Mix 1A:
Dark brown sugar (e.g. Domino™ Dark Brown Sugar)
Density of mixture: 1.0 g/cc
This mixture is useful for the "El Blasto" dynamite simulant.

Mix 1B:
Dark brown sugar (e.g. Domino™ Dark Brown Sugar): 900 g
Corn Syrup (e.g. Karo™ Red Label 16 oz. Light Syrup): 50 g
Density of mixture: 1.1 g/cc
This mixture is useful for the "Ammonium Dynamite" simulant.

Mix 1C:
Dark brown sugar (e.g. Domino™ Dark Brown Sugar): 900 g
Corn Syrup (e.g. Karo™ Red Label 16 oz. Light Syrup): 100 g
Density of mixture: 1.2 g/cc
This mixture is useful for the "Nitro Dynamite" simulant.

Mix 2:
Dark brown sugar (e.g. Domino™ Dark Brown Sugar): 900 g
Corn Syrup (e.g. Karo™ Red Label 16 oz. Light Syrup): 100 g
Baking Soda: 150 g
Density of mixture: 1.3 g/cc
This mixture is useful for the "Extra Gelatin" dynamite simulant.

Mix 3:
Confectioner sugar (e.g. Domino™ Confectioner Sugar): 2 pounds
Corn syrup (e.g. Karo™ Red Label 16 oz. Light Syrup): 1.5 cups
Density of mixture: 1.5 g/cc
Density of mixture in plastic packaging: 1.5 g/cc
This mixture is useful for the "M1 Military Dynamite" simulant.

Mix 4:
Water: 200 ml
Charcoal: 200 g
NaCl: 65 g
$CaCl_2$: 35 g
This mixture is useful for simulating black powder.

Mix 5A:
Glycerine: 200 g
Corn starch: 200 g
Alumina: 140 g
Hydrogen peroxide: 80 g (Do not measure out, squirt directly from bottle into mixer)
Orange paint (for example, Oil based paint or pigments): 10 g
Density of mixture: 1.4 g/cc
This mixture is useful for the "Semtex-H" simulant.

Mix 5B:
Glycerin: 200 g
Corn starch: 200 g
Alumina: 130 g
Hydrogen peroxide: 80 g (Do not measure out, squirt directly from bottle into mixer)
Black paint (for example, Oil based paint or pigments): 10 g
Density of mixture: 1.4 g/cc
This mixture is useful for the "Semtex-10" simulant Mix 5C:
Glycerin: 200 g
Corn starch: 200 g
Alumina: 120 g
Hydrogen peroxide: 80 g (Do not measure out, squirt directly from bottle into mixer)
Red paint (for example, Oil based paint or pigments): 10 g
Density of mixture: 1.4 g/cc
This mixture is useful for the "Semtex-1A" simulant Mix 6:
Glycerin: 200 g
Corn starch: 200 g
Alumina: 190 g Hydrogen peroxide: 80 g (Do not measure out, squirt directly from bottle into mixer)
Density of mixture: 1.6 g/cc
This mixture is useful for the "C4," and "M112 C4" simulants.
Mix 7:
Baking Soda: 4.5 cups
Water: 1 tablespoon
Vegetable oil: 1 cup
Paraffin wax: 2 blocks (32 oz.)
20 drops yellow food coloring
Density of mixture: 1.5 g/cc
This mixture is useful for the "Cast TNT" simulant.
Mix 8:
Baking Soda: 4.5 cups
Water: 1 tablespoon
Vegetable oil: 1 cup
Paraffin wax: 2 blocks (32 oz.)
20 drops yellow food coloring
Corn starch: 1.5 cups
Density of mixture: 1.48 g/cc
This mixture is useful for the "PE 4" and "TNT Cast Booster" simulants.
Mix 9:
Baking Soda: 3 cups
Paraffin wax: 2 blocks (32 oz.)
Density of mixture: 1.48 g/cc
This mixture is useful for the "PE 4" and "TNT Cast Booster" simulants.
Mix 10:
Baking Soda: 2 cups
Corn Starch: 1 cup
Water: 1.5 cups
Vegetable oil: 1 tablespoon
Density of mixture: 1.40 g/cc
Packed in cardboard tube with eight inch length, 1.5 inch diameter, 0.08 inch wall thickness.
Density of mixture and cardboard tube: 1.57 g/cc
This mixture in the cardboard tube is useful for simulating plastic explosives.
Mix 11:
Baking soda: 2 cups
Corn starch: 2 cup
Water: 1 cup
Vegetable oil: 0.5 cup
Density of mixture: 1.5 g/cc
Packed in cardboard tube with eight inch length, 1.5 inch diameter, 0.08 inch wall thickness.
Density of mixture and cardboard tube: 1.6 g/cc
This mixture in the cardboard tube is useful for simulating plastic explosives.
Mix 12:
Confectioner sugar (e.g. Domino™ Confectioner Sugar): 2 cups
Corn syrup: 1 cup
Vegetable oil spray (to coat outside to reduce stickiness)
Density of mixture: 1.4 g/cc
Packed in cardboard tube with five inch length, 1.5 inch diameter, 0.08 inch wall thickness.
Density of mixture and cardboard tube: 1.5 g/cc
This mixture in the cardboard tube is useful for simulating PE-4 stick and sheet explosive.
Mix 13:
Corn Starch: 1 cup
Magnesium Citrate Powder: 2 cups
Baking soda: 0.25 cups
Water: 1.5 cups water
Vegetable Oil: 2 Tablespoons
Density of mixture: 1.20 g/cc
Packed in cardboard tube with eight inch length, 1.5 inch diameter, 0.08 inch wall thickness.
Density of mixture and cardboard tube: 1.33 g/cc
This mixture in the cardboard tube is useful for simulating plastic explosives.
Mix 14:
Dark brown sugar
Density of mixture: 0.86 g/cc
Packed in cardboard tube with eight inch length, 1.5 inch diameter, 0.08 inch wall thickness.
Density of compressed mixture and cardboard tube: 1.22 g/cc
Density of non-compressed mixture and cardboard tube: 1.15 g/cc
This mixture in the cardboard tube is useful for simulating dynamite
Mix 15:
Pure Cane sugar
Density of mixture: 0.74 g/cc
Packed in cardboard tube with eight inch length, 1.5 inch diameter, 0.08 inch wall thickness.
Density of compressed mixture and cardboard tube: 1.11 g/cc
Density of non-compressed mixture and cardboard tube: 1.04 g/cc
This mixture in the cardboard tube is useful for simulating dynamite.
Mix 16:
Dry Magnesium Citrate Powder
Density of mixture: 1.12 g/cc
Packed in cardboard tube with eight inch length, 1.5 inch diameter, 0.08 inch wall thickness.
Density of compressed mixture and cardboard tube: 1.12 g/cc
Density of non-compressed mixture and cardboard tube: 1.08 g/cc
This mixture in the cardboard tube is useful for simulating dynamite.
TATP Simulant:
Polyethylene Powder: 800 g
Granulated Cane Sugar: 400 g
99% Glycerin: 110 g
Borax: 200 g
HMTD Simulant:
Polyethylene Powder: 600 g
Baking Soda: 250 g
99% Glycerin: 81 g
Borax: 150 g
PETN Simulant:
Polyethylene Powder: 200 g
Granulated Cane Sugar: 600 g
99% Glycerin: 60 g
Borax: 575 g
Baking Soda: 50 g
RDX Simulant:
Polyethylene Powder: 50 g
Granulated Cane Sugar: 500 g
99% Glycerin: 60 g
Borax: 700 g
Baking Soda: 150 g
Hydrogen Peroxide (30%) Simulant:
75% Water
20% Cane Sugar
5% Sodium Chloride
Blue Highlighter Fluid
PLX Simulant:
62% Water
31% Cane Sugar 4% Sodium Chloride 2% Corn Syrup The densities of various explosive simulating materials and mixtures may be adjusted to more closely conform to a density of a particular explosive. For example, when dark brown sugar or confectioner sugar is used in the simulant, the sugar may be compressed to a particular packing density needed to achieve a desired density in a container in which it is supplied. Mixtures of materials including water and oil may be adjusted in density by varying the amount of water versus oil or by using different oils. For example, a mixture of one cup corn starch, two cups baking soda, and one tablespoon vegetable oil will provide a mixture with a density of about 1.4 g/cc. By increasing the amount of oil by 0.5 cups and reducing the amount of water by 0.5 cups the density of the mixture may be increased to about 1.6 g/cc. Further variations of the oil and water mixtures can achieve varying densities in a range of from about 1.4 g/cc to about 1.6 g/cc. The corn starch/water/oil mixture may be formed from a mixture of 1.5 cups water, one cup corn starch and one tablespoon of vegetable oil to provide a density of about 1.6 g/cc. In another example, the density of the clay may be adjusted by adjusting its water content or by selecting different types of clay.

In some embodiments, the various explosive simulating materials and mixtures may be hermetically sealed in a package to reduce the potential for water vapor to enter or exit the material, which could alter its density. In some embodiments, the explosive simulating materials and mixtures may be vacuum sealed in a plastic film having a low water vapor transmission rate, for example, a polyester, polypropylene, or polychlorotrifluoroethylene (PCTFE) film. In some embodiments, the plastic film may be metalized to further reduce its water vapor transmission rate.

In accordance with a first broad aspect disclosed herein, one or more explosive simulants may be utilized in a simulated IED Circuit Kit. The components of an embodiment of a simulated IED Circuit Kit 100 are illustrated in FIG. 1. The simulated IED Circuit Kit 100 may include a substrate board 110 on which other components are mounted. The substrate board 110 may be formed from cardboard, a sheet of plastic, fiberboard, for example, a medium density fiberboard, wood, or any other rigid or semi-rigid material. The various components of the simulated IED Circuit Kit 100 may be non-releasably secured to the substrate board 110, for example, with an adhesive, or may be releaseably secured to the substrate board 110 with releasable connectors, for example, snaps, VELCRO® hook and loop fasteners, or other fasteners or fastening mechanisms known in the art.

Figure 2:
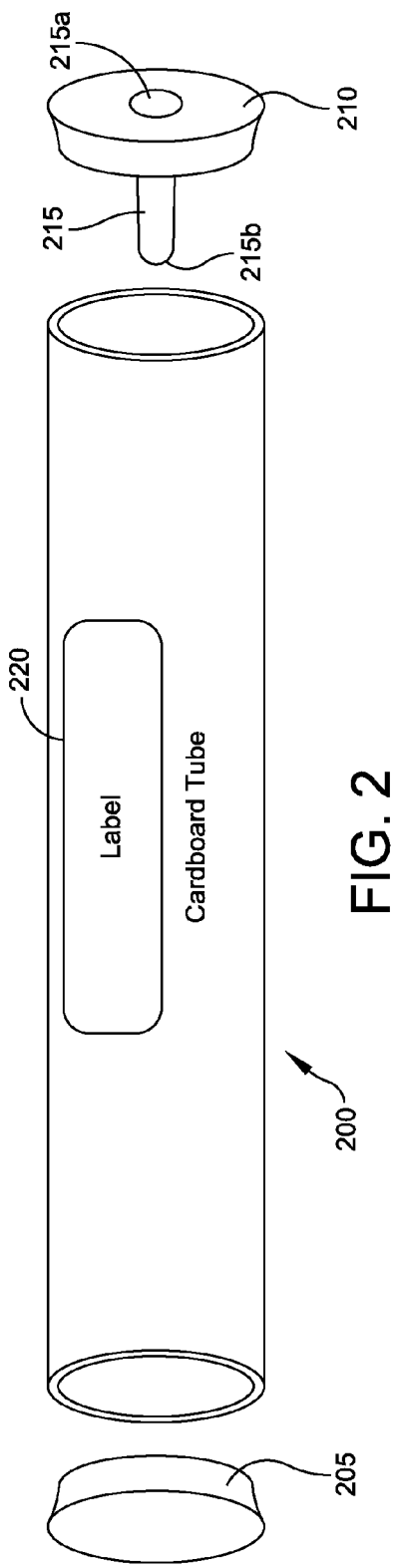
FIG. 2 illustrates an embodiment of a package for an explosive simulant.
Figure 3B:
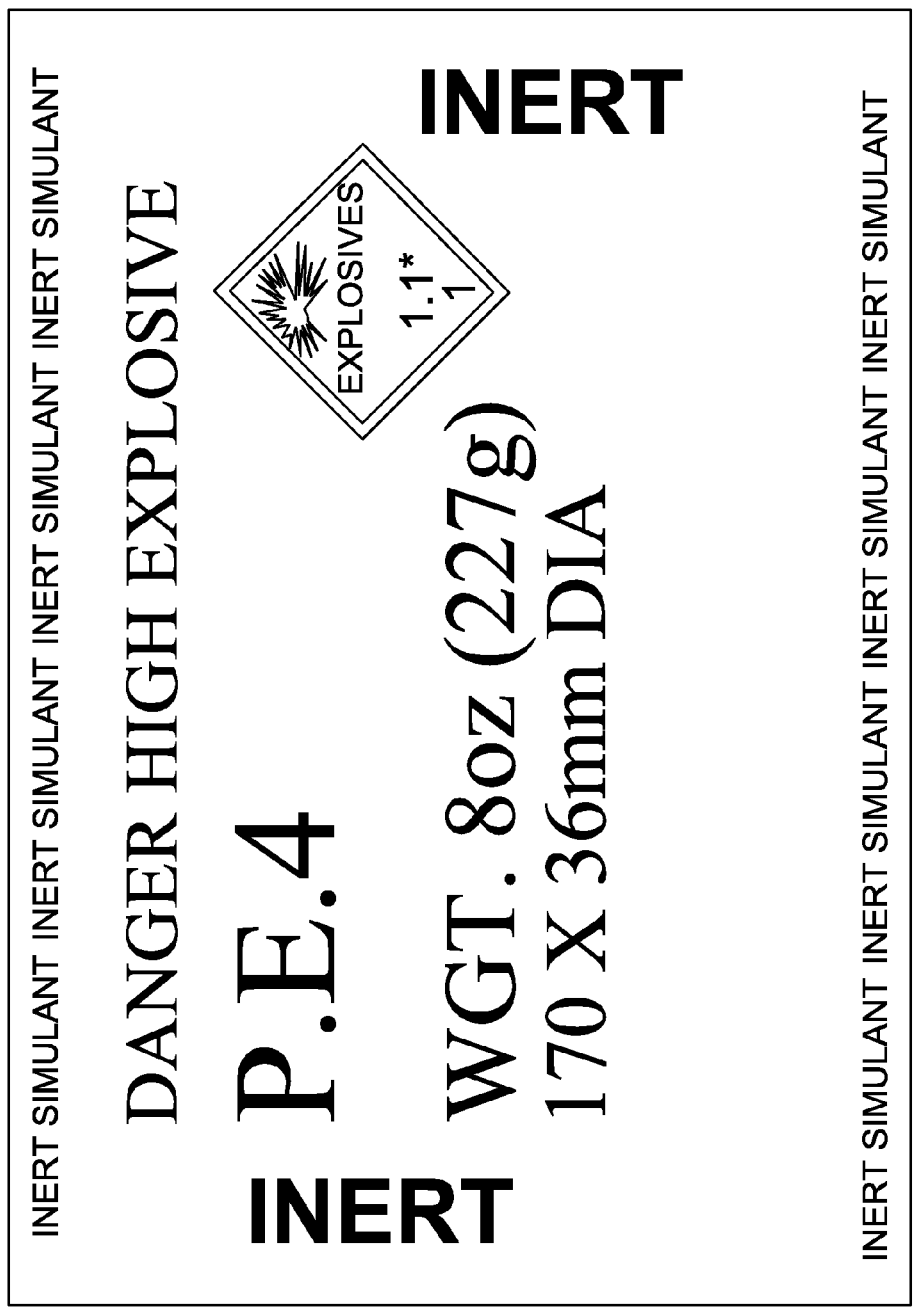
FIG. 3B illustrates an embodiment of a label for a package including an explosive simulant.

An explosive simulant 120 may be mounted on the substrate board 110. In some embodiments, the explosive simulant may be packaged inside a tube, for example, a cardboard tube 200 as illustrated in FIG. 2 or a plastic tube. The cardboard tube 200 or plastic tube may be filled with the explosive simulant 120 and sealed with end caps 205, 210. The thickness of the cardboard tube 200 or plastic tube may be selected to accommodate explosive simulants 120 packed in the cardboard tube 200 or plastic tube at various packing pressures to achieve desired packing densities. In some embodiments, the thickness of the wall of the cardboard tube 200 or plastic tube is about 0.08 inches. One of the end caps, for example, end cap 210 may include a plastic tube 215 which is open on an external side 215a and closed on an internal side 215b. The plastic tube may be used as a cap well to retain a simulated blasting cap 130 and may have dimensions of, for example, about ⅞ inches in diameter by about 1.5 inches in length. The tube 200 may also include a label 220 identifying the explosive material simulated and indicating that the simulant is inert. Non-limiting examples of different labels 310, 320, and 330 are illustrated in FIGS. 3A, 3B, and 3C. The tube 200 may have dimensions of, for example, about 1.5 inches in diameter by about eight inches in length or by about five inches in length, although it should be understood that these and other dimensions of various components disclosed herein are provided as examples only and may vary in different embodiments.

Returning to FIG. 1, a simulated blasting cap 130 may be provided inserted into the explosive simulant 120 or package including the explosive simulant 120. The simulated blasting cap 130 may include an indicator 135, for example, an incandescent light or an LED. The indicator 135 may illuminate upon a charge being sent to the simulated blasting cap 130 to provide an indication to a person training with the simulated IED Circuit Kit 100 that an action the trainee has taken would have resulted in the explosive simulant 120, had it been real, being detonated. The simulated IED Circuit Kit 100 further includes a safe and arming switch 150, and a power source 160, which may include, for example, a battery holder and/or one or more batteries, and a firing switch area 140 which in various embodiments may house a trigger switch.

Examples of various embodiments of the simulated IED Circuit Kit 100 are illustrated in FIGS. 4A-27. It should be appreciated that the various components illustrated in any of these embodiments may be substituted for one another or provided in addition to the components illustrated in other embodiments.

Figure 4B:
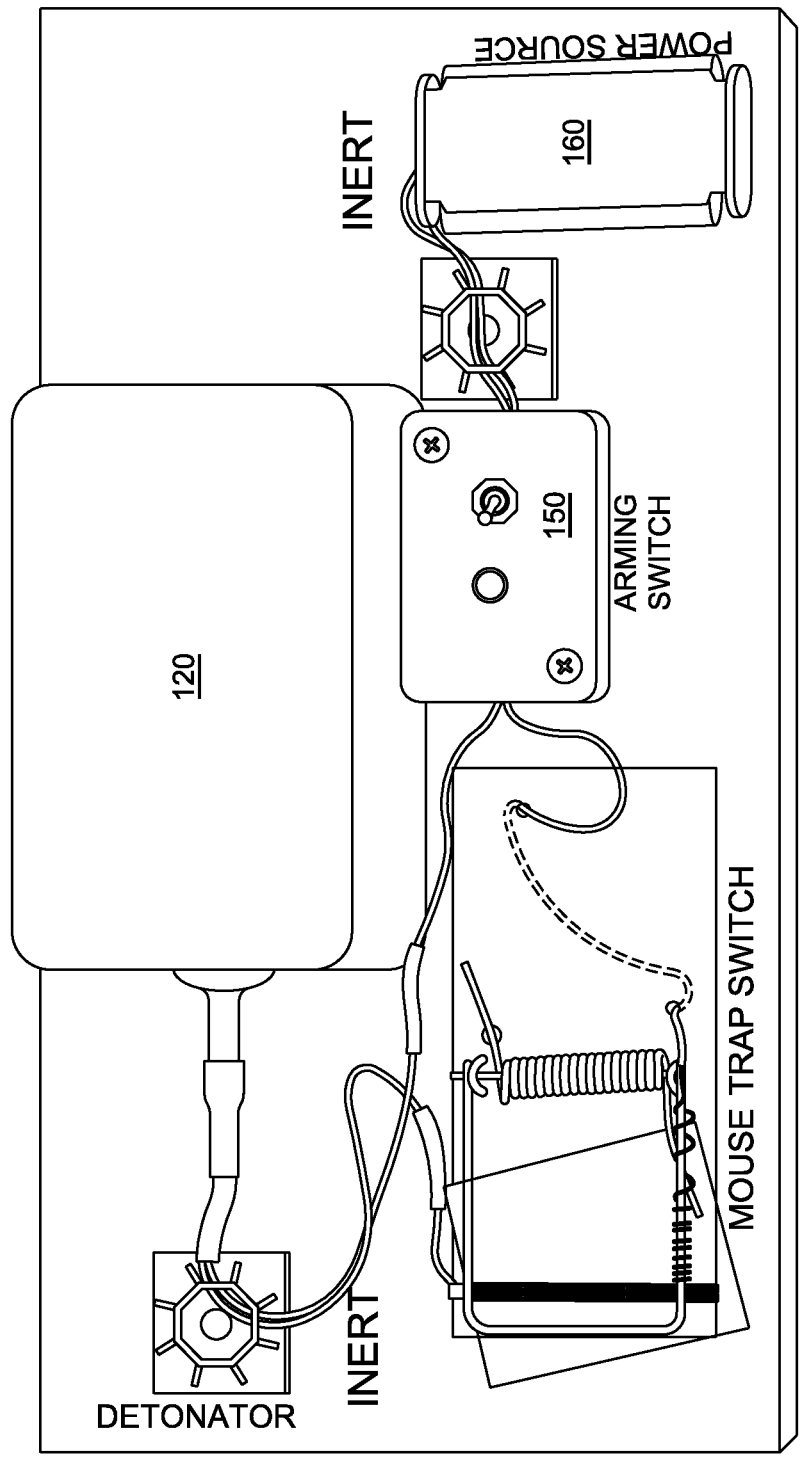
FIG. 4B illustrates an embodiment of a simulated IED Circuit Kit.

In FIG. 4A, the trigger switch is a mousetrap 145 and the simulant 120 is a simulant for ammonium based dynamite. Electrical connection is made from the power source 160 to the spring of the mousetrap 145 and to a base of the mousetrap 145. The circuit is completed when a non-conductive material 145a, for example, a piece of paper or plastic is pulled from under the spring of the mousetrap 145. FIG. 4B illustrates a similar mousetrap switch assembly as FIG. 4A, but with a simulated Semtex assembly and arming switch. It should be appreciated that arming switches may be included in any of the simulated IED Circuit Kit 100 illustrated in FIGS. 4-27 even if not explicitly illustrated in each example.

Figure 5A:
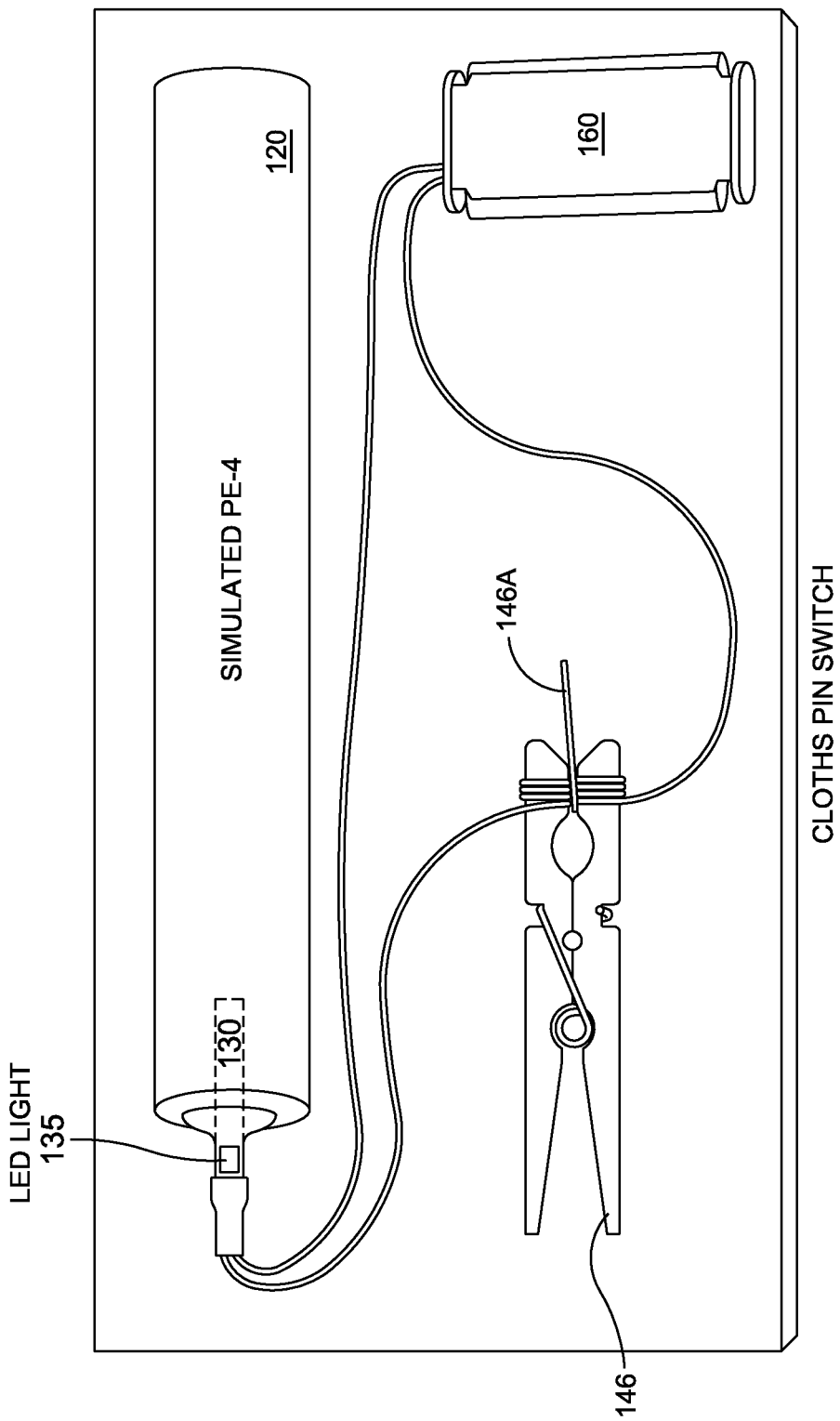
FIG. 5A illustrates an embodiment of a simulated IED Circuit Kit.
Figure 5B:
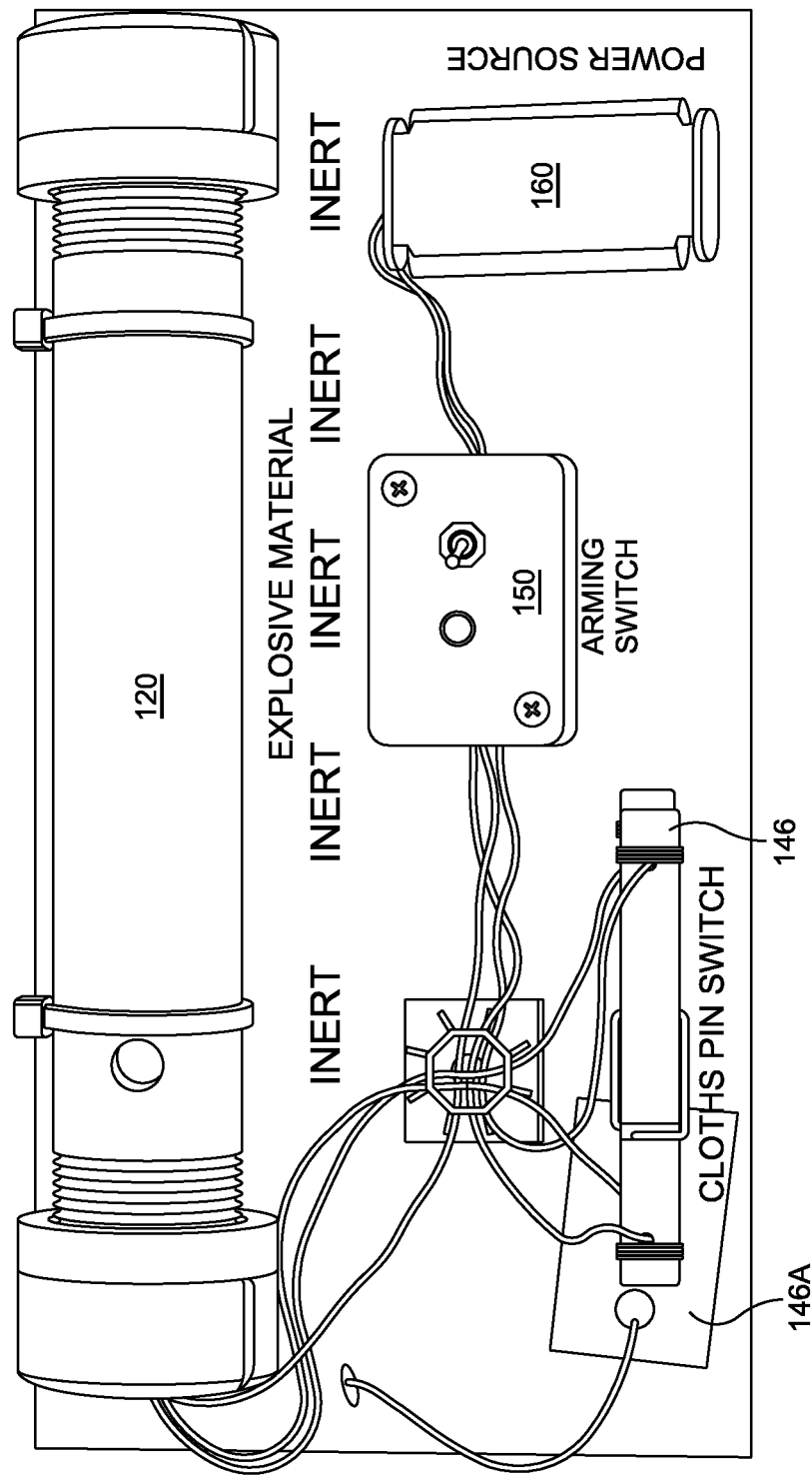
FIG. 5B illustrates an embodiment of a simulated IED Circuit Kit.

In FIG. 5A, the trigger switch is a spring-biased clothespin 146 and the simulant 120 is a simulant for PE-4. Electrical connection is made from the power source 160 to jaws of the clothespin. The circuit is completed when a non-conductive material 146a, for example, a piece of paper or plastic is pulled from between the jaws of the clothespin 146. FIG. 5B illustrates a similar clothespin switch assembly as FIG. 5A but further including an arming switch and a simulated pipe bomb.

Figure 6:
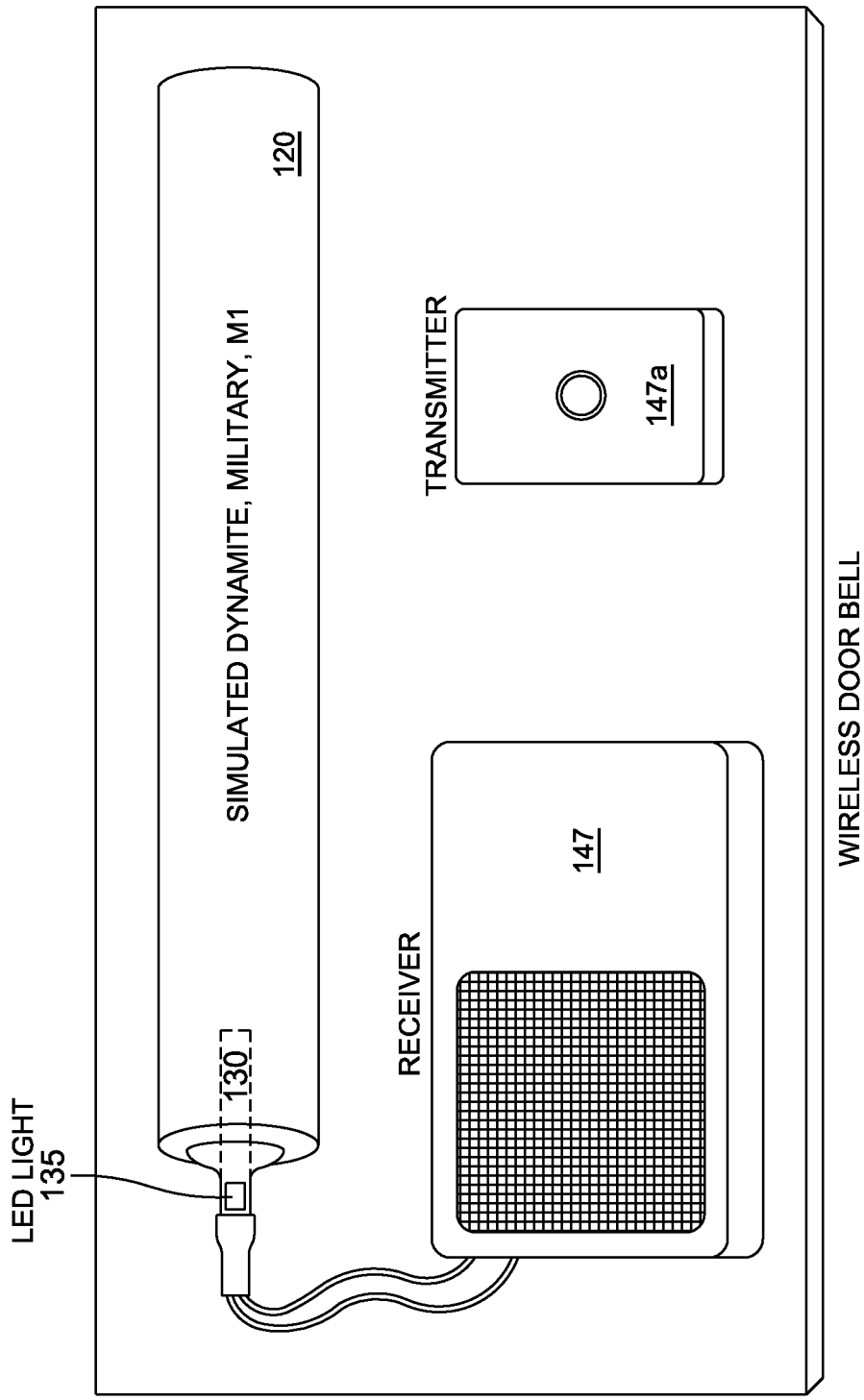
FIG. 6 illustrates an embodiment of a simulated IED Circuit Kit.

In FIG. 6, the trigger switch is a modified receiver 147 for a wireless doorbell which has wires in electrical communication between a circuit that would otherwise activate the doorbell and the simulated blasting cap 130. The simulant 120 is a simulant for military grade dynamite. Current is sent from the wireless doorbell receiver 147 to the simulated blasting cap 130 upon activation of the wireless doorbell receiver 147 by a transmitter 147a.

Figure 7:
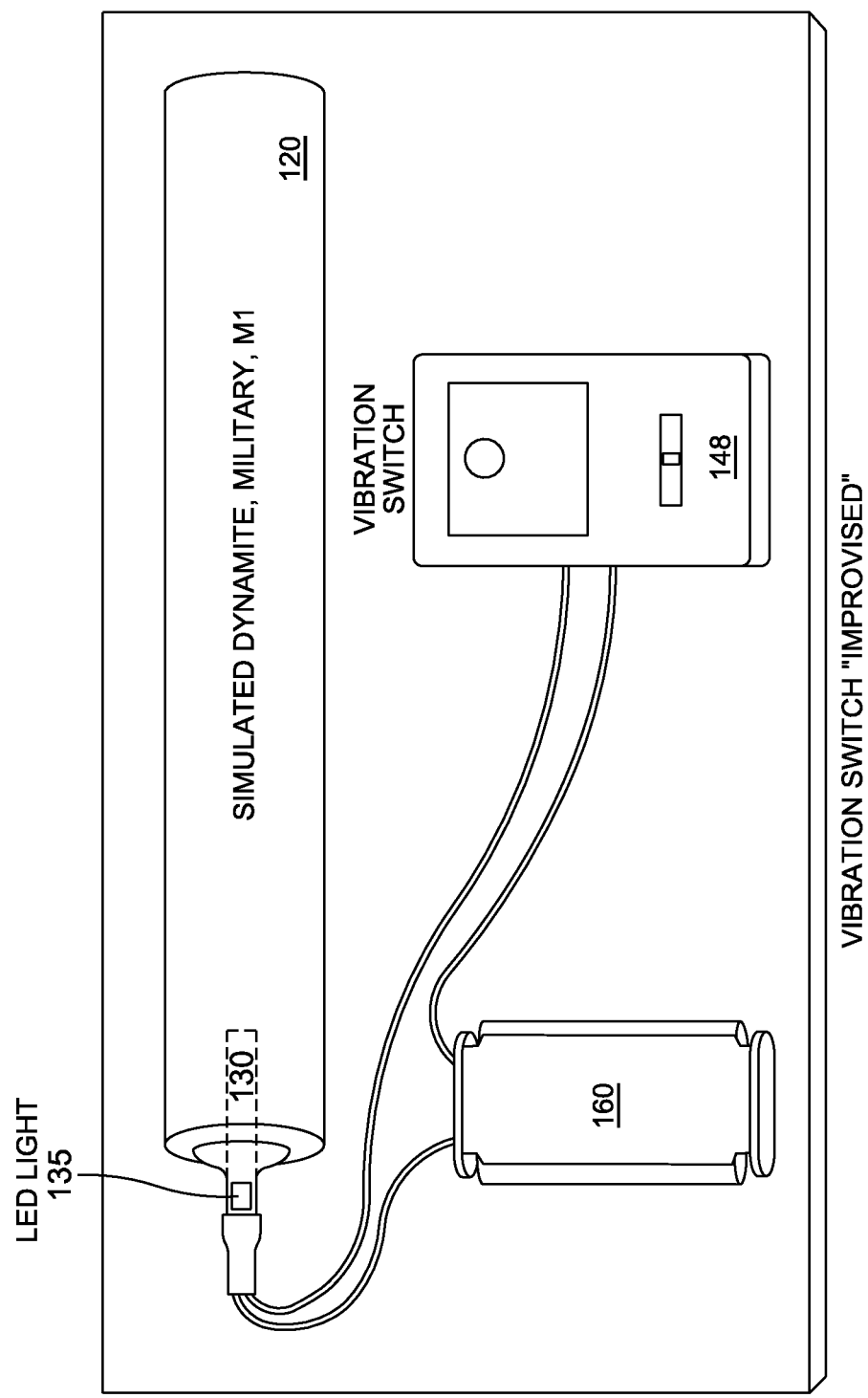
FIG. 7 illustrates an embodiment of a simulated IED Circuit Kit.

In FIG. 7, the trigger switch is a vibration switch 148 which has wires in electrical communication between the power source 160, a circuit in the vibration switch 148 which closes upon detection of vibration, and the simulated blasting cap 130.

Figure 8:
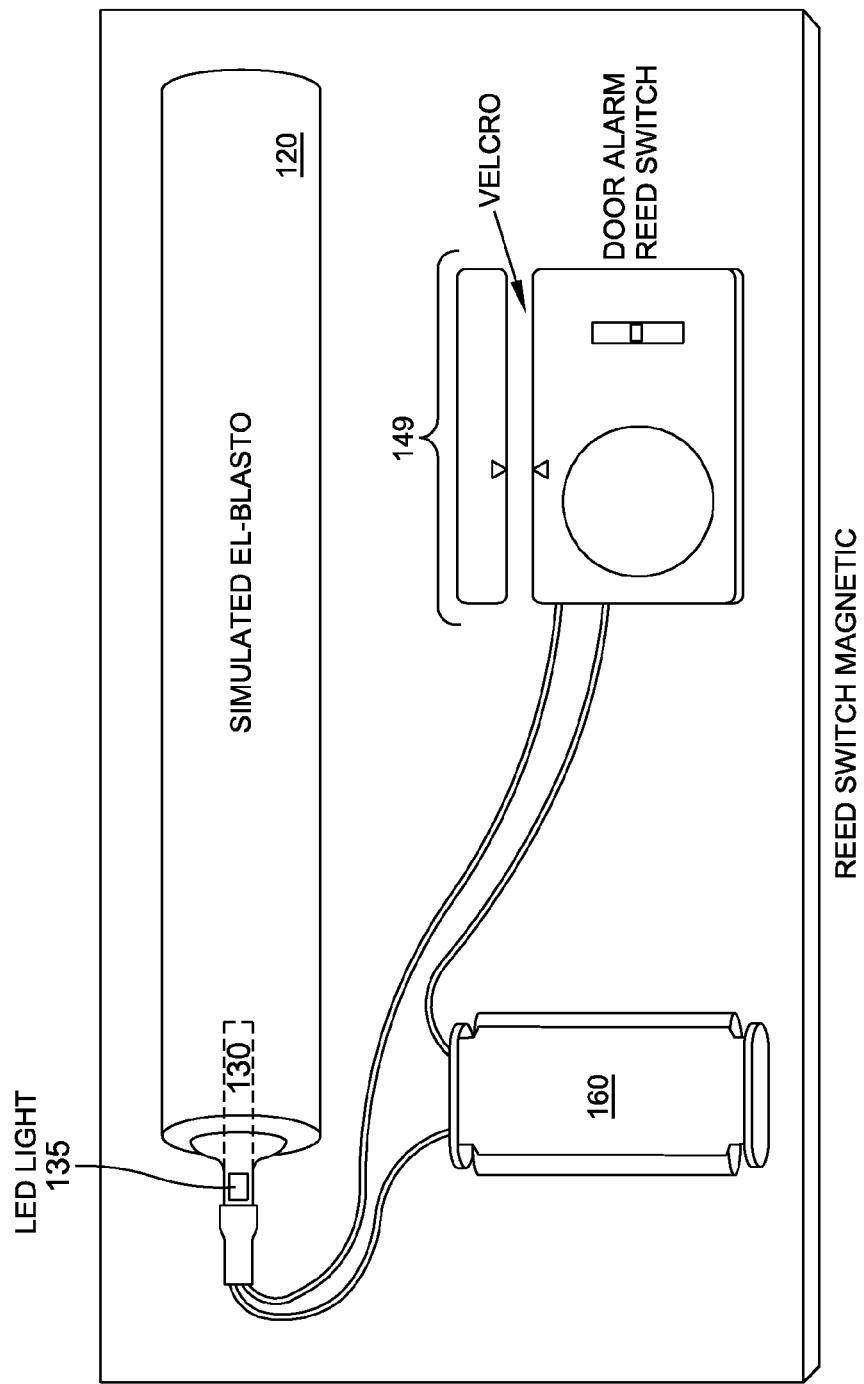
FIG. 8 illustrates an embodiment of a simulated IED Circuit Kit.

In FIG. 8, the trigger switch is a door alarm reed switch 149 which has wires in electrical communication between the power source 160, a circuit in the door alarm reed switch 149 which closes upon activation of the switch 149, and the simulated blasting cap 130. The simulant 120 is a simulant for "El-Blasto" dynamite.

Figure 9:
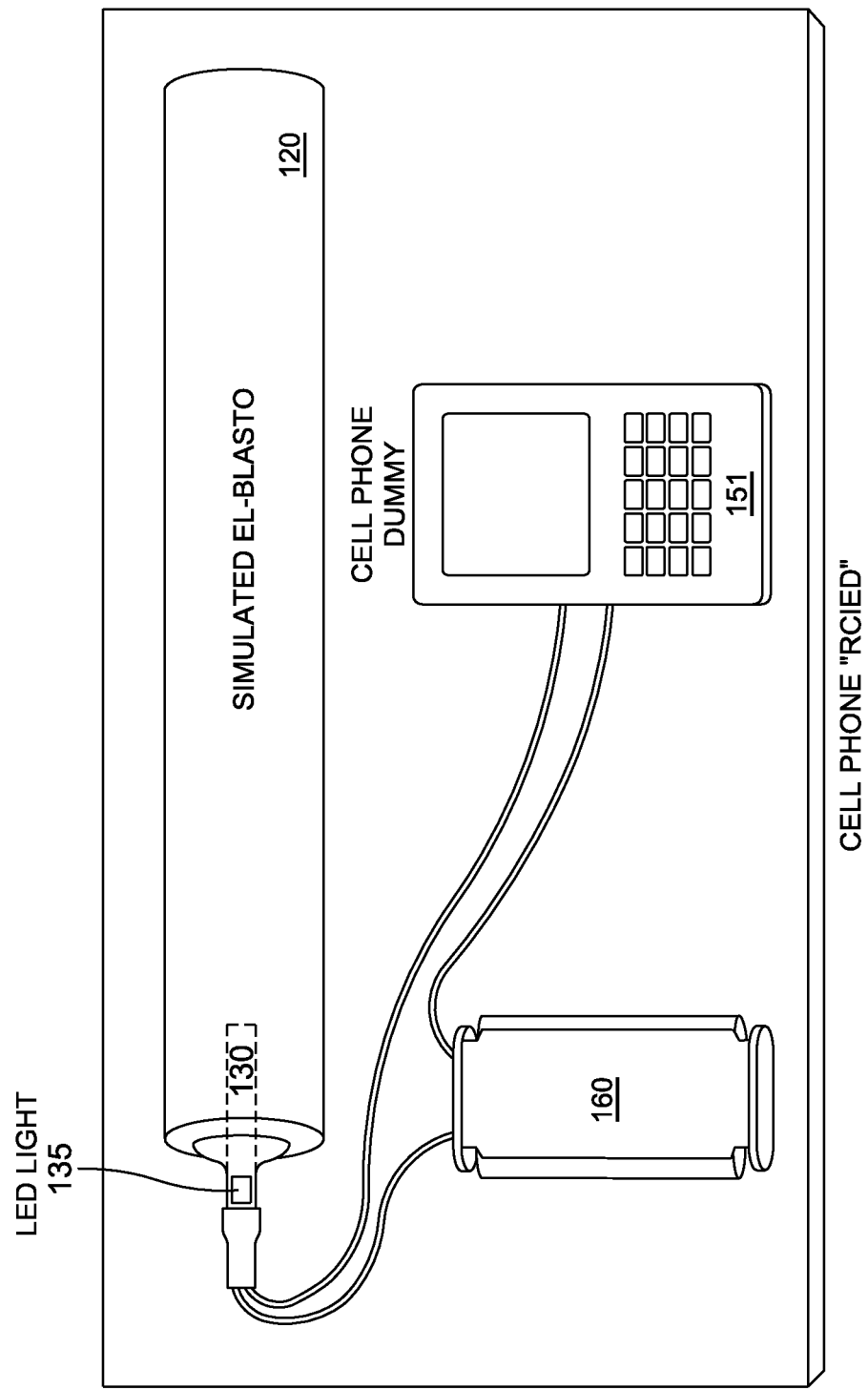
FIG. 9 illustrates an embodiment of a simulated IED Circuit Kit.

In FIG. 9, the trigger switch is a modified cell phone or cell phone dummy 151 which has wires in electrical communication between the simulated blasting cap 130 and a circuit that would otherwise active, for example, a ringer of the cell phone 151. The simulant 120 is a simulant for "El-Blasto" dynamite.

Figure 10:
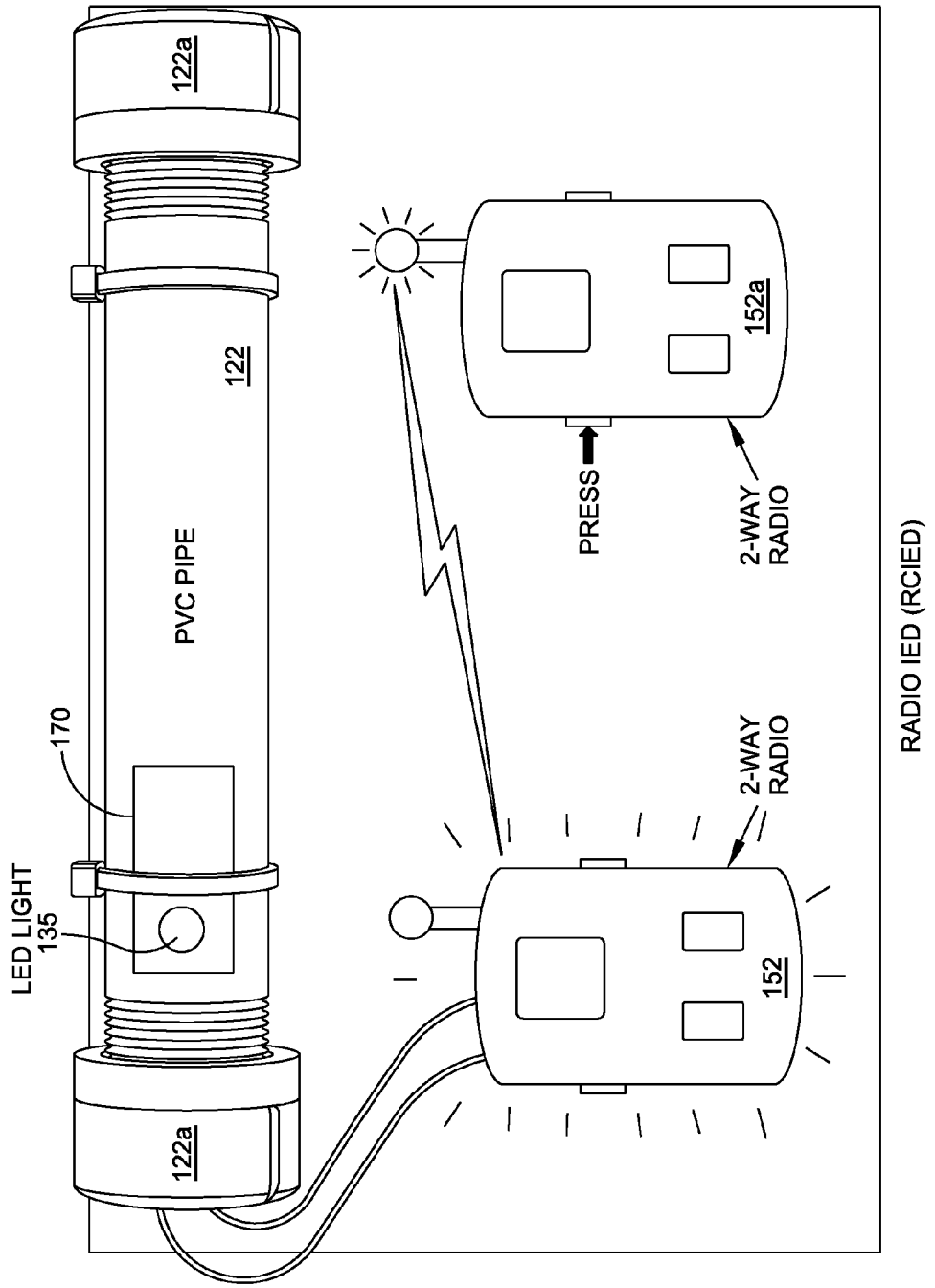
FIG. 10 illustrates an embodiment of a simulated IED Circuit Kit.

In FIG. 10, the trigger switch is a modified two way radio 152 which has wires in electrical communication between the simulated blasting cap 130 and a circuit that would otherwise activate, for example, a speaker of the two way radio 152 upon contact with the two way radio 152 from a second two way radio 152a. The simulant 120 is packed in a PVC pipe 122 which may have a length of, for example, about eight inches and a diameter of, for example, about 1.25 inches or about two inches, and is fitted with end caps 122a which may be screwed onto the ends of the PVC pipe 122 and/or glued in place onto the ends of the PVC pipe 122. The PVC pipe 122 includes a window 170 through which an indicator light 135 may be viewed. Alternatively, the PVC pipe 122 may be empty.

Figure 11:
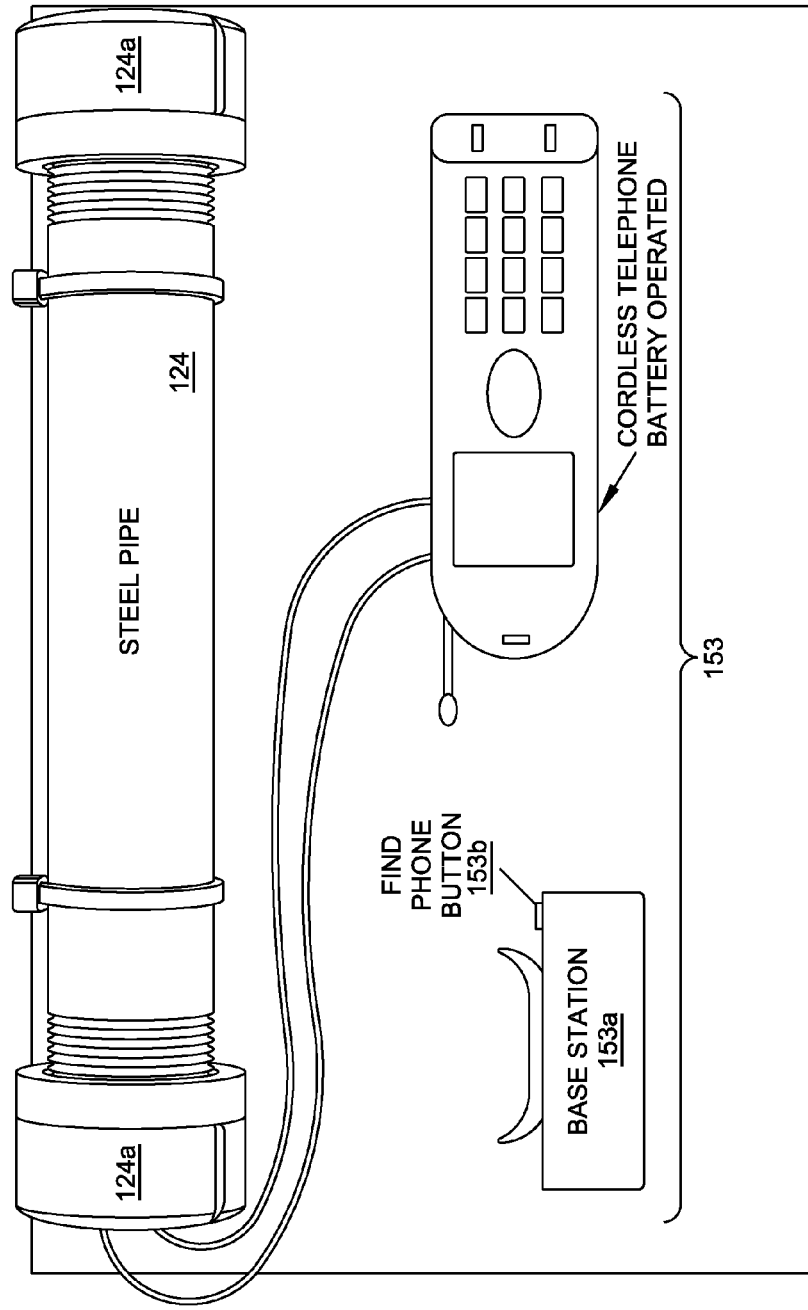
FIG. 11 illustrates an embodiment of a simulated IED Circuit Kit.

In FIG. 11, the trigger switch is a modified cordless telephone handset 153 which has wires in electrical communication between the simulated blasting cap 130 and a circuit that would otherwise activate, for example, a ringer of the cordless telephone 153 upon activation of a "find phone" button 153b on a base station 153a of the cordless telephone 153. The simulant is packed in a steel pipe 124 which may have a length of, for example, about six or about eight inches and a diameter of, for example, about one inch or about 1.5 inches, and is fitted with end caps 124a which may be screwed onto the ends of the steel pipe 124 and/or glued in place onto the ends of the steel pipe 124. Alternatively, the steel pipe 124 may be empty.

Figure 12:
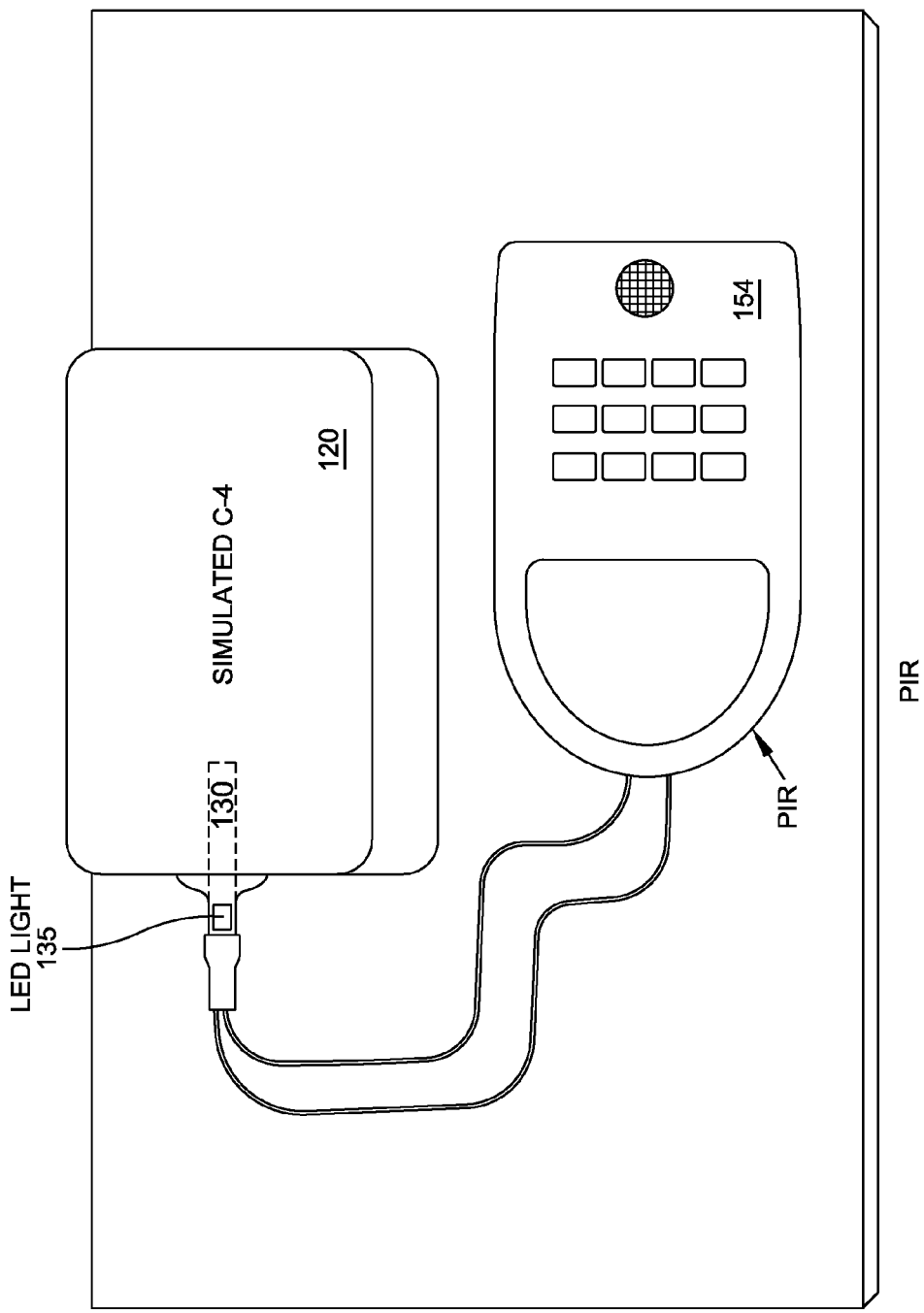
FIG. 12 illustrates an embodiment of a simulated IED Circuit Kit.

In FIG. 12, the trigger switch is a passive infrared receiver (PIR) 154 which has wires in electrical communication between the power source 160 (internal to the PIR 154, but in alternate embodiments, external to the PIR 154), a circuit in the PIR 154 which closes upon detection of infrared (IR) light, and the simulated blasting cap 130. The simulant 120 is a simulant for C-4 explosive.

Figure 13:
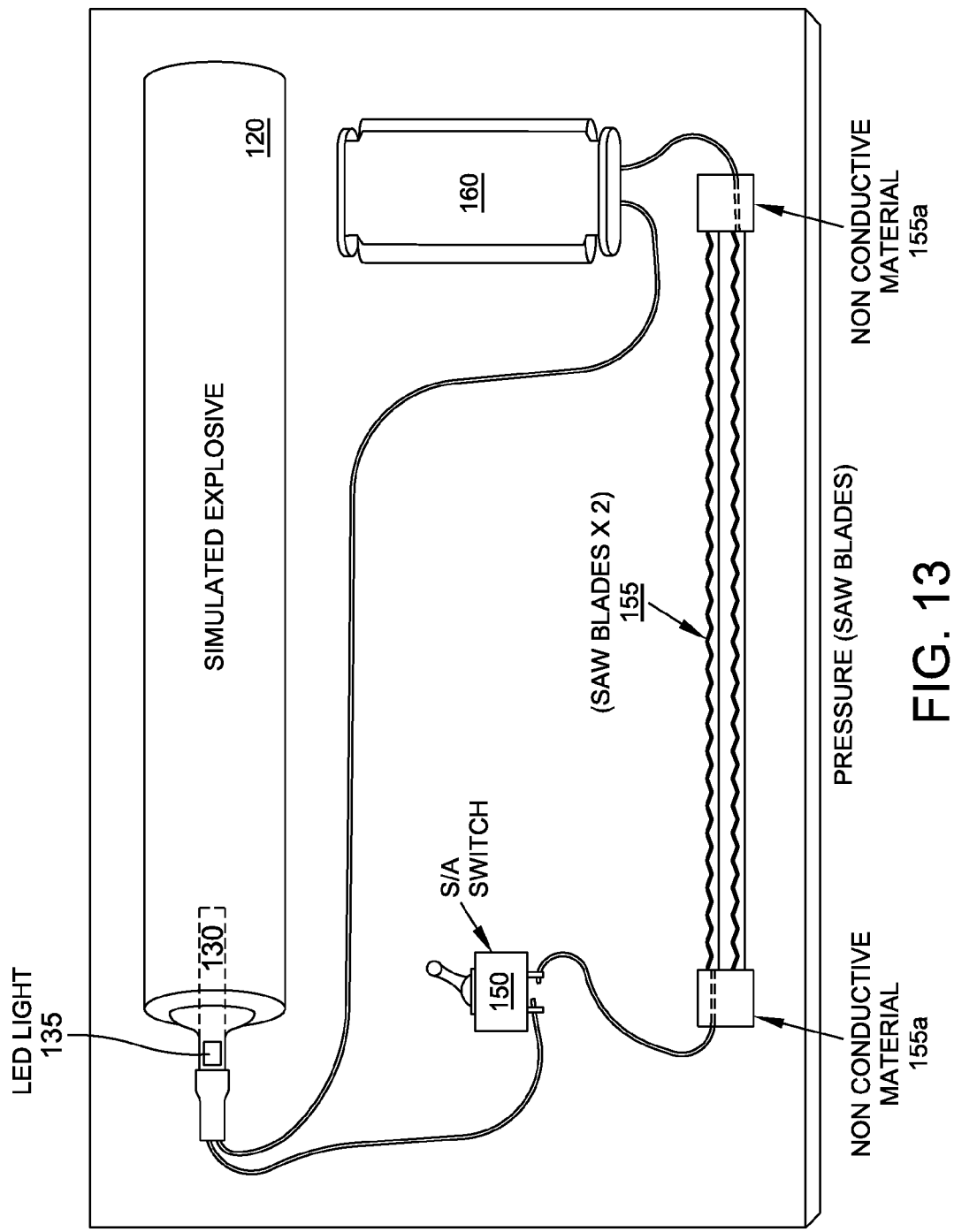
FIG. 13 illustrates an embodiment of a simulated IED Circuit Kit.

In FIG. 13, the trigger switch is a pair of saw blades 155 in electrical communication between the power source 160 and the simulated blasting cap 130. The saw blades 155 may be held apart from one another by one or more blocks of a non-conductive material 155a. The circuit is closed, sending power to the simulated blasting cap 130, upon application of pressure which brings the saw blades 155 into contact with one another.

Figure 14:
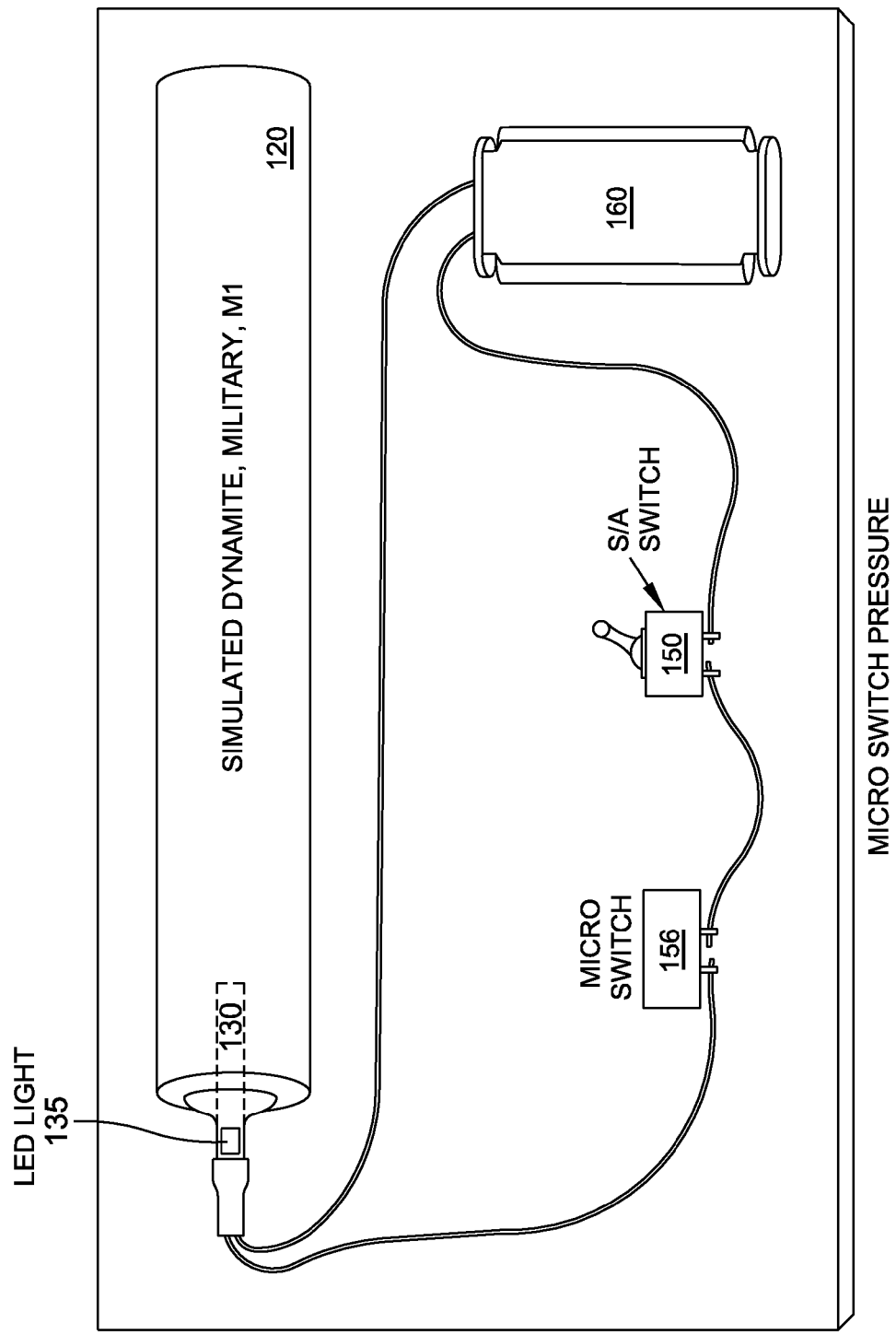
FIG. 14 illustrates an embodiment of a simulated IED Circuit Kit.

In FIG. 14, the trigger switch is a pressure activated micro switch 156 in electrical communication between the power source 160 and the simulated blasting cap 130. The simulant 120 is a simulant for military grade dynamite.

Figure 15:
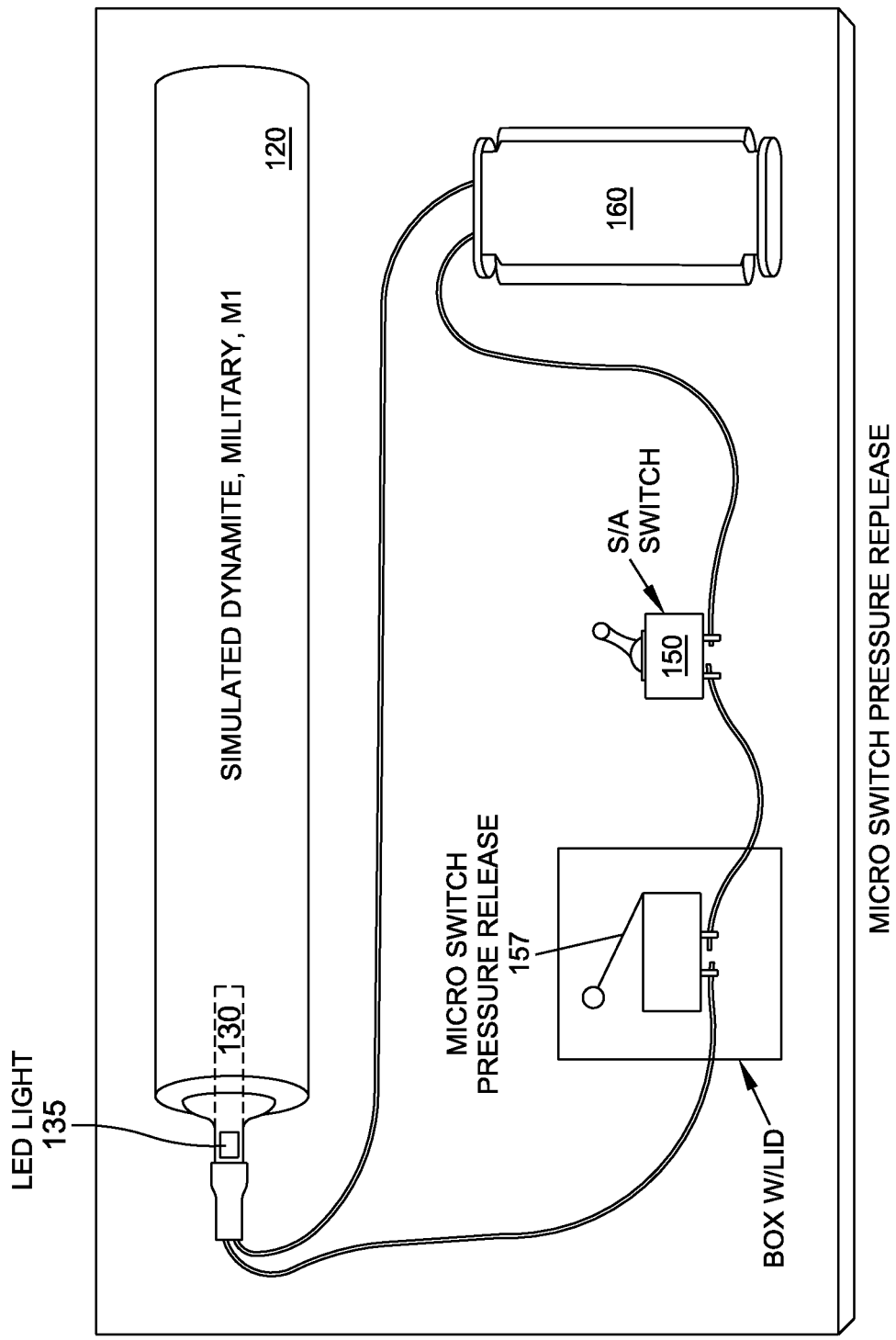
FIG. 15 illustrates an embodiment of a simulated IED Circuit Kit.

In FIG. 15, the trigger switch is a pressure activated micro switch 157 which closes a circuit between the power source 160 and the simulated blasting cap 130 upon a release of pressure on the switch 157, for example, by opening a box 157a in which the switch 157 is disposed. The simulant 120 is a simulant for military grade dynamite.

Figure 16:
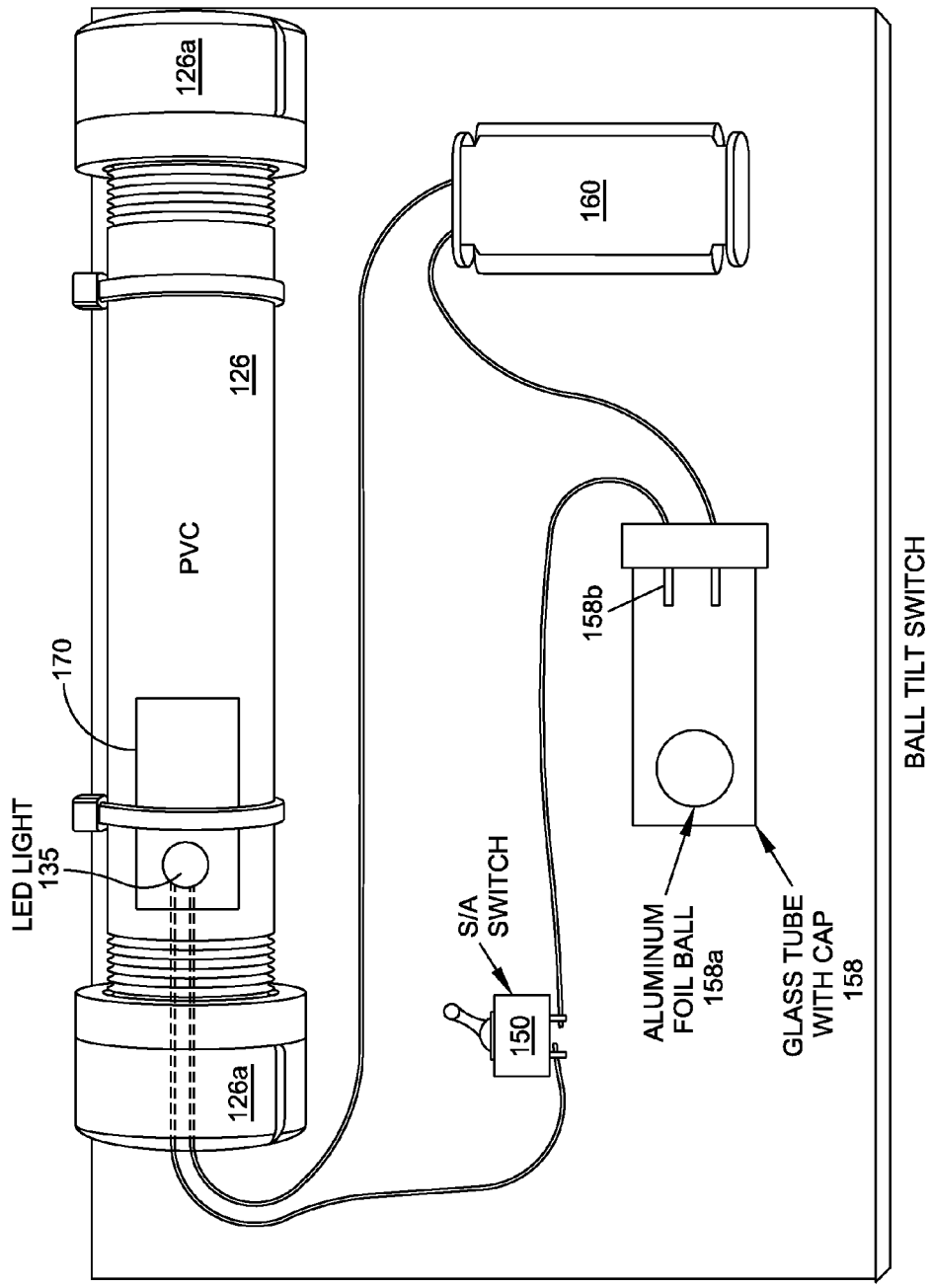
FIG. 16 illustrates an embodiment of a simulated IED Circuit Kit.

In FIG. 16, the trigger switch is a tilt switch 158 which closes a circuit between the power source 160 and the simulated blasting cap 130 upon tilting of the switch 158 so that a conductive ball 158a, for example, an aluminum foil ball, rolls into contact with a pair of electrical contacts 158b within the switch 158. The simulant 120 is packed in a PVC pipe 126 which may have a length of, for example, eight inches and a diameter of, for example, about 1.25 inches or about two inches, and is fitted with end caps 126a which may be screwed onto the ends of the PVC pipe 126 and/or glued in place onto the ends of the PVC pipe 126. The PVC pipe 126 includes a window 170 through which an indicator light 135 may be viewed. Alternatively, the PVC pipe 126 may be empty.

Figure 17:
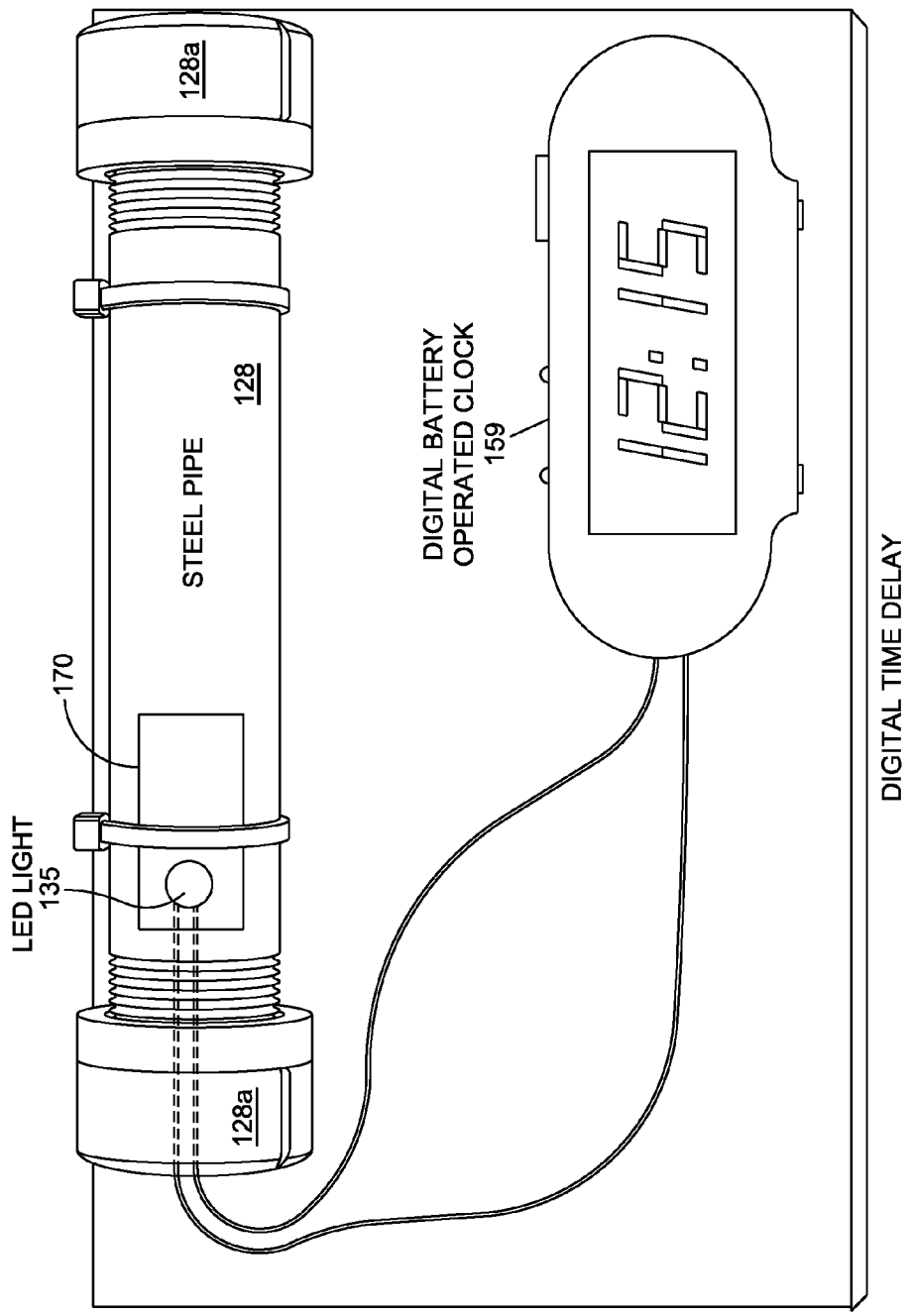
FIG. 17 illustrates an embodiment of a simulated IED Circuit Kit.

In FIG. 17, the trigger switch is a modified digital clock 159 which has wires in electrical communication between the simulated blasting cap 130 and a circuit that would otherwise activate, for example, an alarm of the clock 159. Alternatively, the trigger switch could be a digital kitchen timer or other form of digital timer. The power source 160 may be located internal or external to the digital timer. The simulant is packed in a steel pipe 128 which may have a length of, for example, about six inches or about eight inches and a diameter of, for example, about one inch or about 1.5 inches, and is fitted with end caps 128a which may be screwed onto the ends of the steel pipe 128 and/or glued in place onto the ends of the steel pipe 128. The steel pipe 128 includes a window 170 through which an indicator light 135 may be viewed. Alternatively, the steel pipe 128 may be empty.

Figure 18:
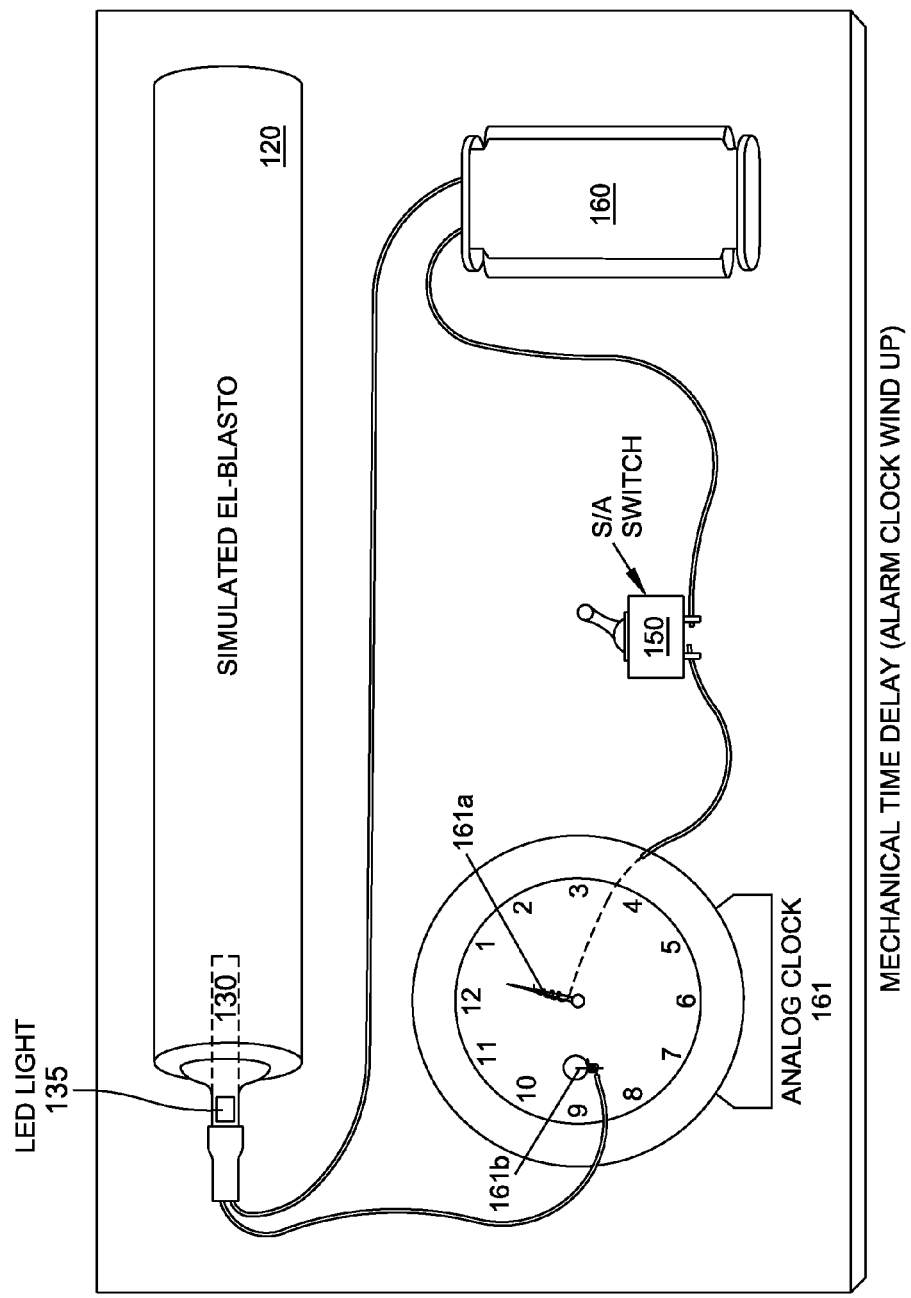
FIG. 18 illustrates an embodiment of a simulated IED Circuit Kit.

In FIG. 18, the trigger switch is a modified analog clock 161, for example, a Advance Super Bell key wound alarm clock, which closes a circuit between the power source 160 and the simulated blasting cap 130 upon an electrical contact mounted on a hand 161a of the clock 160 reaching a second electrical contact 161b disposed on the face of the clock 160. The simulant 120 is a simulant for "El-Blasto" dynamite.

Figure 19:
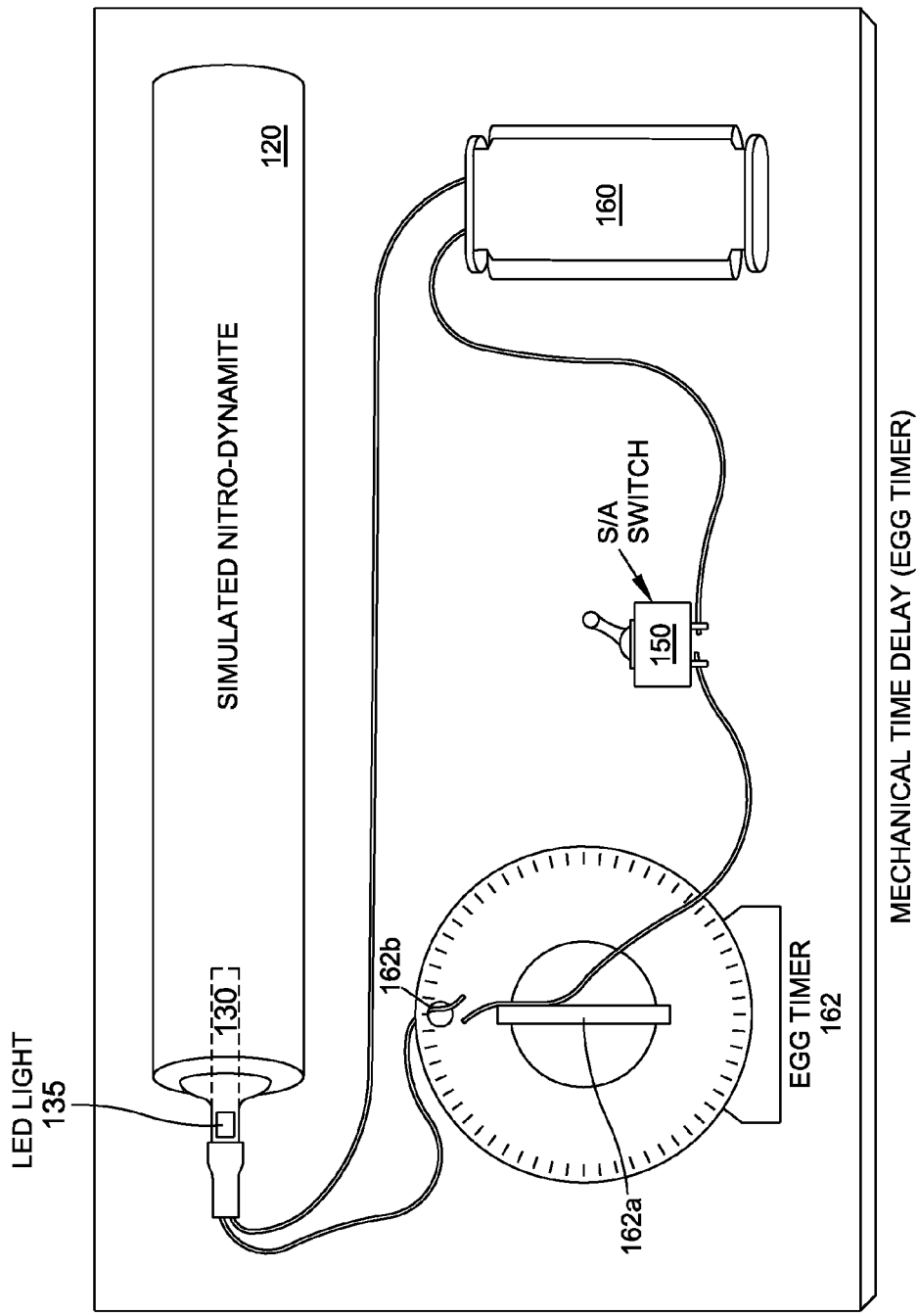
FIG. 19 illustrates an embodiment of a simulated IED Circuit Kit.

In FIG. 19, the trigger switch is an egg timer 162 which closes a circuit between the power source 160 and the simulated blasting cap 130 upon an electrical contact mounted on a handle 162a of the timer 162 reaching a second electrical contact 162b disposed on the face of the timer. The simulant 120 is a simulant for nitro-dynamite.

Figure 20:
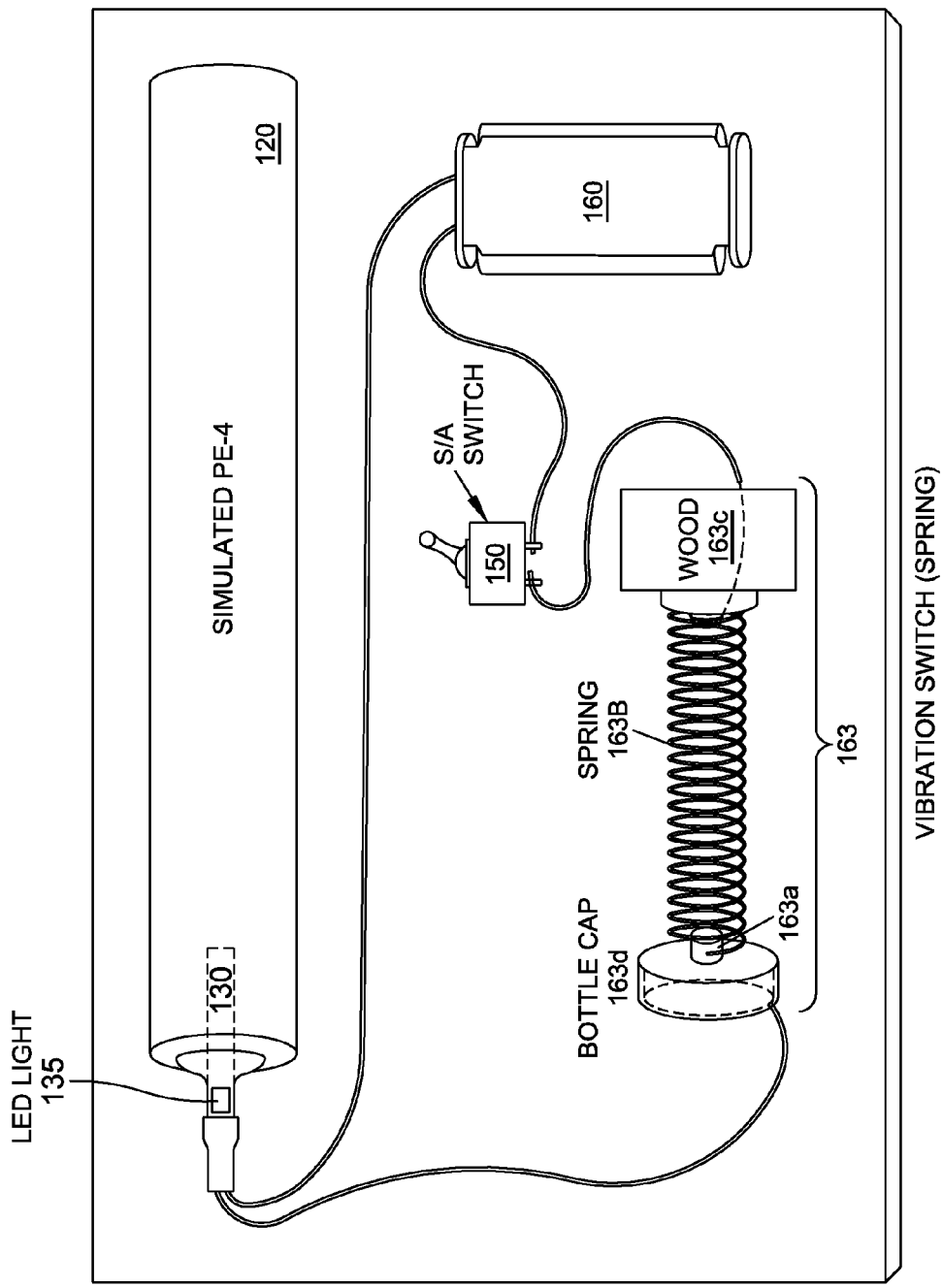
FIG. 20 illustrates an embodiment of a simulated IED Circuit Kit.

In FIG. 20, the trigger switch is a vibration switch 163 which closes a circuit between the power source 160 and the simulated blasting cap 130 upon an electrical contact 163a mounted on a spring 163b coupled to a wooden base 163c contacting an electrically conductive bottle cap 163d responsive to vibration which causes the spring 163b to sway. The base 163c may alternatively be made of a different material, for example, a plastic. The simulant 120 is a simulant for PE-4.

Figure 21:
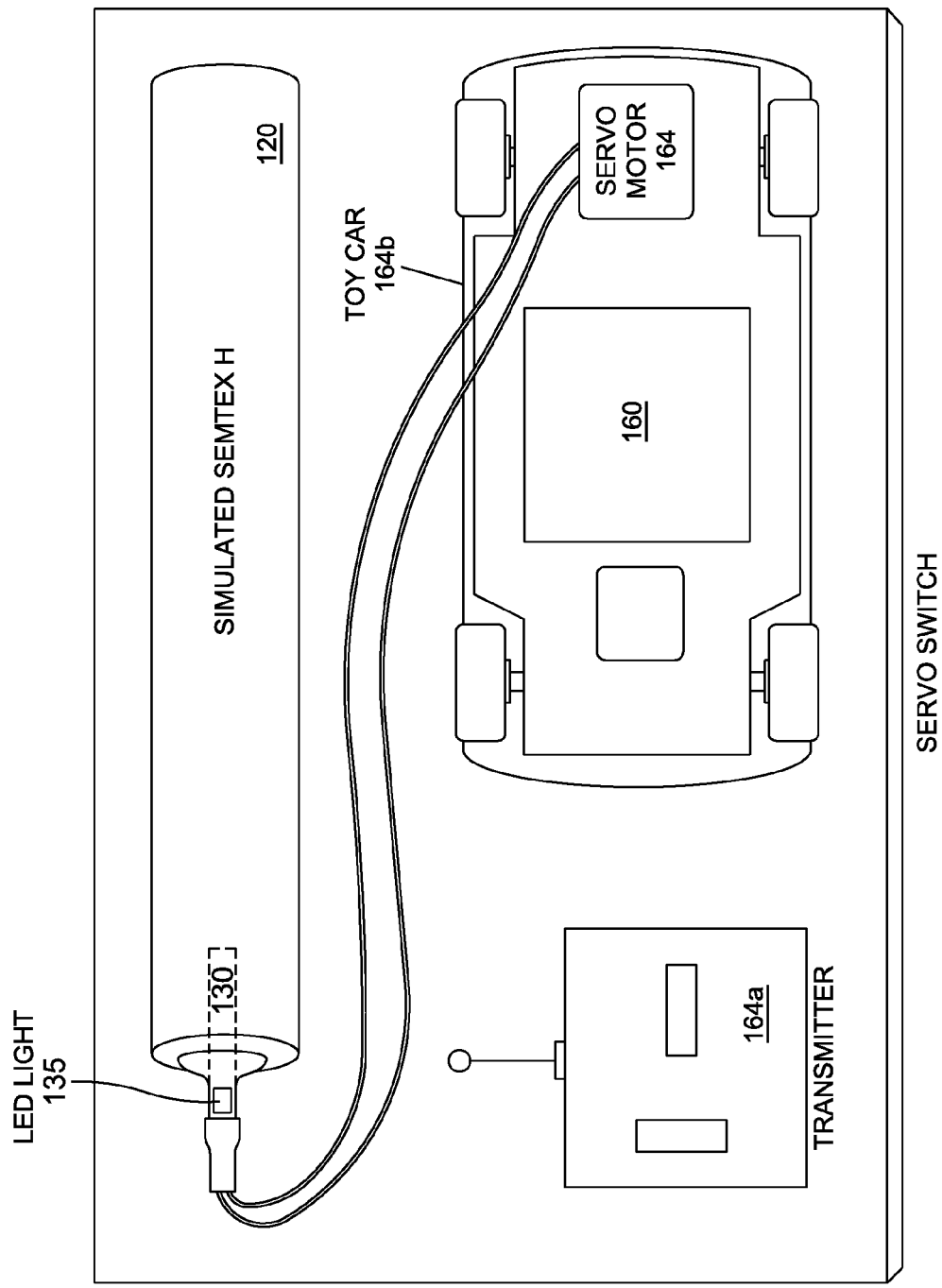
FIG. 21 illustrates an embodiment of a simulated IED Circuit Kit.

In FIG. 21, the trigger switch is a servo motor 164 mounted in, for example, a toy car 164b which closes a circuit between the power source 160 and the simulated blasting cap 130 upon an electrical contact mounted on a portion of the servo motor 164 contacting a second electrical contact mounted on a second portion of the servo motor 164 or within a portion of the toy car 164b. The servo motor 160 may be remotely operated by a wireless transmitter 164a. The simulant 120 is a simulant for Semtex.

Figure 22:
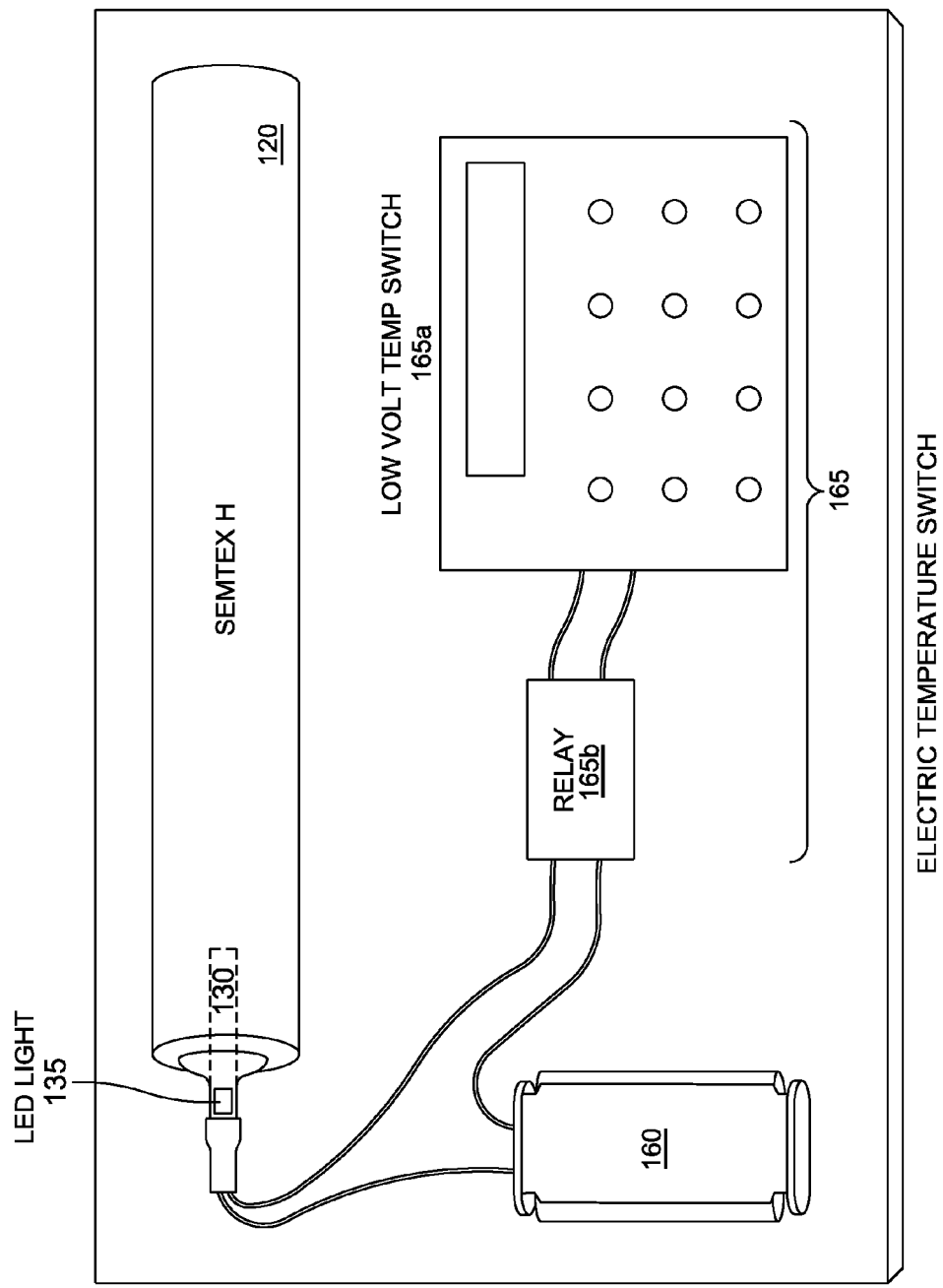
FIG. 22 illustrates an embodiment of a simulated IED Circuit Kit.

In FIG. 22, the trigger switch 165 is a temperature switch 165a and associated relay 165b which closes a circuit between the power source 160 and the simulated blasting cap 130 upon the temperature reaching a set point programmed into the temperature switch 165a. The simulant 120 is a simulant for Semtex.

Figure 23:
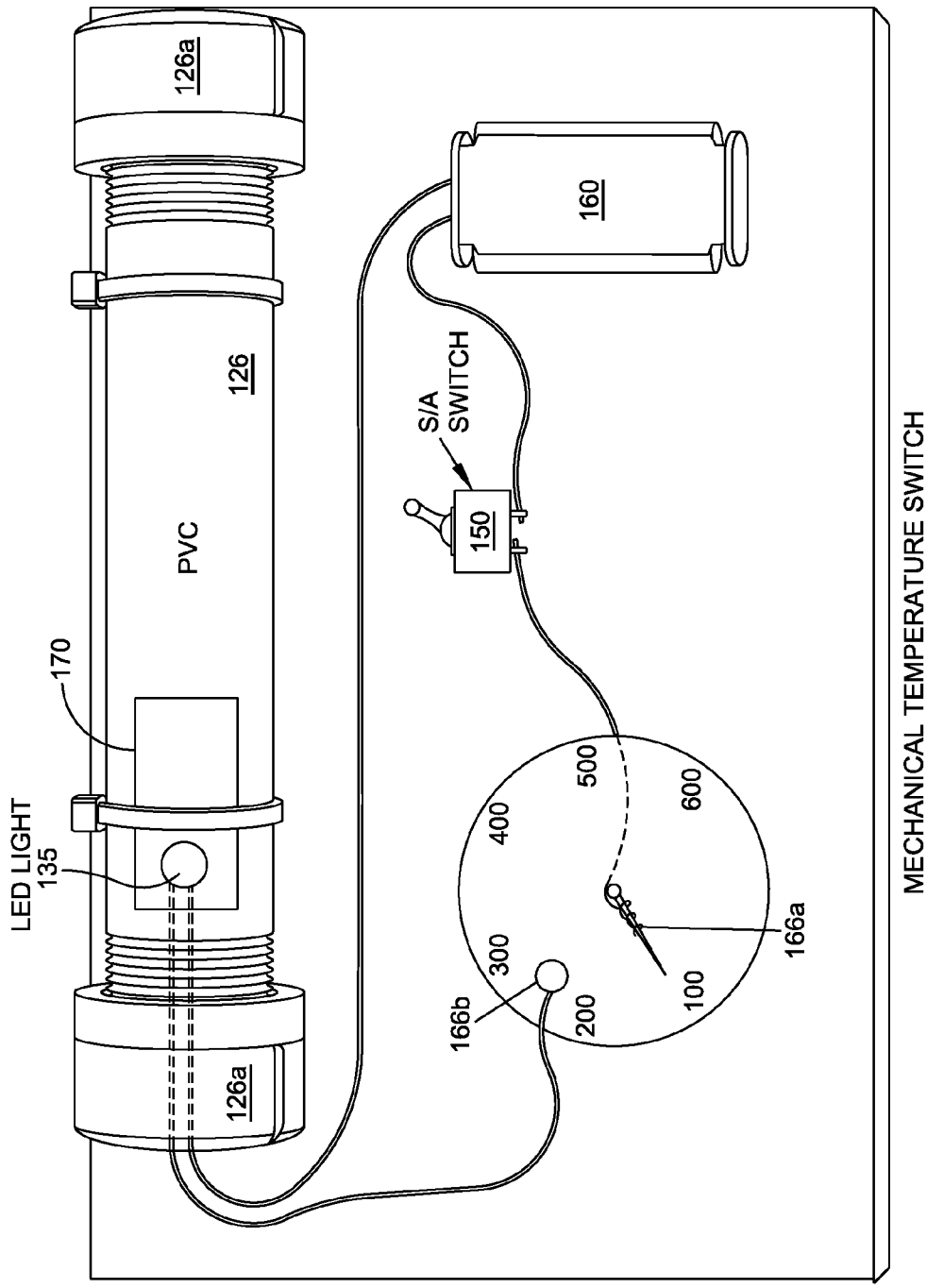
FIG. 23 illustrates an embodiment of a simulated IED Circuit Kit.

In FIG. 23, the trigger switch is an oven temperature switch 166 which closes a circuit between the power source 160 and the simulant upon the temperature reaching a point at which an electrical contact mounted to a hand 166a of the oven temperature switch 166 contacts a second electrical contact 166b mounted on the face of the oven temperature switch. The simulant is packed in a PVC pipe 126 which includes a window 170 through which an indicator light 135 may be viewed. Alternatively, the PVC pipe 126 may be empty.

Figure 24:
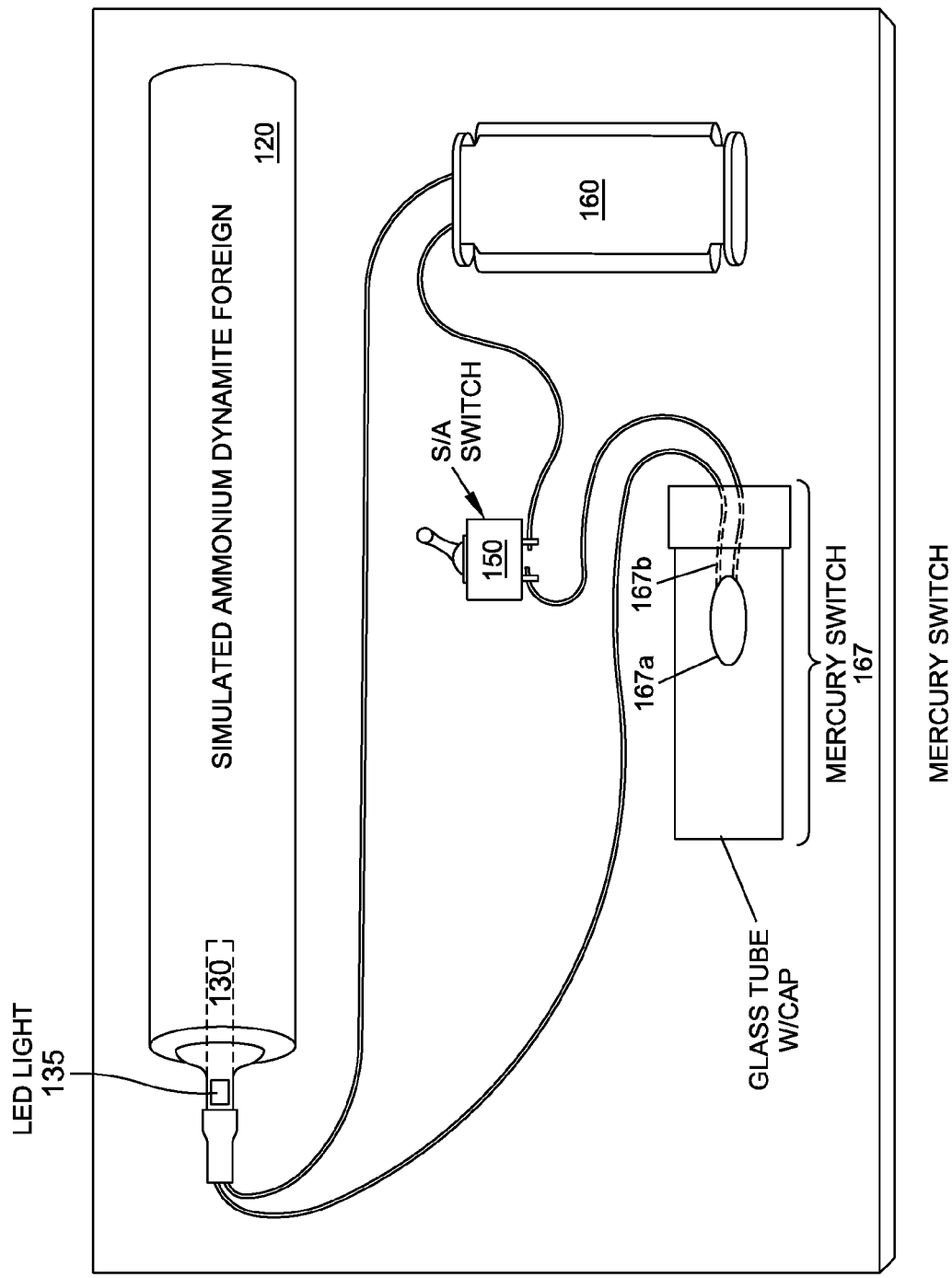
FIG. 24 illustrates an embodiment of a simulated IED Circuit Kit.

In FIG. 24, the trigger switch is a mercury switch 167 which closes a circuit between the power source 160 and the simulated blasting cap 130 upon tilting of the switch so that a drop of mercury 167a rolls into contact with a pair of electrical contacts 167b within the switch 167. The simulant 120 is a simulant for ammonium dynamite.

Figure 25:
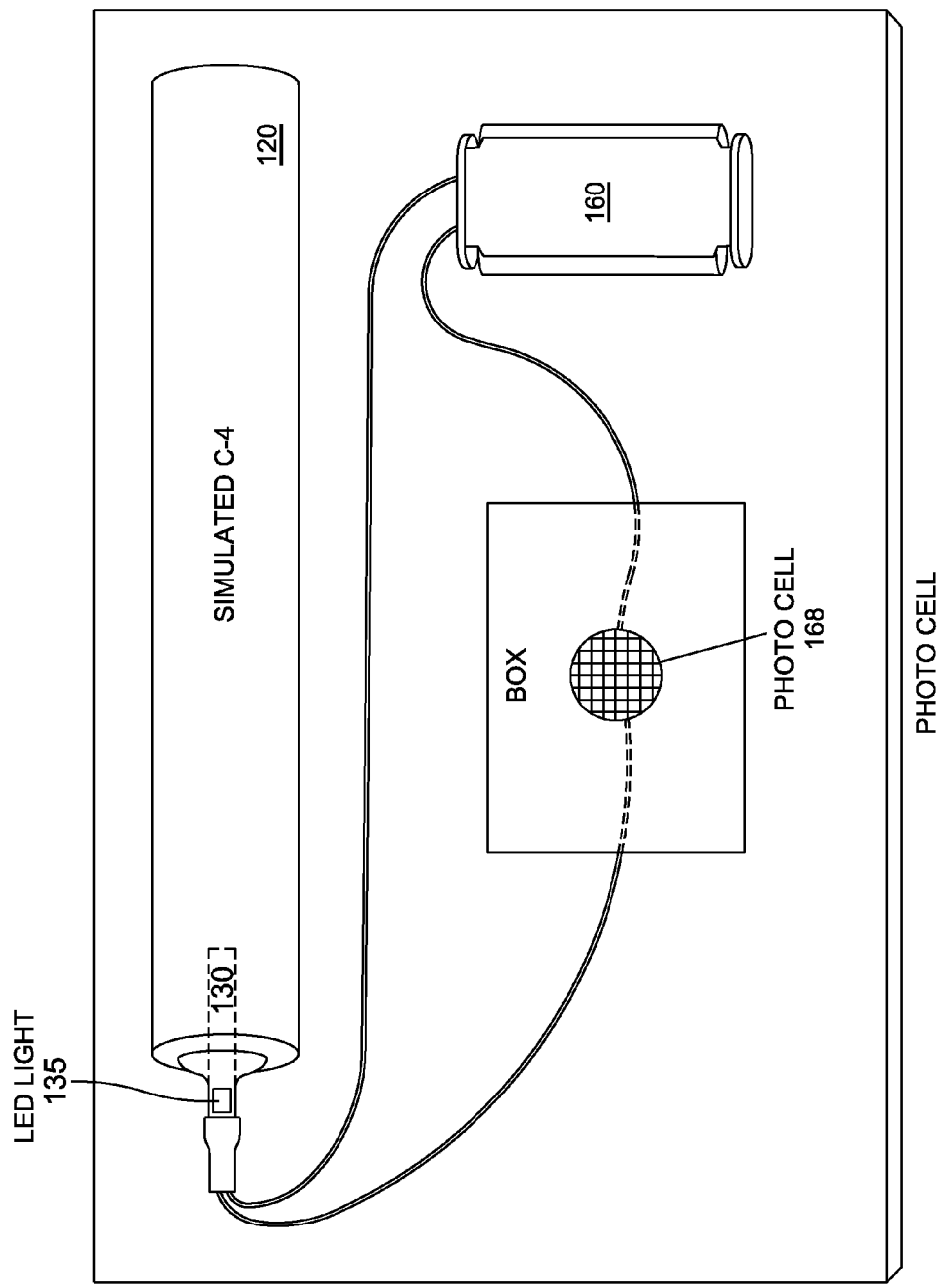
FIG. 25 illustrates an embodiment of a simulated IED Circuit Kit.

In FIG. 25, the trigger switch is a photo cell 168 which closes a circuit between the power source 160 and the simulated blasting cap 130 upon exposure of the photo cell 168 to light. The simulant 120 is a simulant for C-4 explosive.

Figure 26:
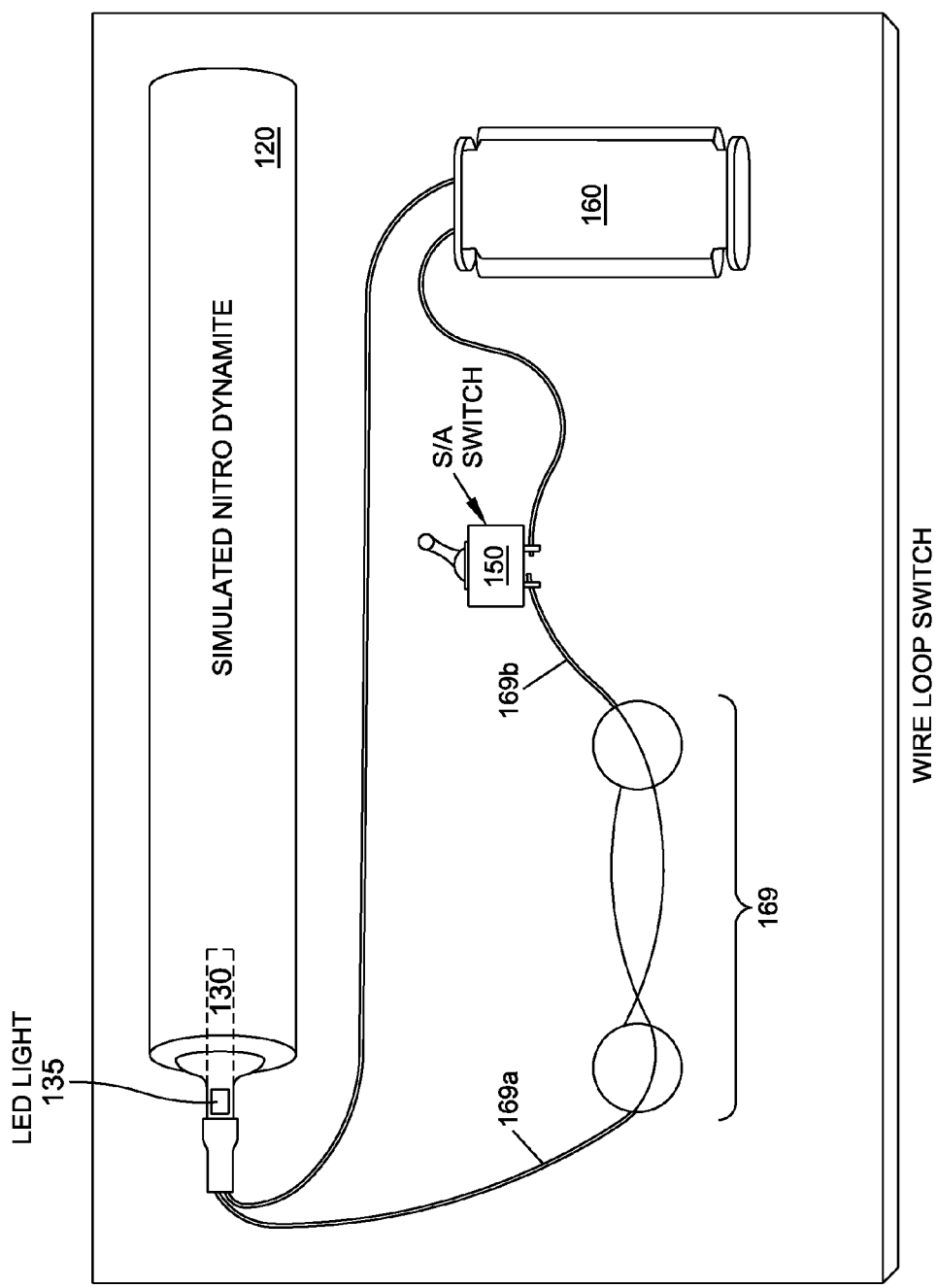
FIG. 26 illustrates an embodiment of a simulated IED Circuit Kit.

In FIG. 26, the trigger switch is a wire loop switch 169. A first exposed wire 169a passes through a loop in a second exposed wire 169b. The second exposed wire 169b passes through a loop in the first exposed wire 169a. The circuit between the power source 160 and the simulated blasting cap 130 is closed upon vibration or displacement of one of the wires 169a, 169b which brings the wire in contact with the loop of the other wire 169a, 169b. The simulant 120 is a simulant for nitro dynamite.

Figure 27:
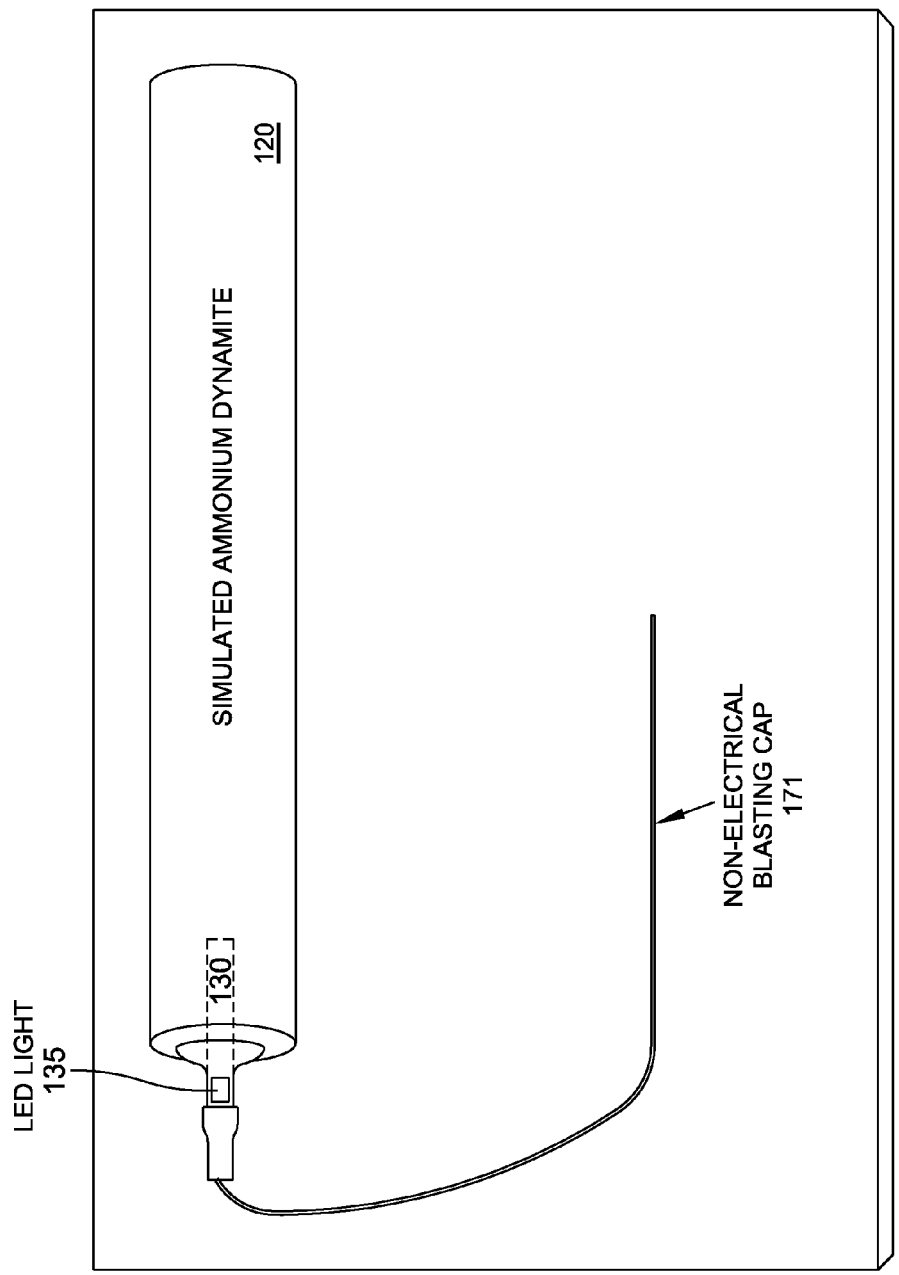
FIG. 27 illustrates an embodiment of a simulated IED Circuit Kit.

In FIG. 27, the trigger switch is a non-electrical blasting cap 171, for example, det. cord. The simulant 120 is a simulant for ammonium dynamite.

In accordance with another broad aspect disclosed herein, there is provided embodiments of simulated blasting caps. The simulated blasting caps are designed to look and feel substantially similar to actual "live" blasting caps and are constructed from materials which provide a substantially similar X-ray signature as actual "live" blasting caps.

Figure 28:
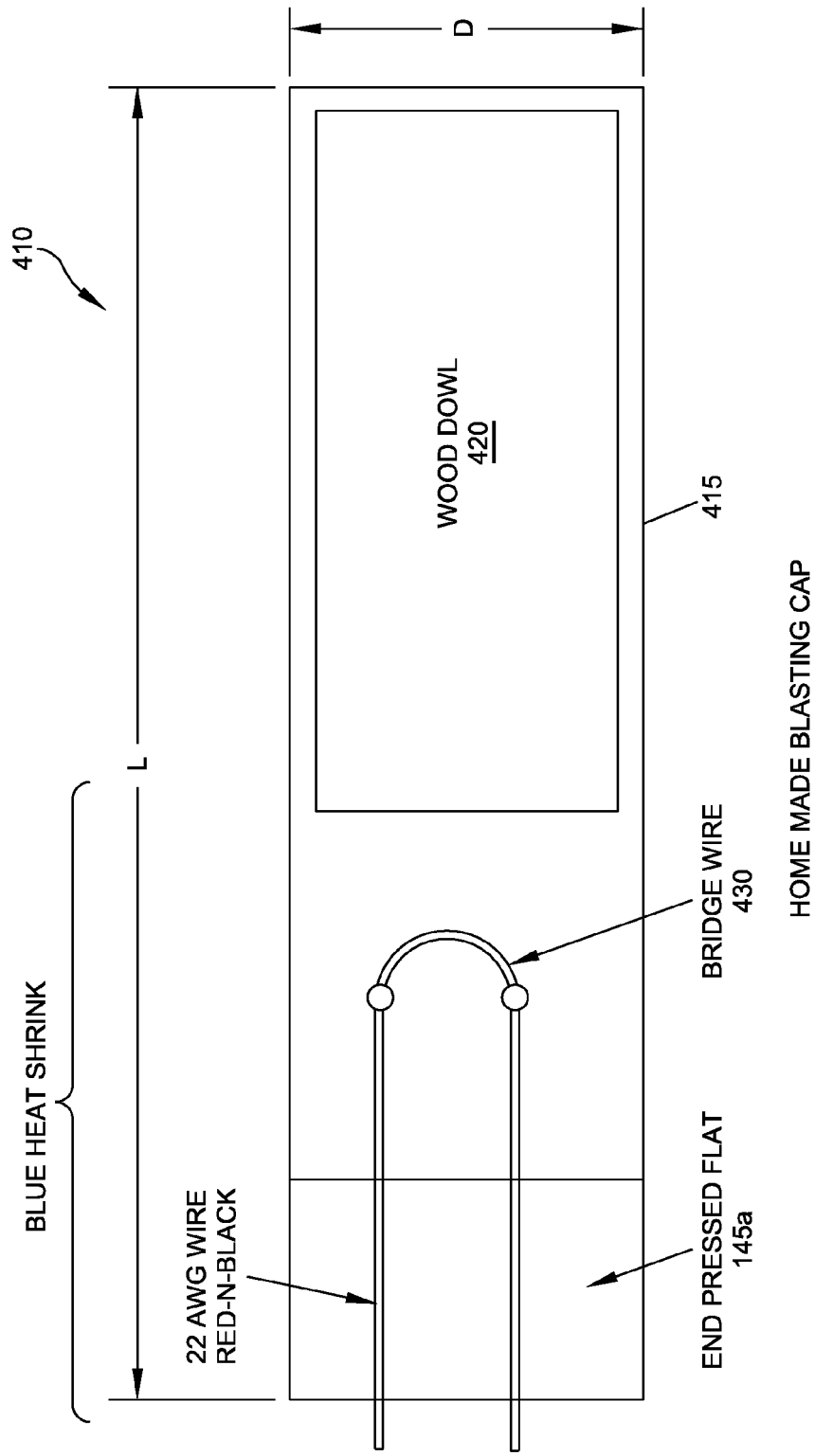
FIG. 28 illustrates an embodiment of a simulated blasting cap.

FIG. 28 illustrates a simulated homemade blasting cap 410. The simulated homemade blasting cap 410 includes a copper tube 415 having a length L of about 2.25 inches and a diameter D of about 0.25 inches. A wooden dowel or a polymer rod such as PTFE 420 having a length of about two inches which simulates an explosive, for example, PETN, is disposed within the copper tube 415 and secured therein with, for example, an adhesive such as glue. An end 415a of the copper tube 415 is pressed flat and retains a bridge wire 430. In some embodiments the bridge wire 430 may be simulated by a portion of a small incandescent light bulb.

Figure 29:
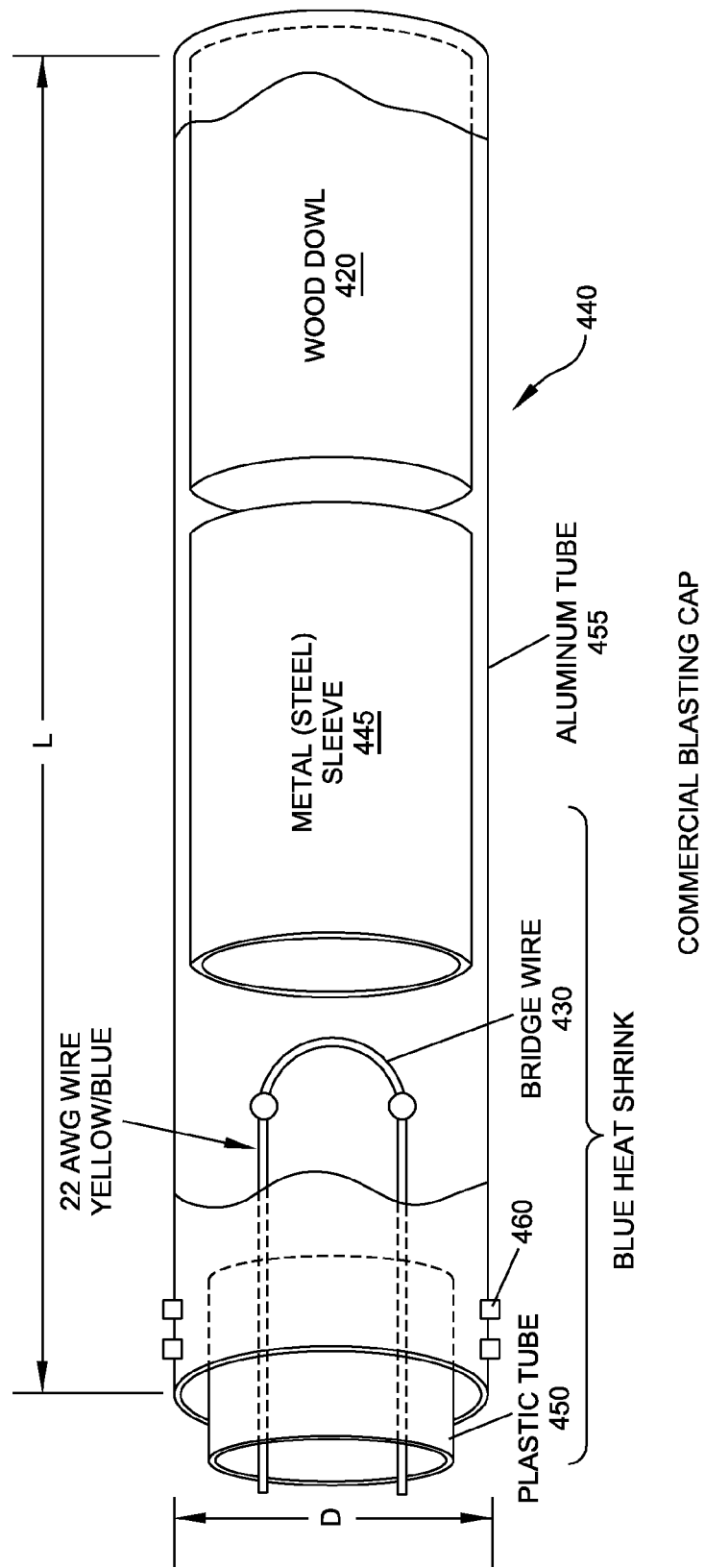
FIG. 29 illustrates an embodiment of a simulated blasting cap.

FIG. 29 illustrates a simulated commercial blasting cap 440. The simulated commercial blasting cap 440 includes an aluminum tube 455 having a length L of about 2.25 inches and a diameter D of about 0.25 inches. A wooden dowel or a polymer rod such as PTFE 420 having a length of about one inch which simulates an explosive, for example, PETN, is disposed within the aluminum tube 455 and secured therein with, for example, an adhesive such as glue. A metal sleeve 445 is also disposed within the aluminum tube 455 and simulates a protective metal sleeve present in many commercial blasting caps. A bridge wire 430 is disposed within an end of the aluminum tube 455 and may be secured therein by a plastic tube 450 which may be held in place in the aluminum tube 455 by one or more crimps 460.

Figure 30:
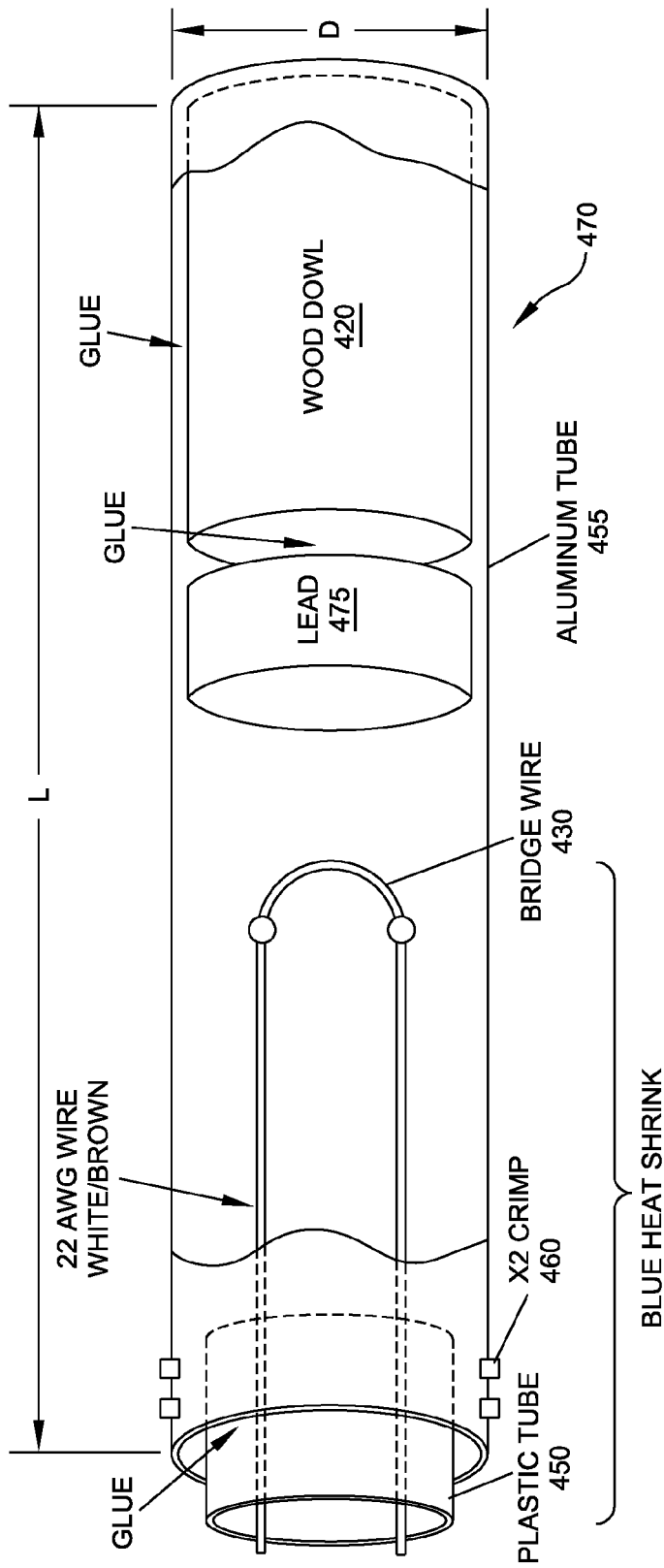
FIG. 30 illustrates an embodiment of a simulated blasting cap.

FIG. 30 illustrates a simulated military blasting cap 470. The simulated military blasting cap 470 includes an aluminum tube 455 having a length L of about 2.25 inches and a diameter D of about 0.25 inches. A wooden dowel or a polymer rod such as PTFE 420 having a length of about 1.25 inches which simulates an explosive, for example, PETN, is disposed within the aluminum tube 455 and secured therein with, for example, an adhesive such as glue. A lead wire 475 having a length of, for example, about 0.25 inches is also disposed within the aluminum tube 455 and simulates a lead azide charge present in many military blasting caps. A bridge wire 430 is disposed within an end of the aluminum tube 455 and may be secured therein by a plastic tube 450 which may be held in place in the aluminum tube 455 by one or more crimps 460.

Figure 31:
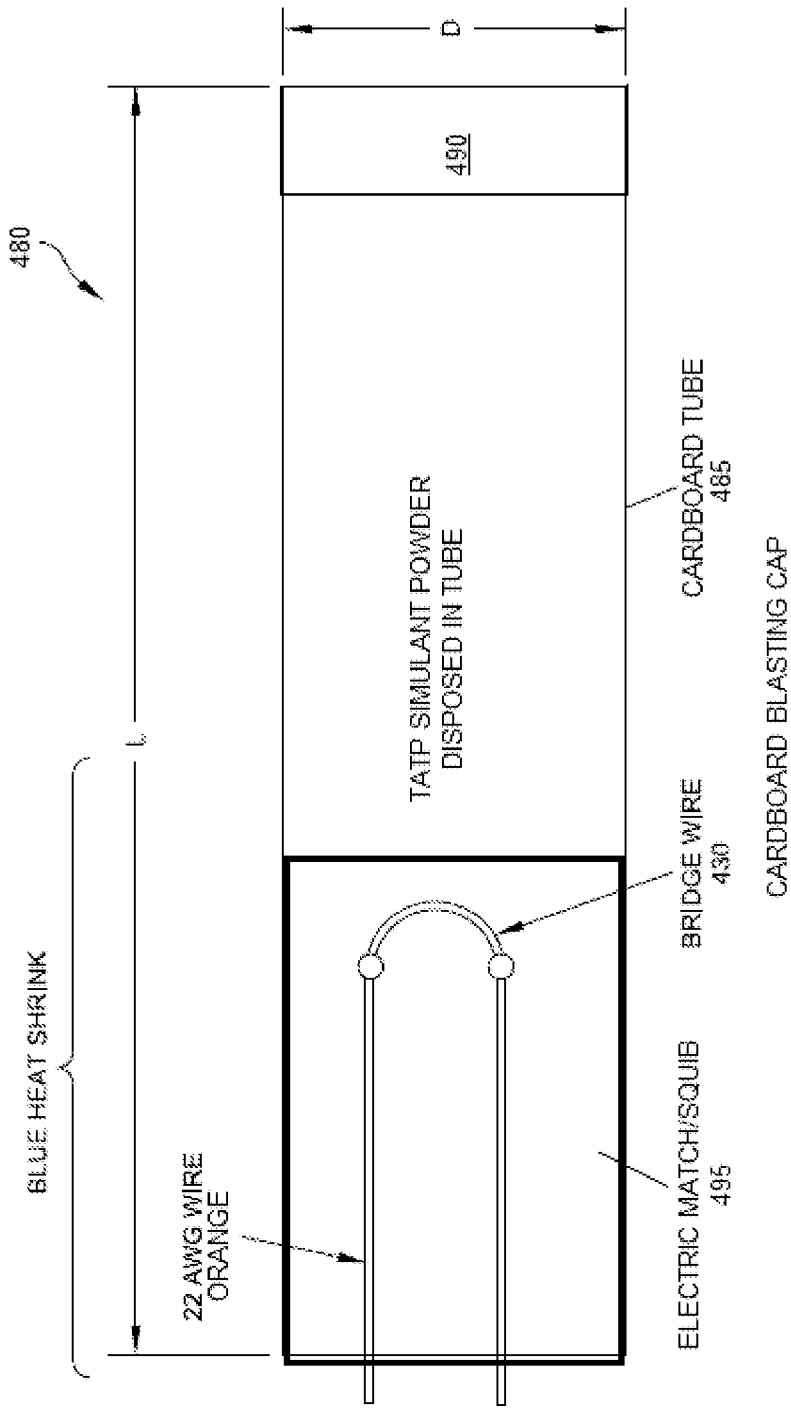
FIG. 31 illustrates an embodiment of a simulated blasting cap.

FIG. 31 illustrates a simulated cardboard blasting cap 480. The simulated cardboard blasting cap 480 includes a cardboard tube 485 having a length L of about 2.00 inches and a diameter D of about 0.25 inches. Powdered sugar which simulates an explosive, for example, TATP, is disposed within the cardboard tube 485 and secured therein with, for example, a cardboard cap 490 and adhesive such as glue. An electric match 495 is disposed within an end of the cardboard tube 485 and may be secured in the cardboard tube 485 by adhesive or heat shrink.

In accordance with another broad aspect disclosed herein, there is provided embodiments of various Threat Screening Kits. The Threat Screening Kits are designed to mimic the look and feel of "live" explosive devices or components thereof and to provide a substantially similar X-ray signature as actual "live" explosive devices.

Figure 32:
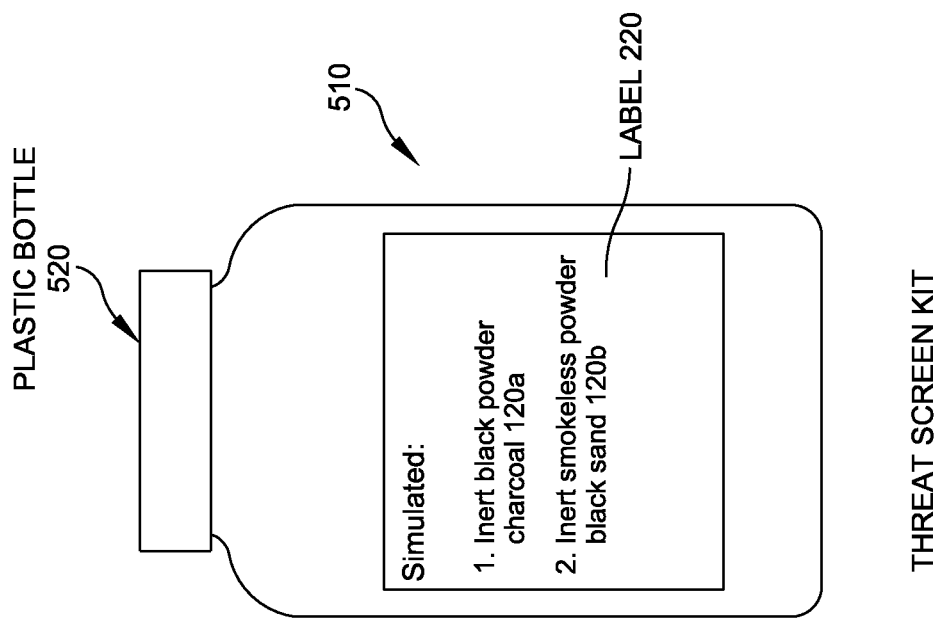
FIG. 32 illustrates an embodiment of a Threat Screening Kit.

A first Threat Screening Kit 510, illustrated in FIG. 32, includes a plastic bottle 520, which is at least partially filled with an explosive simulant, for example, black sand 120a to simulate black powder or charcoal 120b to simulate smokeless powder. The plastic bottle 520 may include a label 220 identifying the explosive being simulated and indicating that the simulant is inert. The label 220 may be similar to one of those illustrated in FIGS. 3A-3C.

Figure 33:
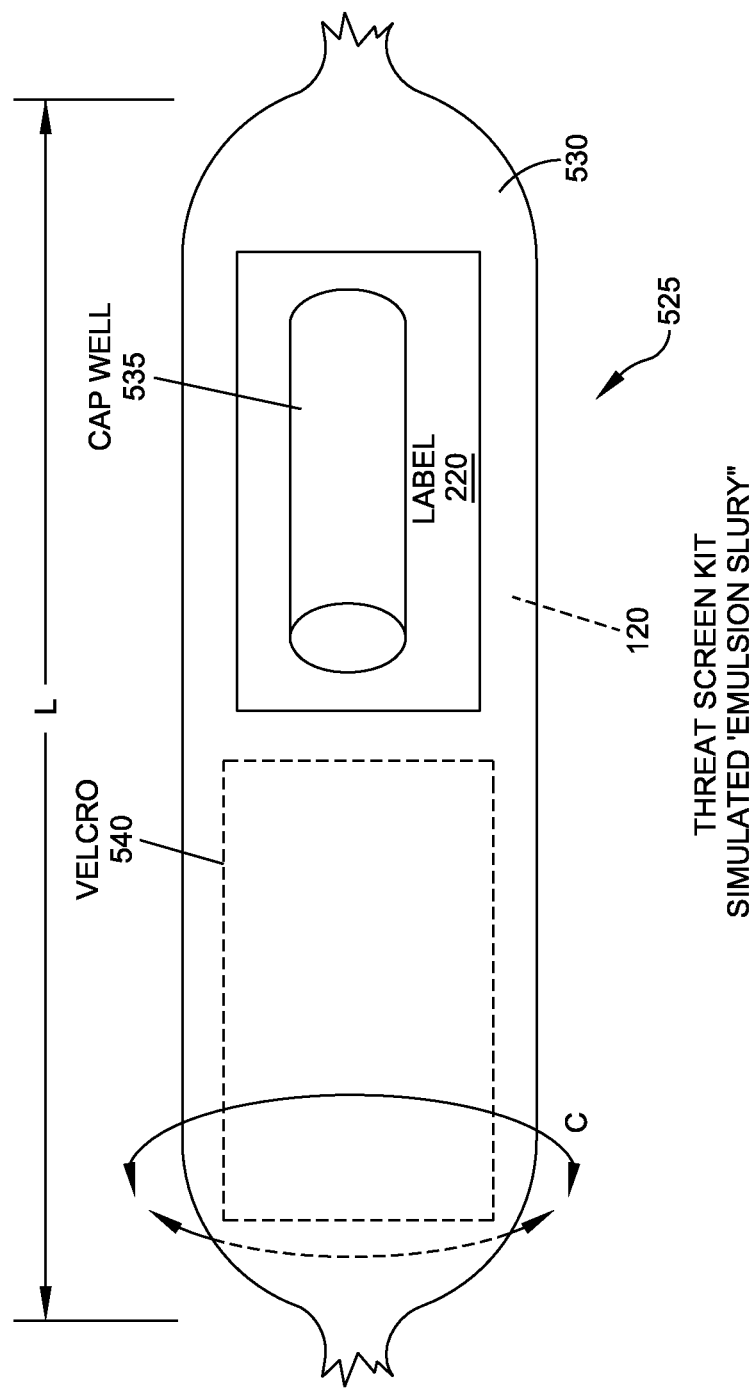
FIG. 33 illustrates an embodiment of a Threat Screening Kit.

Another Threat Screening Kit 525, illustrated in FIG. 33, may include a simulated emulsion or slurry type explosive simulant 120 packaged within a substantially cylindrical vessel 530 which may be constructed of, for example, a metal, plastic, or a flexible rubber material. The vessel 530 may have a length L of, for example, about eight inches and a circumference C of about six inches. The vessel 530 may include a label 220 identifying the explosive being simulated and indicating that the simulant is inert. The label 220 may be similar to one of those illustrated in FIGS. 3A-3C. The vessel 530 may also include a cap well 535 inserted into a portion thereof or mounted on a surface thereof to house a simulated blasting cap and may include a fastener 540, for example, a sheet of VELCRO® hook and loop fastener to facilitate attaching the vessel to a substrate board 110 of a simulated IED Circuit Kit 100.

Figure 34:
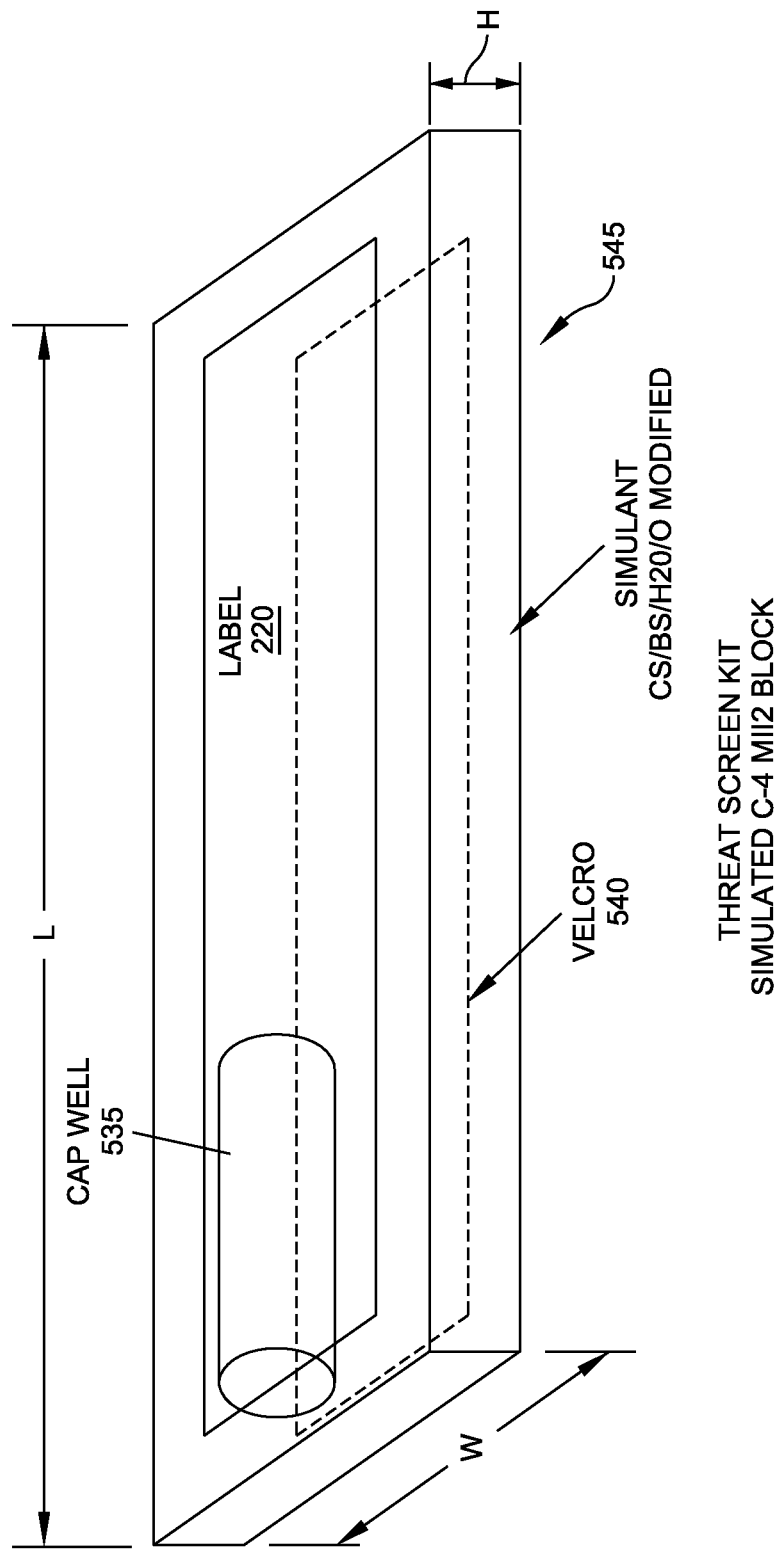
FIG. 34 illustrates an embodiment of a Threat Screening Kit.

FIG. 34 illustrates another Threat Screening Kit 545 which simulates a block of C-4 explosive. The simulant used may be a mixture of corn syrup, baking soda, water, vegetable oil, and paraffin wax packaged in paper or plastic film. The simulated block of C-4 545 may have a length L of about 11 inches, a width W of about two inches, and a height H of about one inch, which is consistent with conventional packaging of actual C-4 explosive blocks. The simulated block of C-4 545 may include a label 220 identifying the explosive being simulated and indicating that the simulant is inert. The label 220 may be similar to one of those illustrated in FIGS. 3A-3C. The simulated block of C-4 545 may also include a cap well 535 inserted into a portion thereof or mounted on a surface thereof to house a simulated blasting cap and may include a fastener 540, for example, a sheet of VELCRO® hook and loop fastener to facilitate attaching the simulated block of C-4 545 to a substrate board 110 of a simulated IED Circuit Kit 100.

Figure 35:
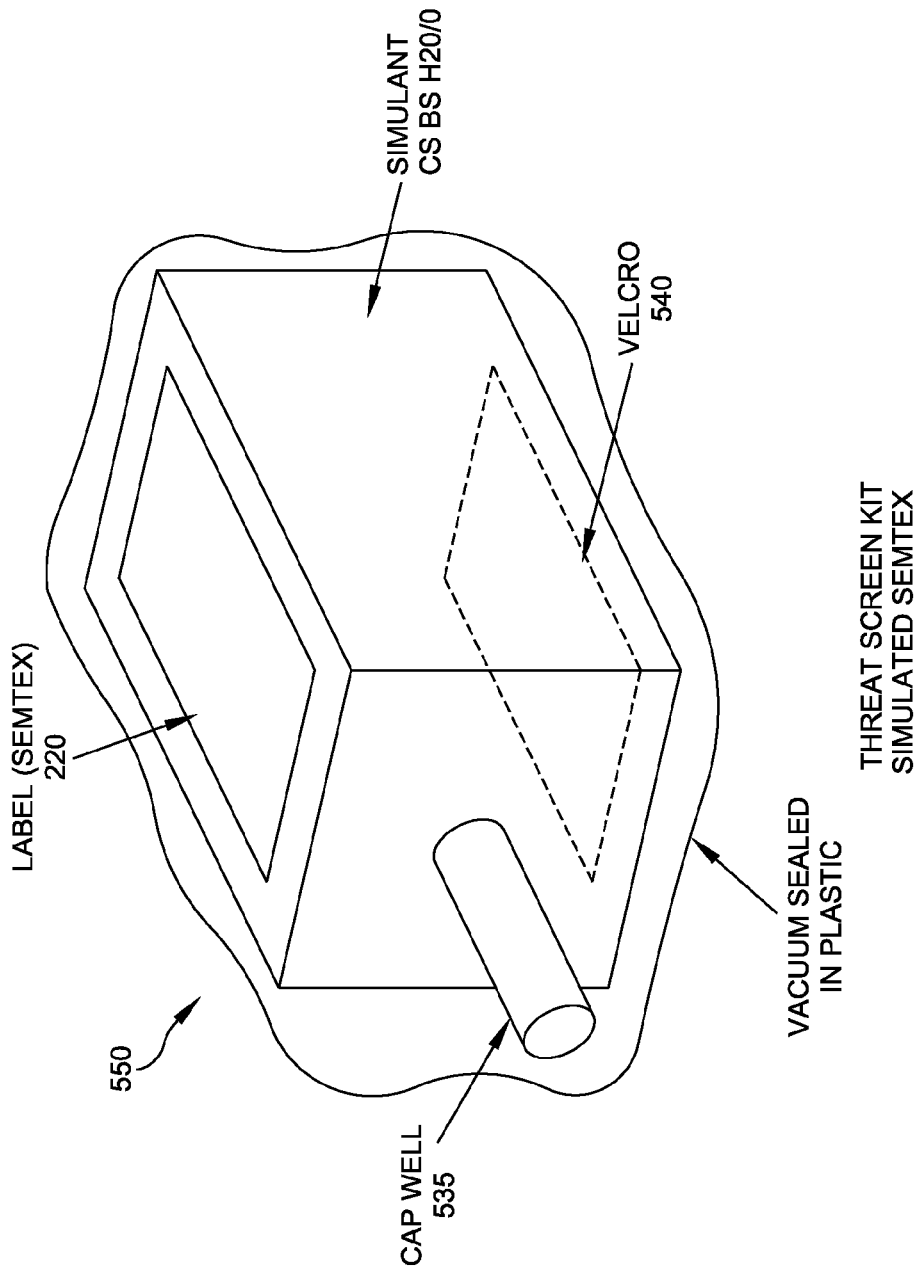
FIG. 35 illustrates an embodiment of a Threat Screening Kit.

FIG. 35 illustrates another Threat Screening Kit 550 which simulates a block of Semtex explosive. The simulant used may be a mixture of corn syrup, baking soda, water, and oil vacuum packaged in plastic film. The simulated block of Semtex explosive 550 may have a length of about three inches, a width of about three inches, and a height of about three inches, which is consistent with conventional packaging of actual Semtex explosive blocks. The simulated block of Semtex 550 may include a label 220 identifying the explosive being simulated and indicating that the simulant is inert. The label 220 may be similar to one of those illustrated in FIGS. 3A-3C. The simulated block of Semtex 550 may also include a cap well 535 inserted into a portion thereof or mounted on a surface thereof to house a simulated blasting cap and may include a fastener 540, for example, a sheet of VELCRO® hook and loop fastener to facilitate attaching the simulated block of Semtex to a substrate board 110 of a simulated IED Circuit Kit 100.

Figure 36:
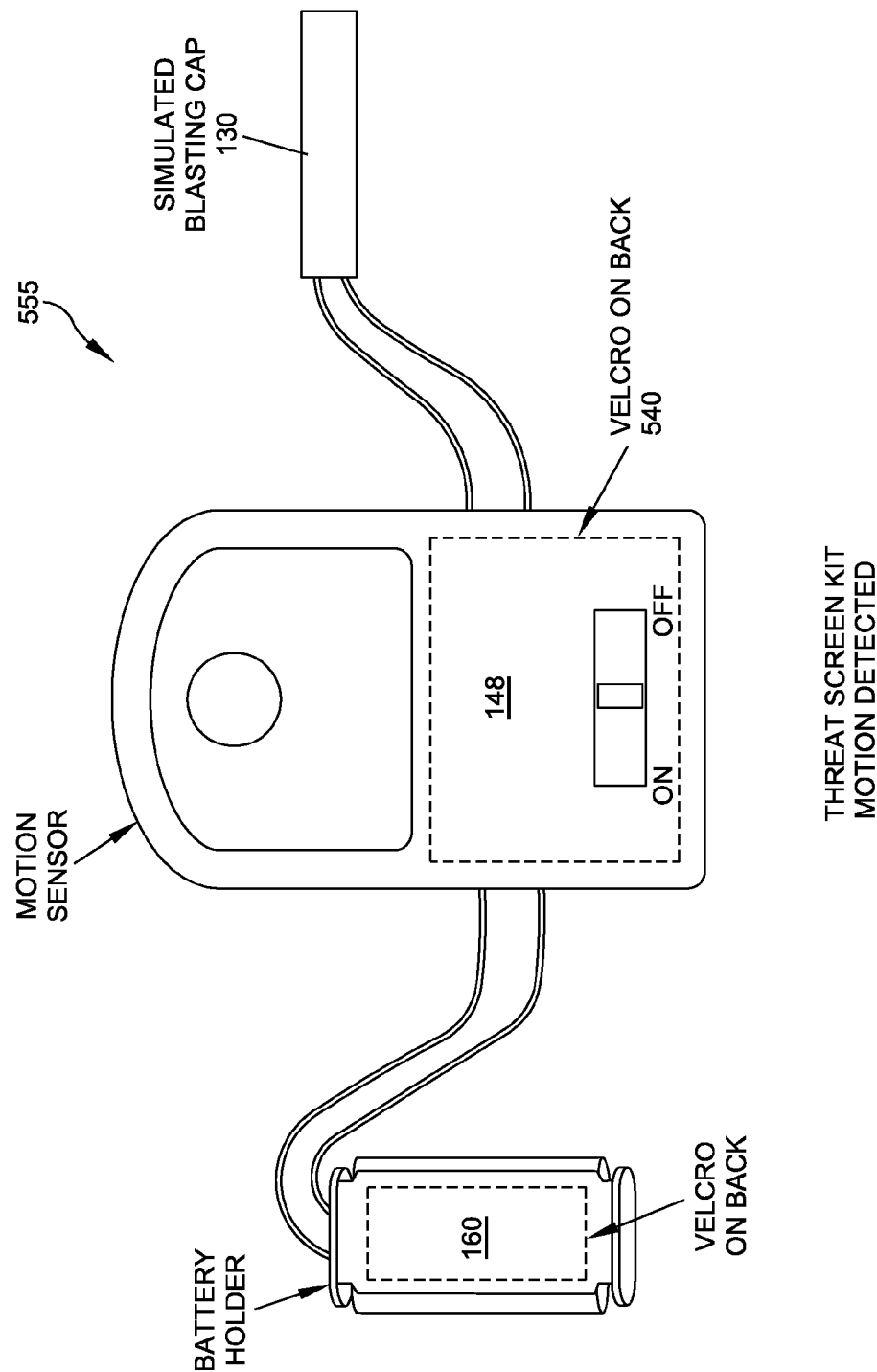
FIG. 36 illustrates an embodiment of a Threat Screening Kit.

FIG. 36 illustrates another Threat Screening Kit 555 which includes a motion activated sensor 145 coupled to a power source 160, for example, a battery pack and to a simulated blasting cap 130. The motion activated sensor 145 may include a fastener 540, for example, a sheet of VELCRO® hook and loop fastener to facilitate attaching the motion activated sensor 145 to a substrate board 110 of a simulated IED Circuit Kit 100. The components of the Threat Screening Kit 555 may be substantially similar to those included in the simulated IED Circuit Kit 100 illustrated in FIG. 7.

Figure 37:
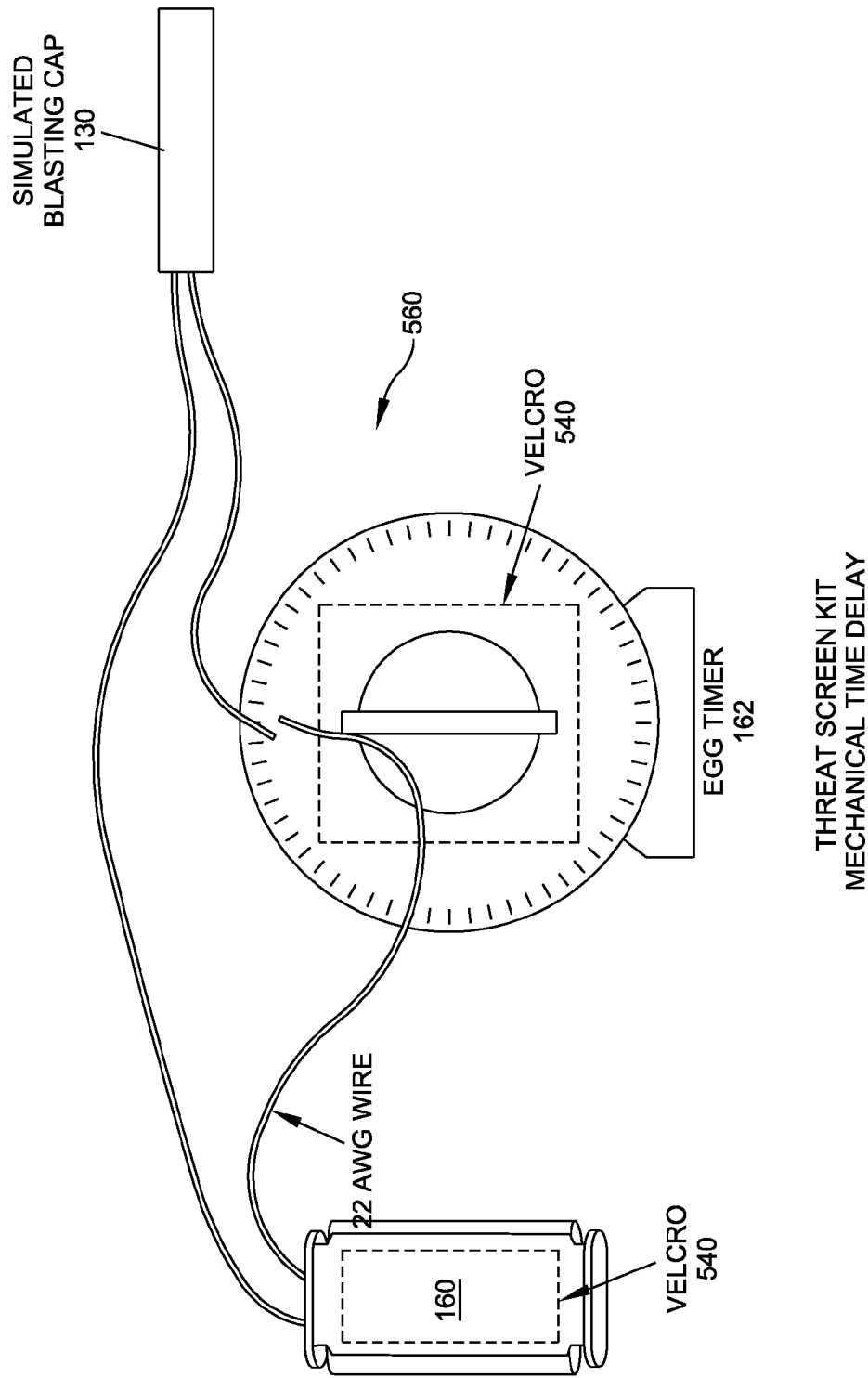
FIG. 37 illustrates an embodiment of a Threat Screening Kit.

FIG. 37 illustrates another Threat Screening Kit 560 which includes a mechanical timer 162 coupled to a power source 160, for example, a battery pack and to a simulated blasting cap 130. The mechanical timer 162 and/or power source 160 may include a fastener 540, for example, a sheet of VELCRO® hook and loop fastener to facilitate attaching the components to a substrate board 110 of a simulated IED Circuit Kit 100. The components of the Threat Screening Kit 560 may be substantially similar to those included in the simulated IED Circuit Kit 100 illustrated in FIG. 19.

Figure 38:
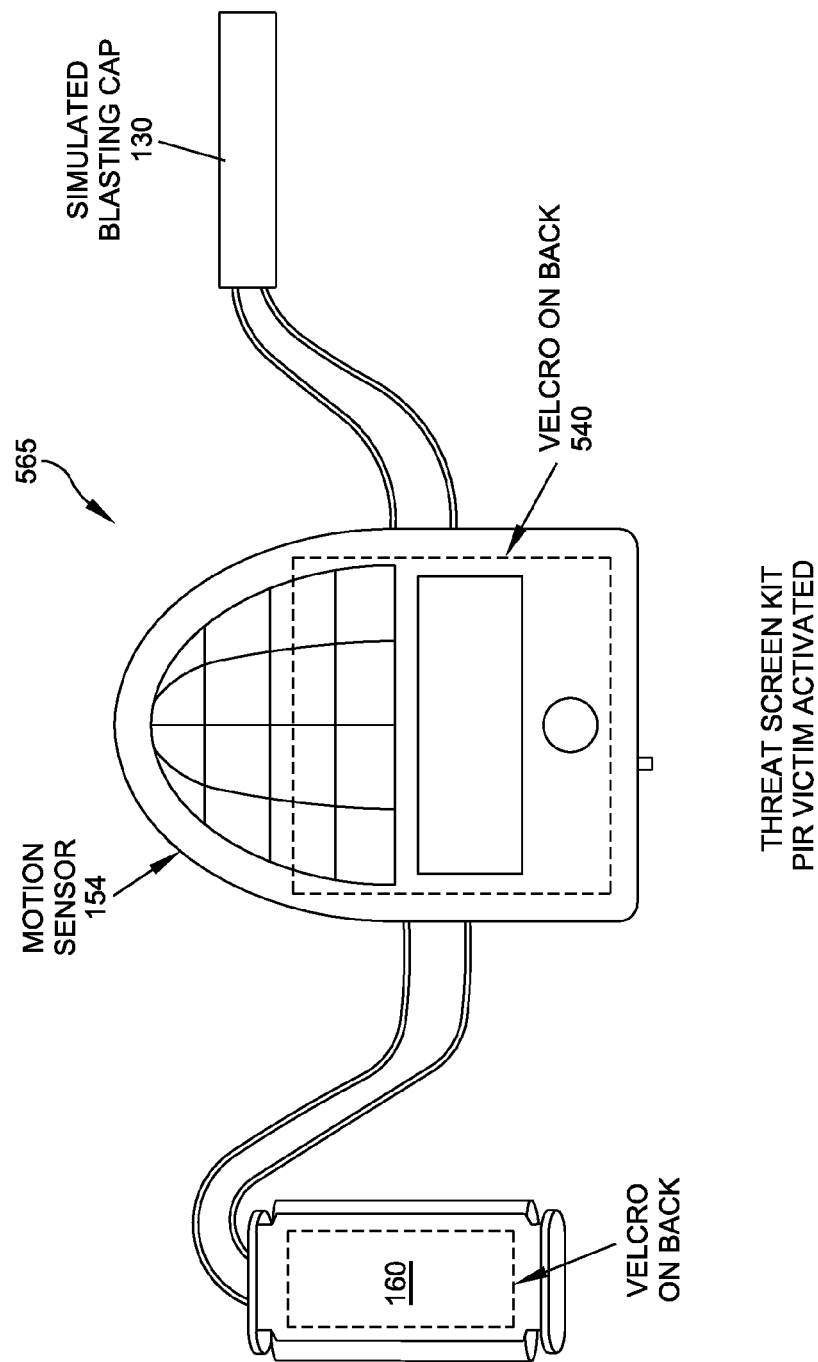
FIG. 38 illustrates an embodiment of a Threat Screening Kit.

FIG. 38 illustrates another Threat Screening Kit 565 which includes a PIR motion sensor 154 coupled to a power source 160, for example, a battery pack and to a simulated blasting cap 130. The PIR motion sensor 154 and/or power source 160 may include a fastener 540, for example, a sheet of VELCRO® hook and loop fastener to facilitate attaching the components to a substrate board 110 of a simulated IED Circuit Kit 100. The components of the Threat Screening Kit 565 may be substantially similar to those included in the simulated IED Circuit Kit 100 illustrated in FIG. 12.

Figure 39:
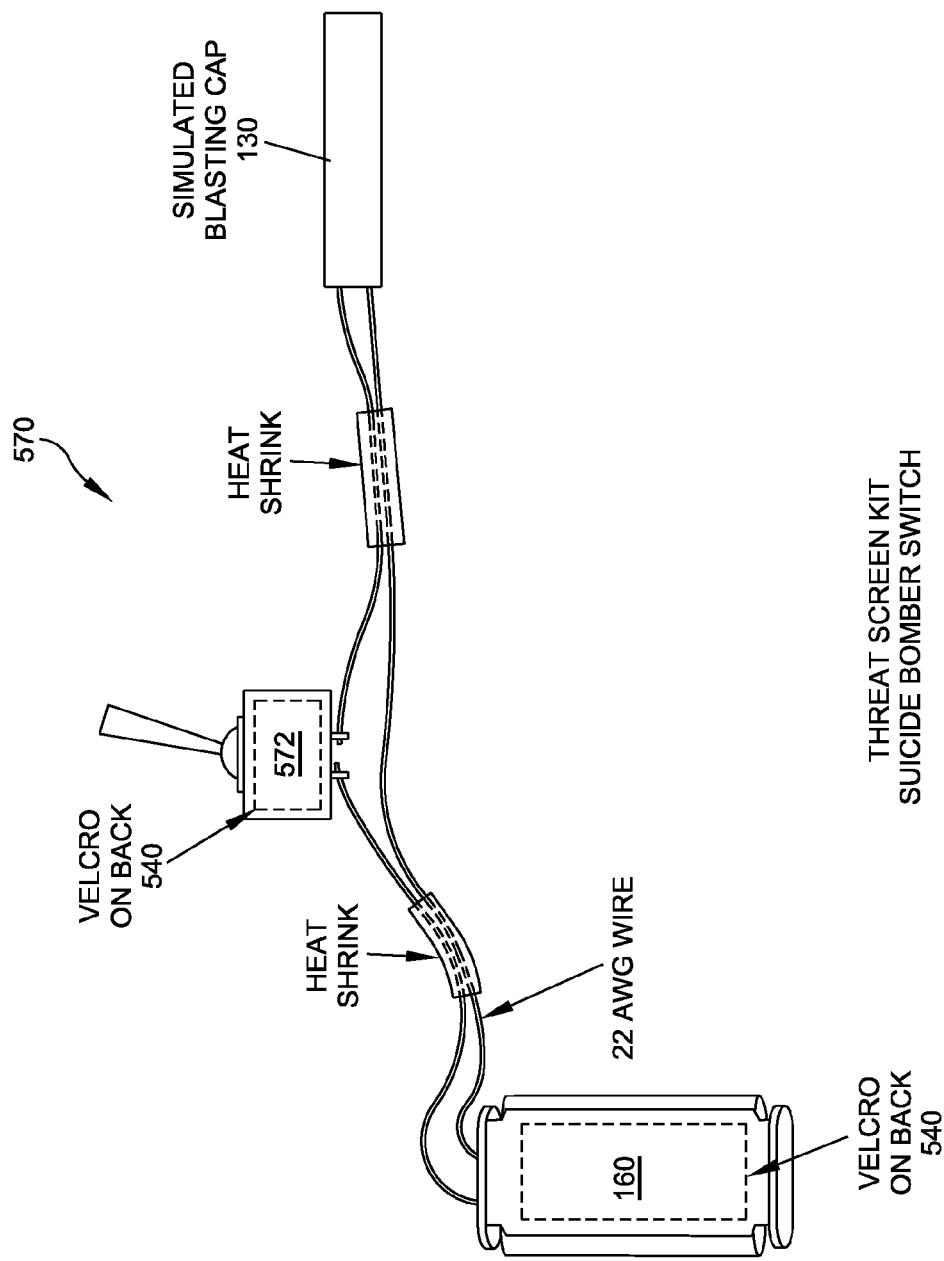
FIG. 39 illustrates an embodiment of a Threat Screening Kit.

FIG. 39 illustrates another Threat Screening Kit 570 which includes a switch 572, for example, a toggle switch coupled to a power source 160, for example, a battery pack and to a simulated blasting cap 130. The switch 572 and/or power source 160 may include a fastener 540, for example, a sheet of VELCRO® hook and loop fastener to facilitate attaching the components to a substrate board 110 of a simulated IED Circuit Kit 100.

Figure 40:
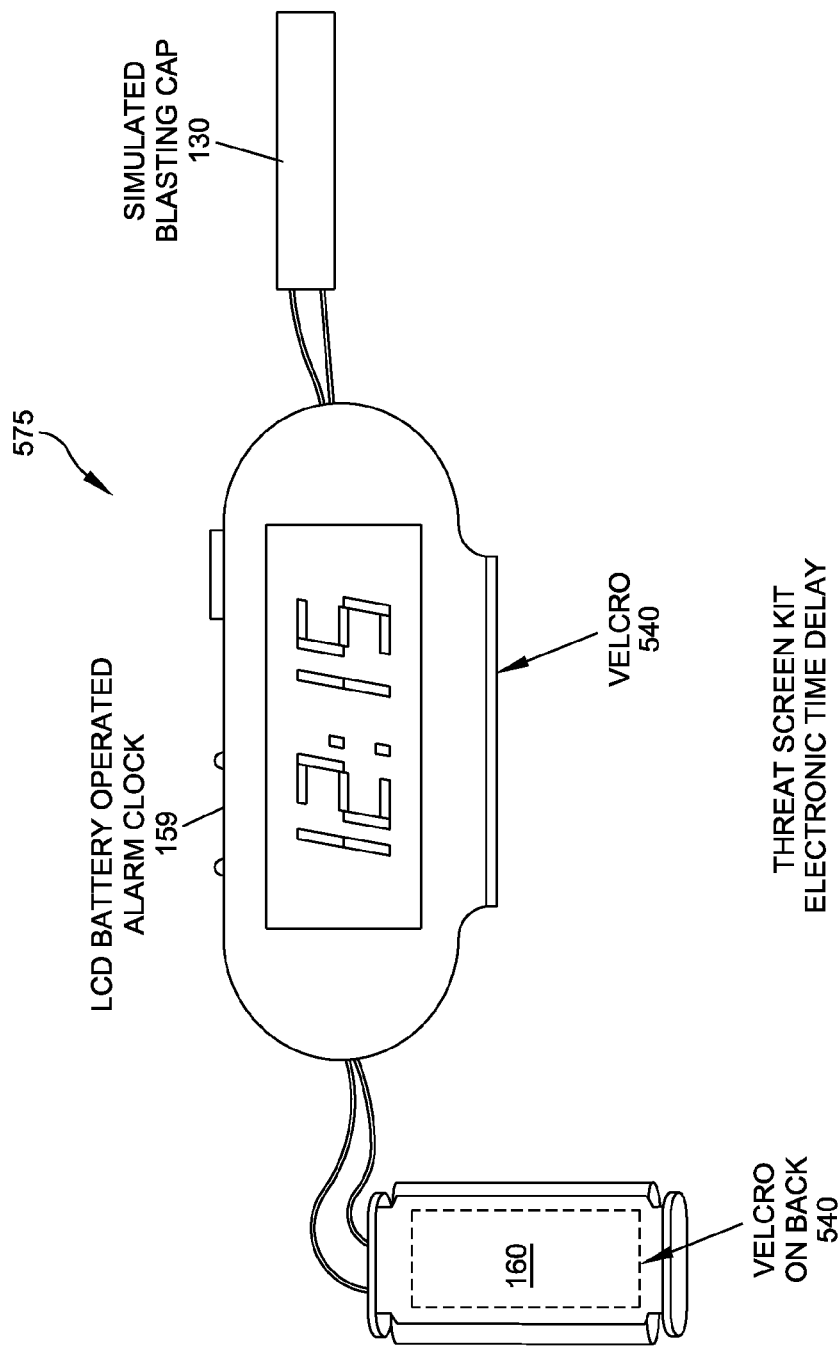
FIG. 40 illustrates an embodiment of a Threat Screening Kit.

FIG. 40 illustrates another Threat Screening Kit 575 which includes a modified battery operated digital alarm clock 159, for example, an Elgin battery powered LCD alarm clock, coupled to a power source 160, for example, a battery pack and to a simulated blasting cap 130. The alarm clock 159 and/or power source 160 may include a fastener 540, for example, a sheet of VELCRO® hook and loop fastener to facilitate attaching the components to a substrate board 110 of a simulated IED Circuit Kit 100. The components of the Threat Screening Kit 575 may be substantially similar to those included in the simulated IED Circuit Kit 100 illustrated in FIG. 17.

Figure 41:
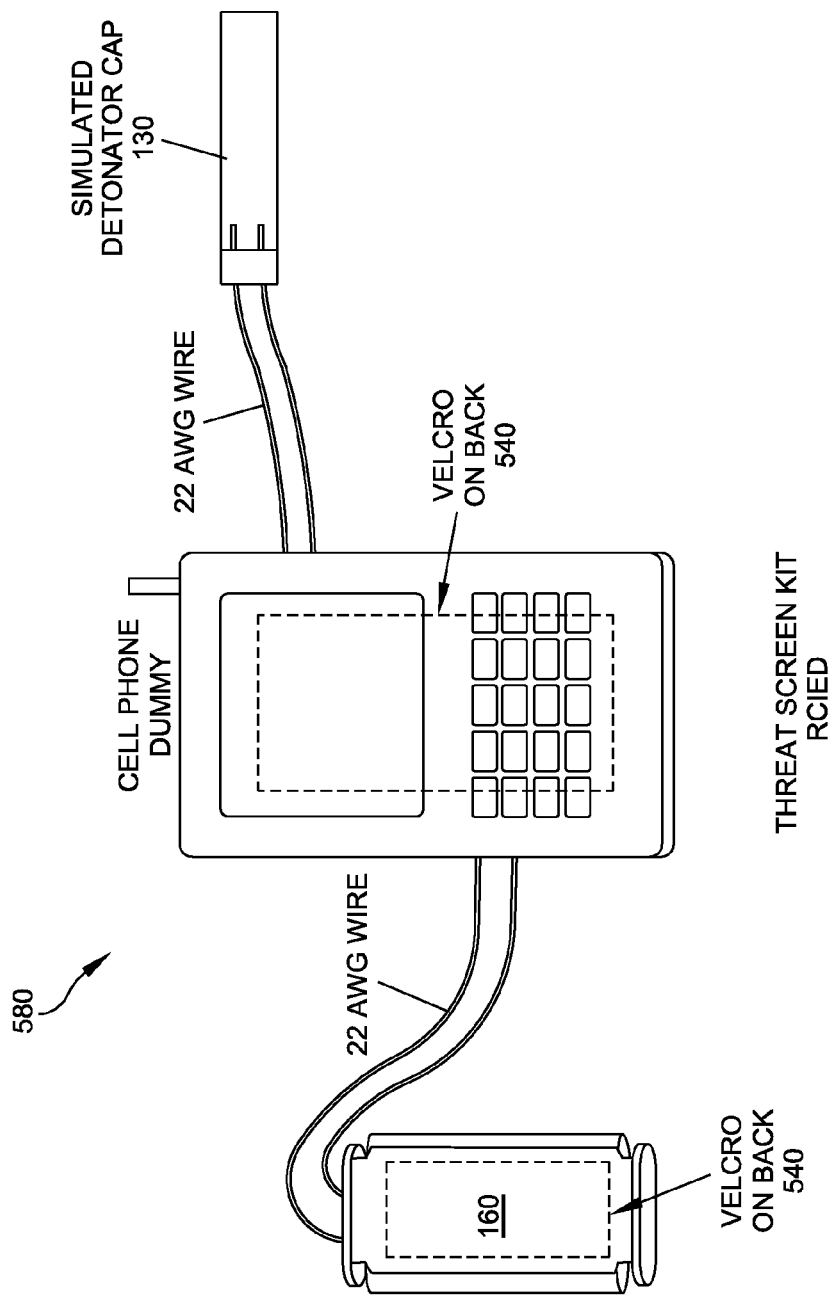
FIG. 41 illustrates an embodiment of a Threat Screening Kit.

FIG. 41 illustrates another Threat Screening Kit 580 which includes a cell phone dummy 151 coupled to a power source 160, for example, a battery pack and to a simulated blasting cap 130. The cell phone dummy 151 and/or power source 160 may include a fastener 540, for example, a sheet of VELCRO® hook and loop fastener to facilitate attaching the components to a substrate board 110 of a simulated IED Circuit Kit 100. The components of the Threat Screening Kit 580 may be substantially similar to those included in the simulated IED Circuit Kit 100 illustrated in FIG. 9.

FIG. 42A illustrates Threat Screening Kit 590a and FIG. 42B illustrates Threat Screening Kit 590b. Threat Screening Kit 590a includes a simulated steel pipe bomb 591 which may have a length of, for example, about six inches or about eight inches and a diameter of, for example, about one inch or about 1.5 inches, and is fitted with end caps 593 which may be screwed onto the ends of the steel pipe bomb 591 and/or glued in place onto the ends of the steel pipe bomb 591. Threat Screening Kit 590b includes a simulated PVC pipe bomb 592 which may have a length of, for example, about eight inches and a diameter of, for example, about 1.25 inches or about two inches, and is fitted with end caps 594 which may be screwed onto the ends of the PVC pipe bomb 592 and/or glued in place onto the ends of the PVC pipe bomb 592. The simulated pipe bombs 591, 592 may include holes 595 for the insertion of simulated blasting caps 130 and may either be filled with an explosive simulant or empty. The simulated pipe bombs 591, 592 may include fasteners 540, for example, sheets of VELCRO® hook and loop fastener to facilitate attaching the components to a substrate board 110 of a simulated IED Circuit Kit 100. The simulated pipe bombs 591, 592 may also include labels 220 which may be similar to one of the labels illustrated in FIGS. 3A-3C. The simulated pipe bombs 591, 592 may also include one or more "inert holes" 596, four of which are illustrated in each of the simulated pipe bombs 591, 592. The inert holes 596 in the simulated pipe bombs 591, 592 make it impossible for somebody to use the simulated pipe bombs 591, 592 as real explosive devices. If a person tried to use the simulated pipe bombs 591, 592 as real devices the holes would allow gasses to escape from the burning explosive material contained therein and thus prevent a mechanical detonation. The inert holes 596 are a safety feature to ensure simulated pipe bombs 591, 592 cannot be used as real explosive devices.

In accordance with another broad aspect disclosed herein, there is provided embodiments of various Mail Threat Kits. The Mail Threat Kits are designed to mimic the look and feel of "live" explosive devices or components thereof or of other types of mail threats and to provide a substantially similar X-ray signature as actual "live" explosive devices or other types of mail threats. Embodiments of the Mail Threat Kits may be used to train personnel to identify actual mail threats.

FIG. 43 illustrates a first mail threat kit 605. The mail threat kit 605 includes a pressure activated micro switch 157 which closes a circuit between the power source 160 and the simulated blasting cap 130 inserted into an explosive simulant 120 upon a release of pressure on the switch 157, for example, by opening a box (not shown) in which the switch 157 is disposed. The simulant 120 is a simulant for dynamite. The components of the mail threat kit 605 may be similar to those of the simulated IED Circuit Kit 100 illustrated in FIG. 15.

Figure 44:
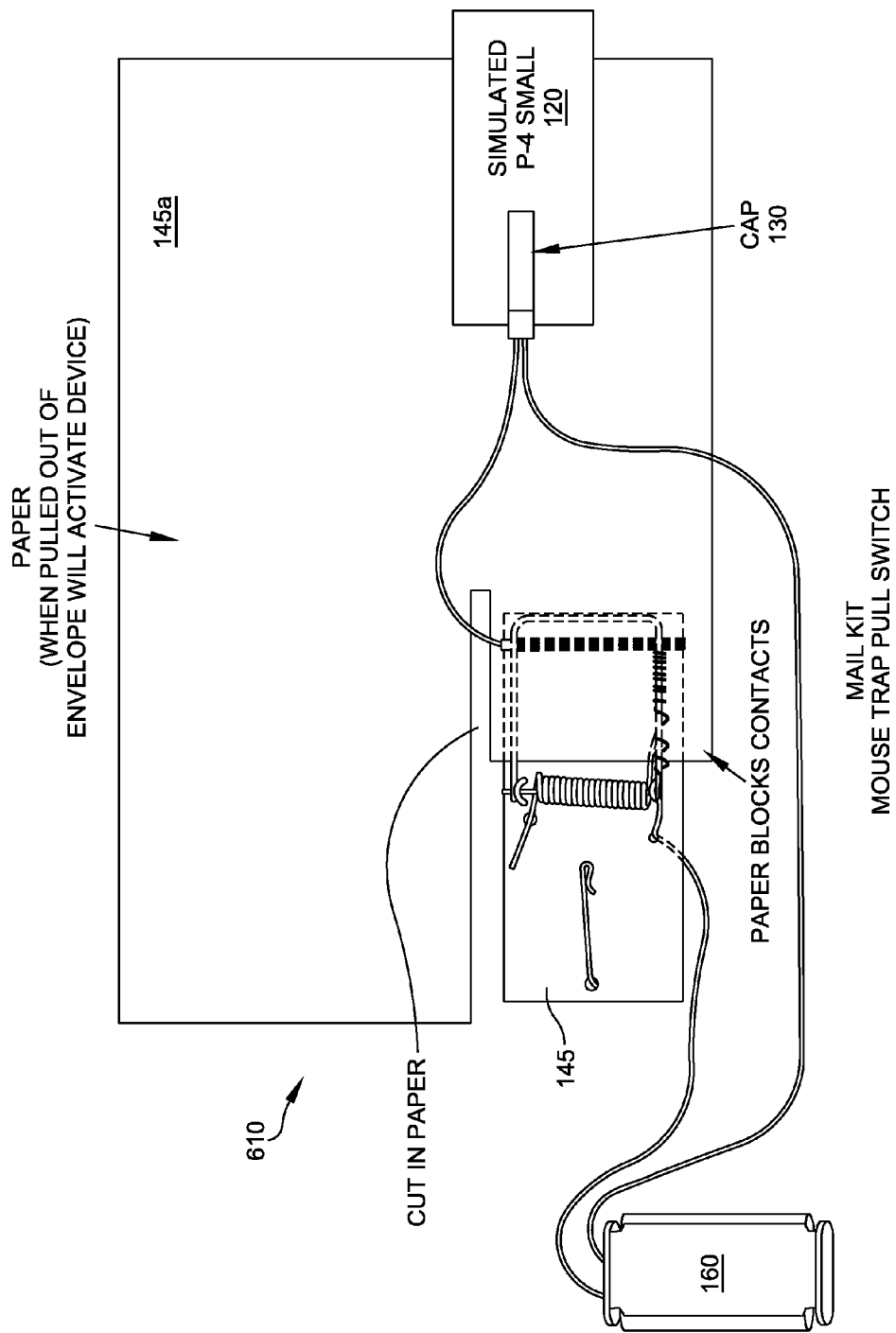
FIG. 44 illustrates an embodiment of a Mail Threat Kit.

FIG. 44 illustrates another mail threat kit 610. The mail threat kit 610 includes a mousetrap 145. Electrical connection is made from the power source 160 to the spring of the mousetrap and to a base of the mousetrap 145. The circuit between the power source 160 and a simulated blasting cap 130 inserted into an explosive simulant 120 is completed when a non-conductive material 145a, for example a piece of paper or plastic is pulled from under the spring of the mousetrap 145. The mail threat kit 610 may be disposed within a large envelope and the material 145a may be positioned such that a person opening the envelope would pull the material 145a out, thus activating the device. The components of the mail threat kit 610 may be similar to those of the simulated IED Circuit Kit 100 illustrated in FIG. 4

Figure 45:
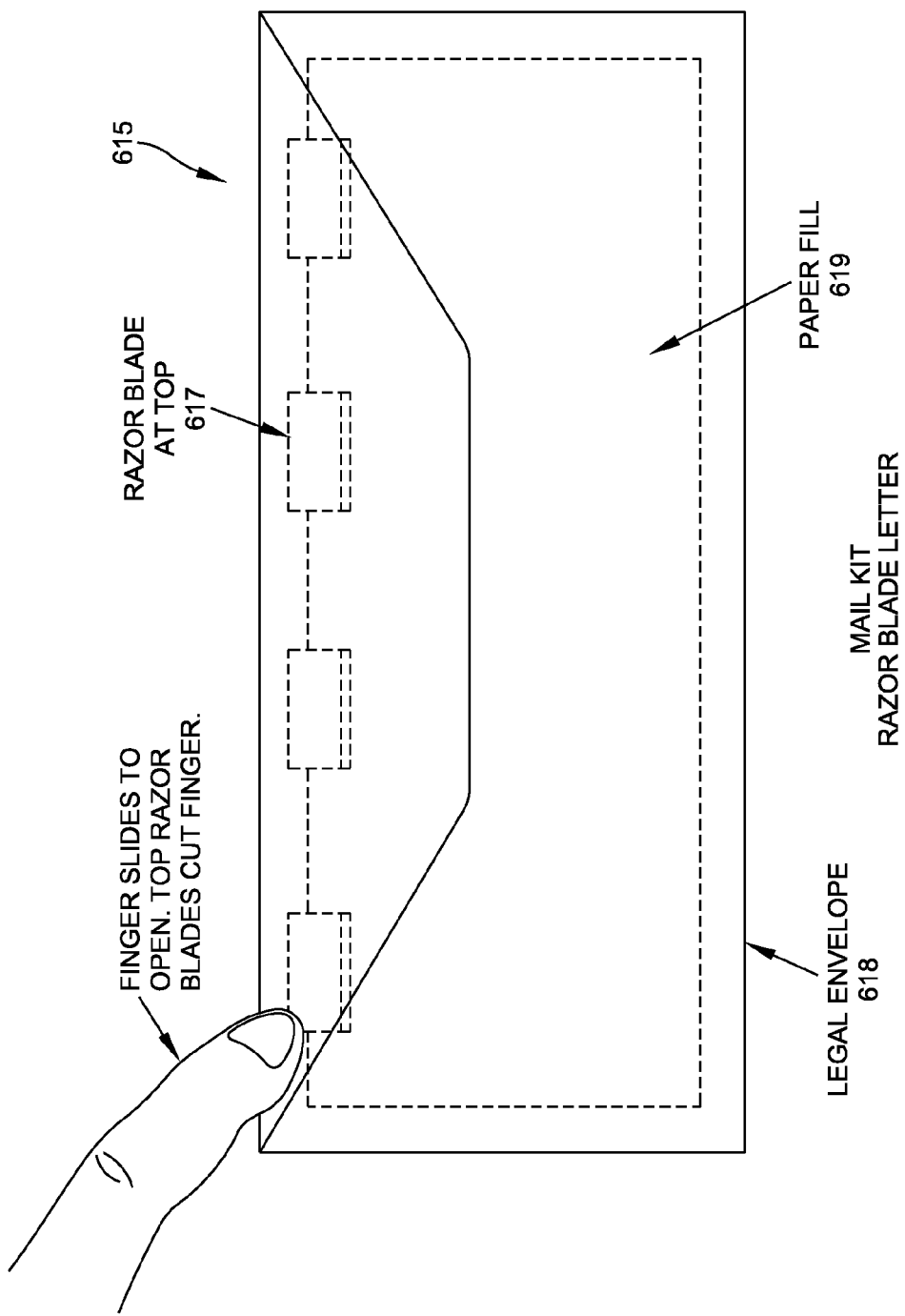
FIG. 45 illustrates an embodiment of a Mail Threat Kit.

FIG. 45 illustrates another mail threat kit 615. The mail threat kit 615 includes an envelope 618, for example, a legal sized envelope with a paper filling 619 and a plurality of razor blades 617 disposed at the top of the paper filling 619 or envelope 618. A person opening the envelope 618 could have a finger cut by the razor blades 617. In the mail threat kit 615, the razor blades 617 may be dulled to reduce the chance of someone being cut by them.

Figure 46:
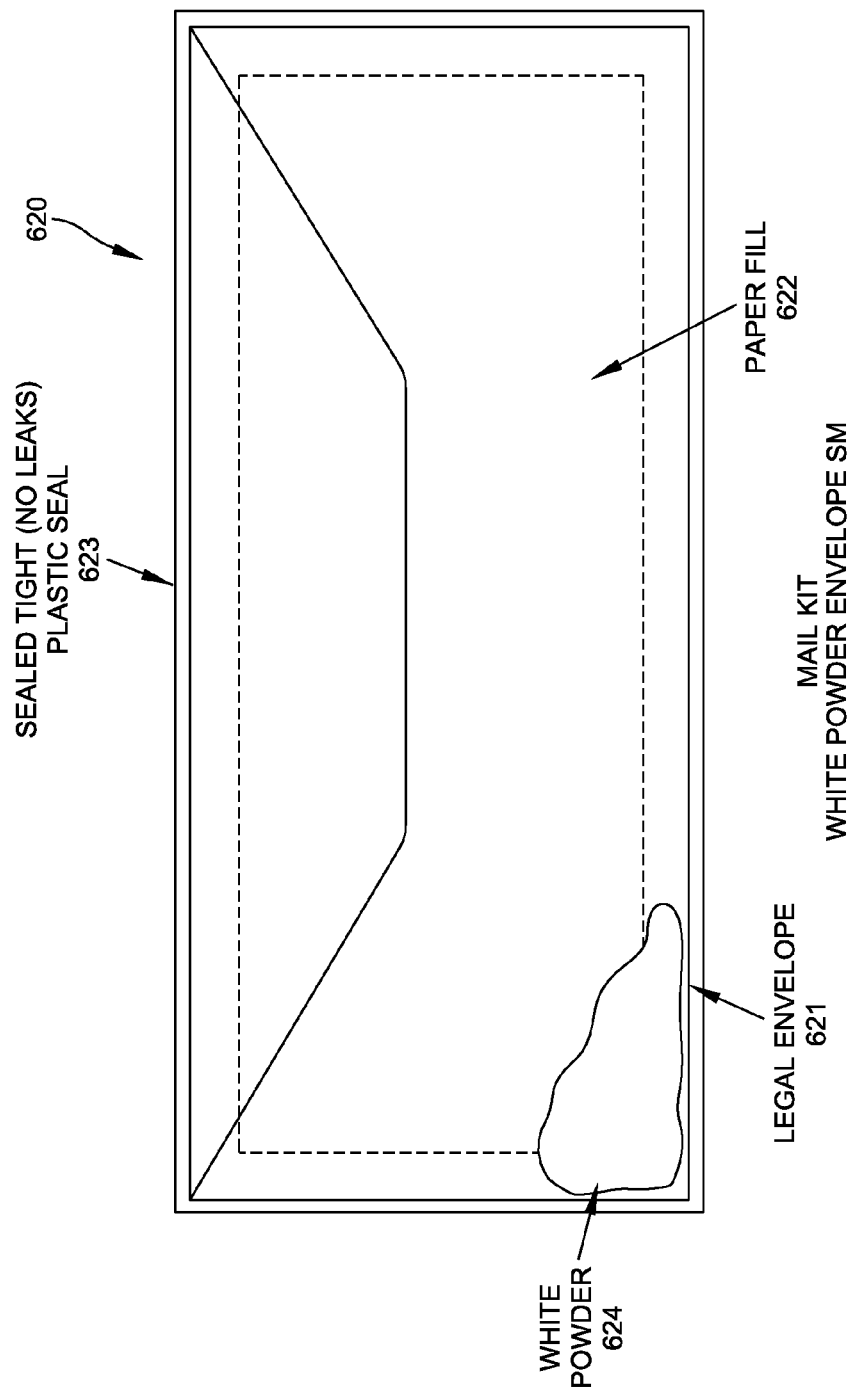
FIG. 46 illustrates an embodiment of a Mail Threat Kit.

FIG. 46 illustrates another mail threat kit 620. The mail threat kit 620 includes an envelope 621, for example, an A4 sized envelope, having a paper filling 622 and a small amount, for example, from about 0.5 ounces to about one ounce of a white powder 624, for example, flour or baby powder enclosed inside the envelope 621. The white powder 624 may simulate a powdered poison, for example, anthrax. The envelope 621 may be provided sealed in a plastic bag 623. The plastic bag 623 is, in actual situations in which a possible mail biological threat is found, a procedural step where the possible mail biological threat is bagged to prevent any further spread of the possible biological threat.

Figure 47:
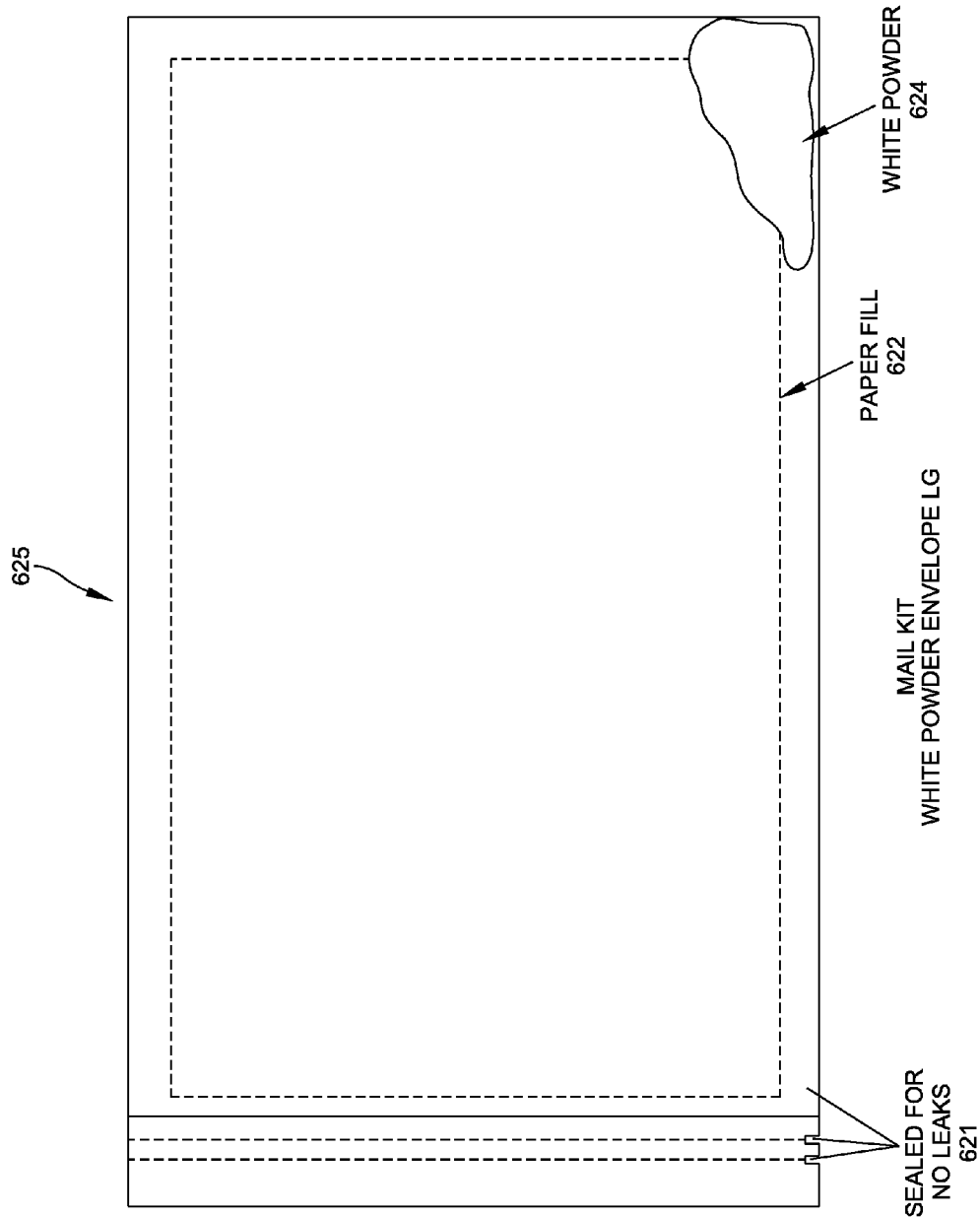
FIG. 47 illustrates an embodiment of a Mail Threat Kit.

FIG. 47 illustrates another mail threat kit 625. Mail threat kit 625 is substantially the same as mail threat kit 620, but the envelope 621 is a larger legal sized or padded envelope.

Figure 48:
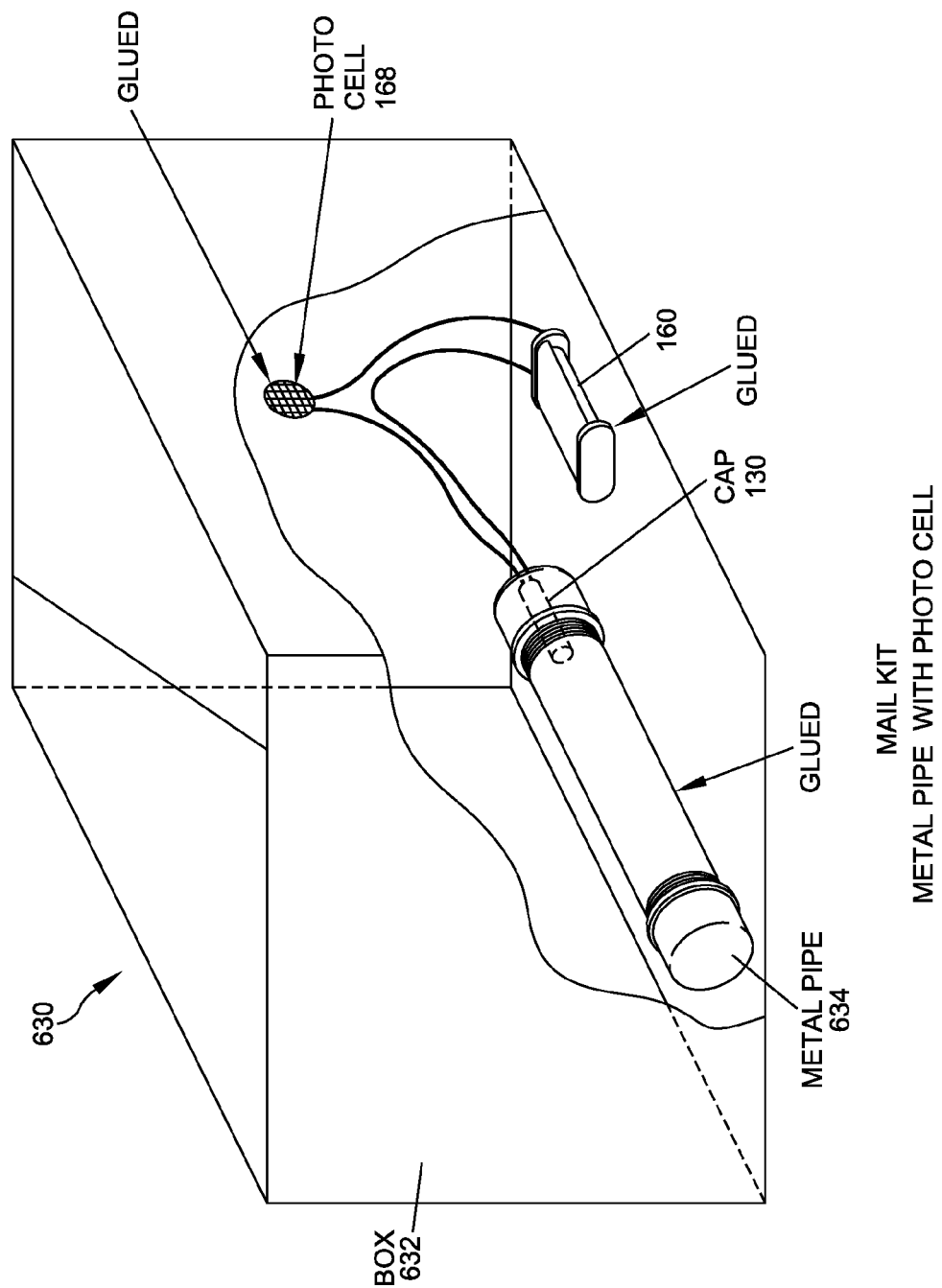
FIG. 48 illustrates an embodiment of a Mail Threat Kit.

FIG. 48 illustrates another mail threat kit 630. The mail threat kit 630 includes a shipping box 632 in which is mounted a metal pipe 634 which may be filled with an explosive simulant to simulate a pipe bomb and may include a simulated blasting cap 130 inserted into one end. The simulated blasting cap 130 may be coupled to a power source 160 through a photo cell 168. Opening the box 632 allows light to reach the photo cell 168 and close the circuit between the power source 160 and the simulated pipe bomb 634. The metal pipe 634, photocell 168, and power source 160 may be secured to internal sides of the box 632 with tape or an adhesive such as a glue to prevent these components from moving within the box 632.

FIGS. 49A and 49B illustrate another mail threat kit 635. The mail threat kit 635 is created by modifying a conventional musical greeting card 635a. A simulated sheet explosive 639, for example, charcoal in a plastic bag, and simulated blasting cap 130 are inserted into the musical greeting card 635a and wires 638 which power the speaker 637 of the conventional musical greeting card 635a from a battery 160 on a circuit board 636 are diverted from the speaker 637 to the blasting cap 130. Upon opening the modified musical greeting card, power is supplied from the battery 160 to the simulated blasting cap 130.

FIG. 50 illustrates another mail threat kit 640. The mail threat kit 640 includes a power source 160 electrically coupled to a simulated blasting cap 130 inserted into an explosive simulant 120, for example, a C-4 explosive simulant through a wire loop switch 169 similar to that illustrated in FIG. 26. The C-4 explosive simulant 120 may be packaged in a plastic bag. These components are disposed within a large padded envelope 621. One of the wires 169a of the wire loop switch is secured to the envelope 621, for example, with tape or an adhesive. A second wire 169b of the wire loop switch 169 is secured to a piece of paper 622 within the envelope 621, for example, with tape or an adhesive. Removal of the paper 622 from the envelope 621 causes the wires 169a, 169b to come into contact, completing an electrical circuit between the power source 160 and the simulated blasting cap 130.

FIG. 51 illustrates another mail threat kit 645. The mail threat kit 645 includes a mailing tube 646 in which is mounted a PVC pipe 637 which may be filled with an explosive simulant to simulate a pipe bomb and may include a simulated blasting cap 130 inserted into one end. The simulated blasting cap 130 may be coupled to a power source 160 through a wire loop switch 169. Removing the lid 649 of the mailing tube 646 pulls a string or cable 648 secured to one of the wires of the wire loop switch 169 causing the wires of the wire loop switch 169 to come into contact and close the circuit between the power source 160 and the simulated blasting cap 130. The PVC pipe 637, wire loop switch 169, and power source 160 may be secured to internal sides of the mailing tube 646 with tape or an adhesive such as a glue to prevent these components from moving within the mailing tube 646.

FIG. 52A illustrates another mail threat kit 650 and FIG. 52B illustrates another mail threat kit 650a. The mail threat kits 650, 650a each include a simulated blasting cap 130 which is coupled to a simulated detonating cord (det. cord) explosive 652 and to a power source 160 through a wire loop switch 169 in a box 651. Upon opening the box 651, the wire loop switch 169 may be caused to close by any one or more of the mechanisms discussed with regard to other embodiments herein, completing a circuit between the power source 160 and the simulating blasting cap 130. Mail threat kit 650a differs from mail threat kit 650 in that mail kit 650a includes a lead sheet 654 which may render X-ray imaging of the mail threat kit 650a more difficult.

FIG. 53 illustrates another mail threat kit 655. The mail threat kit 655 includes a mailing box 657 in which is mounted a pair of bottles 658 which may contain simulated components of a liquid binary explosive. A simulated blasting cap 130 is placed proximate the bottles 658 and coupled to a power source 160 through a micro switch 157. Upon opening the box 657, the micro switch 157 would close, completing a circuit between the power source 160 and the simulated blasting cap 130. The bottles 658, micro switch 157, and power source 160 may be secured to internal sides of the mailing box 657 with tape or an adhesive such as a glue to prevent these components from moving within the mailing box 657.

FIG. 54 illustrates another mail threat kit 660. The mail threat kit 660 includes a power source 160 electrically coupled to a simulated blasting cap 130 inserted into an explosive simulant 120 in a mailing box 657. A wire 661 from the power source is electrically connected to a first layer of aluminum foil wrap 662 wrapped about the mailing box 657. A wire 663 from the simulated blasting cap 130 is electrically connected to a second layer of aluminum foil wrap 664 wrapped about the mailing box 657 and separated from the first layer of aluminum foil wrap 662 by a layer of paper 665. A second layer of paper 665 may cover the second layer of aluminum foil wrap 664. Upon ripping the paper 665 and aluminum foil wrapping 662, 664 about the mailing box 657, the first layer of aluminum foil wrap 662 contacts the second layer of aluminum foil wrap 664, completing a circuit between the power source 160 and the simulated blasting cap 130.

In addition to any of the Threat Screening Kits or mail threat kits described above, threat kits may include any one or more of the combinations of packages, explosive simulant quantities, firing circuit types, power source types, and/or detonator types listed in Table 2 below:

TABLE 2

| Assembly Name | Device Container and/or Concealment | Explosive Simulant | Simulant Weight Range (kg) | Firing Circuit | Power Source | Detonator |
|---|---|---|---|---|---|---|
| Laptop IED | Laptop | Sheet | 0.1-0.5 | Internal | Laptop Batteries | Improvised Copper Blasting Cap |
| Laptop IED | Laptop | HMTD | 0.1-0.5 | Digital Timer | Laptop Batteries | Cardboard TATP Blasting Cap |
| Stuffed Animal | Stuffed animal | Detonation Cord | 0.1-0.5 | Non-Electrical | N/A | Non-Electrical Blasting Cap |
| Tablet IED | Tablet | Sheet | 0.1-0.5 | Victim activated | 2 AA | Military Blasting Cap |
| Childs Toy IED | Childs Toy | ANFO | 0.5-1.0 | Victim activated pressure switch | 2 AA | Military Blasting Cap with Slide-on Booster |
| RCIED | Cell Phone | Sheet | 0.1-0.5 | Cell Phone RCIED | Internal | Improvised Copper Blasting Cap |
| RCIED | Cell Phone | PETN | 0.1-0.5 | Cell Phone RCIED | External | Commercial Blasting Cap |
| Hair Dryer IED | Hair Dryer | Cast TNT | 0.5-1.0 | Victim activated toggle twitch | 2 AA | Military Blasting Cap |
| Home DVD Player IED | Home DVD Player | ANFO | 0.1-0.5 | Cell Phone RCIED | 9 V | Military Blasting Cap with Slide-on Booster |
| Baby Wipe Tub IED | Baby Wipe Tub | HMTD | 0.5-1.0 | Wireless Door Bell | 4 AA | Improvised Copper Blasting Cap |
| Can Opener IED | Can Opener | C-4 | 0.5-1.0 | Victim activated pressure switch | 1 C | Commercial Blasting Cap |
| Boom Box IED | Boom Box | C-4 | 1.0-2.0 | Barometric Pressure Switch | 2 AA | Commercial Blasting Cap |
| Computer Bag | Computer bag | PE-4 | 1.0-2.0 | Light-Sensitive Photocell | 9 V | Commercial Blasting Cap |
| Drill IED | Drill | HMTD | 0.5-1.0 | Pressure Switch | 4 AAA | Improvised Copper Blasting Cap |
| Large Suit Case IED | Large Suitcase | Semtex H | 1.0-2.0 | Micro switch (Pressure Release) | Lantern Battery | Commercial Blasting Cap |
| Small Suit Case IED | Small Suitcase | ANAL | 1.0-2.0 | RCIED Cell Phone Trigger Assembly | 2 D Cell | Commercial Blasting Cap |
| Duffle Bag IED | Duffle Bag | Semtex H | 1.0-2.0 | RCIED Radio | 9 V | Military Blasting Cap |
| Water Hose IED | Water Hose | PETN | 1.0-2.0 | Tilt Switch | 1 AAA | Military Blasting Cap |
| Tennis Shoe IED | Tennis Shoe | Semtex 10 | 0.1-0.5 | Suicide switch Assembly | 9 V | Improvised Copper Blasting Cap |
| Hiking Shoe IED | Hiking Shoe | PETN/RDX | 0.1-0.5 | Time Fuse | N/A | Non-Electrical Blasting Cap |
| Sandal Shoe IED | Shoe Sandal | Sheet | 0.1-0.5 | Time Fuse | Non-Electrical | Non-Electrical Blasting Cap |
| Belt IED | Belt | Sheet | 0.1-0.5 | Suicide switch Assembly | 2 AAA | Military Blasting Cap |
| Cordless Vacuum IED | Cordless Hand Vacuum | PE-4 | 1.0-2.0 | Victim activated | Internal | Improvised Copper Blasting Cap |
| Knee Brace IED | Knee Brace | Semtex H | 0.1-0.5 | Suicide switch Assembly | 2 AAA | Military Blasting Cap |
| Hand Brace IED | Hand Brace | HMTD | 0.1-0.5 | Suicide switch Assembly | 9 V | Improvised Copper Blasting Cap |

TABLE 2-continued

| Assembly Name | Device Container and/or Concealment | Explosive Simulant | Simulant Weight Range (kg) | Firing Circuit | Power Source | Detonator |
|---|---|---|---|---|---|---|
| Leg Brace IED | Leg Brace | TATP | 0.1-0.5 | Suicide switch Assembly with back up RCIED | 4 AA | Cardboard TATP Blasting Cap |
| Hard Case IED | Hard case | Extra Gelatin Dynamite (8) | 1.0-2.0 | Digital Timer | 9 V | Commercial Blasting Cap |
| Printer Cartridge IED | Printer Cartridge | PETN | 1.0-2.0 | RCIED Cell Phone Trigger Assembly | 9 V | Improvised Copper Blasting Cap |
| Portable CD Player IED | CD Player | C-4 | 0.1-0.5 | Victim activated | 2 AA | Commercial Blasting Cap |
| Electric Screwdriver IED | Electric Screwdriver | PETN | 0.1-0.5 | Victim activated | Internal | Cardboard TATP Blasting Cap |
| Radio IED | Radio | C-4 | 0.5-1.0 | Victim activated | 2 C | Improvised Copper Blasting Cap |
| Circular Saw IED | Circular saw | Ammonium Dynamite | 0.5-1.0 | Victim activated | 2 C | Improvised Copper Blasting Cap |
| Walking Cane IED | Walking Cane | PETN | 0.5-1.0 | Victim activated | 1 AA | Military Blasting Cap |
| Walker IED | Walker | PE-7 | 1.0-2.0 | Suicide switch in handle | 9 V | Commercial Blasting Cap |
| Baseball Hat IED | Baseball Hat | Sheet | 0.1-0.5 | Victim activated | 1 AAA | Improvised Copper Blasting Cap |
| Picnic Cooler IED | Picnic Cooler | Semtex H | 1.0-2.0 | PIR Motion Sensor | 4 AA | Military Blasting Cap |
| Jacket IED | Jacket | Sheet | 1.0-2.0 | Suicide switch in sleeve | 4 AA | Improvised Blasting Cap |
| Jacket IED | Jacket | TATP | 1.0-2.0 | Suicide switch in pocket | 2 D | Commercial Blasting Cap |
| Thermos IED | Thermos | Flake TNT | 0.5-1.0 | Improvised Vibration Switch | 2 AA | Cardboard TATP Blasting Cap |
| Briefcase IED | Briefcase | Semtex 10 | 1.0-2.0 | LRCT | 4 AA | Commercial Blasting Cap |
| Paperback Book IED | Book Paperback | TNT Cast Booster | 1.0-2.0 | Micro switch (Pressure Release) | 9 V | Military Blasting Cap |
| Hardcover Book IED | Book Hard Cover/Metal Pipe | Black Powder | 0.1-0.5 | Clothespin Pull Switch | 4 AA | Electric Match/Squib |
| Computer Power Cord IED | Computer Power Cord | TATP | 0.1-0.5 | Victim activated | External | Military Blasting Cap |
| Tire Air Pump IED | Tire air pump | ANFO | 0.5-1.0 | RCIED Cell Phone Trigger Assembly | 9 V | Military Blasting Cap with slide-on booster |
| Disposable Camera IED | Disposable Camera | TATP | 0.1-0.5 | digital timer | 2 AA | Cardboard TATP Blasting Cap |
| Digital Camera IED | Camera digital | PE-4 | 0.1-0.5 | Time Fuse | N/A | Non-Electrical Blasting Cap |
| Coffee Mug IED | Coffee Mug | HMTD | 0.5-1.0 | Light-Sensitive Photocell | 9 V | Military Blasting Cap |
| Neck Pillow IED | Neck Pillow | C-4 | 0.5-1.0 | Digital Timer | 2 AA | Commercial Blasting Cap |
| Bottle of Wine IED | Bottle of wine | Nitromethane (PLX) | 1.0-2.0 | Time Fuse | N/A | Non-Electrical Blasting Cap |

TABLE 2-continued

| Assembly Name | Device Container and/or Concealment | Explosive Simulant | Simulant Weight Range (kg) | Firing Circuit | Power Source | Detonator |
|---|---|---|---|---|---|---|
| Back Pack/Pressure Cooker IED | Back Pack/Pressure Cooker | ANFO | 1.0-2.0 | RCIED Cell Phone Trigger Assembly | 4 AA | Electric Match/Squib |
| Back pack/2 Metal Pipes IED | Back pack/2 Metal Pipes | Black Powder | 1.0-2.0 | Mechanical Time Delay II | 2 D | Electric Match/Squib |
| Shower Bag IED | Shower bag | HMTD | 0.5-1.0 | Wire-Loop Switch | 2 C | Cardboard TATP Blasting Cap |
| Flashlight IED | Flashlight | Extra Gelatin Dynamite Mixture | 0.5-1.0 | Victim activated | 2 AAA | Improvised Copper Blasting Cap |
| Contact Lens Cleaner IED | Contact Lens cleaner | Nitromethane (PLX) | 0.5-1.0 | Digital Timer | 9 V | Improvised Copper Blasting Cap |
| Micro-switch Pressure Release IED | Mail Box/Package | Ammonium Nitrate/Nitro-Glycerin | 0.5-1.0 | Micro switch (Pressure Release) | 9 V | Commercial Blasting Cap |
| Mouse-Trap Pull Switch IED | Mail Box/Package | PE-4 | 0.5-1.0 | Mouse Trap Pull Switch | 4 AA | Military Blasting Cap |
| Metal-Pipe IED with Photocell | Mail Box/Package | Black Powder | 0.5-1.0 | Metal-Pipe IED with Photocell | 2 D | Electric Match/Squib |
| Wire-Loop Switch IED | Mail Box/Package | Sheet | 0.1-0.5 | Wire-Loop Switch | 4 AA | Military Blasting Cap |
| Clothespin Pull Switch IED | Mail Box/Package | Black Powder | 0.5-1.0 | Clothespin Pull Switch | 2 C | Electric Match/Squib |
| Wire Loop with Lead Sheet IED | Mail Box/Package | Det Cord | 0.5-1.0 | Wire Loop with Lead Sheet | 9 V | Military Blasting Cap |
| Chemical IED | Mail Box/Package | Bleach/Ammonia | 0.5-1.0 | Chemical IED | 2 D | Improvised Copper Blasting Cap |
| Anti-Probe IED | Mail Box/Package | M112 C-4 | 0.5-1.0 | Anti-Probe | 2 D | Improvised Copper Blasting Cap |
| Barometric Pressure Switch IED | Mail Box/Package | Semtex H | 0.5-1.0 | Barometric Pressure Switch | 9 V | Military Blasting Cap |
| Small Tool Box | Small Tool Box | PE-7 | 1.0-2.0 | Magnetic Reed Switch | Lantern Battery | Commercial Blasting Cap |
| Tooth Paste Tube IED | Tooth paste tube | PETN | 0.1-0.5 | External | External | External |
| Women's Purse IED | Women's purse | Extra Gelatin Dynamite (4) | 1.0-2.0 | RCIED radio | 9 V | Commercial Blasting Cap |
| Iron IED | Iron | Ammonium Dynamite | 0.5-1.0 | Victim activated toggle switch | 9 V | Cardboard TATP Blasting Cap |
| Toy Car IED | Toy car | TATP | 0.5-1.0 | Servo Switch | Internal | Cardboard TATP Blasting Cap |
| Legal Binder IED | Legal binder | Detonation Cord | 0.1-0.5 | Digital Timer | 2 D | Military Blasting Cap |
| Laundry detergent Box/PVC pipe IED | Laundry detergent box/PVC pipe | Smokeless Powder | 1.0-2.0 | Ball-Tilt Switch | 2 AA | Electric Match/Squib |
| Lotion IED | Lotion large | Nitromethane (PLX) | 0.5-1.0 | Ball-Tilt Switch | 2 AA | Commercial Blasting Cap |
| Small Cooler IED | Small Cooler | Semtex H | 1.0-2.0 | PIR Motion Sensor | 4 AA | Cardboard TATP Blasting Cap |
| Foot Powder Bottle IED | Foot Powder Bottle | Emulsion | 0.1-0.5 | Vibration Sensor Assembly | 2 AA | Commercial Blasting Cap |
| Hair Gel IED | Hair Gel | Emulsion | 0.1-0.5 | Anti Lift Micro switch (Presure Release) | 1 AA | Improvised Blasting Cap |

TABLE 2-continued

| Assembly Name | Device Container and/or Concealment | Explosive Simulant | Simulant Weight Range (kg) | Firing Circuit | Power Source | Detonator |
|---|---|---|---|---|---|---|
| Can of Soda IED | Can of soda | ANAL | 0.1-0.5 | Non-Electrical Time Fuse | N/A | Improvised Blasting Cap |
| Pressure Cooker IED | Pressure cooker | Smokeless Powder | 1.0-2.0 | RCIED Cell Phone Trigger Assembly | 4 AA | Electric Match/Squib |
| Lunch Box IED | Lunch Box | Semtex H | 0.5-1.0 | Mouse Trap Pull Switch | 2 AA | Military Blasting Cap |
| Vest with Frag IED | Vest frag | TATP | 1.0-2.0 | Suicide switch Assembly | 9 V | Improvised Blasting Cap |
| Vest without Frag IED | Vest no frag | Sheet | 1.0-2.0 | Suicide switch Assembly | 2 AAA | Commercial Blasting Cap |
| Limpet Device IED | Limpet device | Black Powder | 1.0-2.0 | Magnetic Reed Switch | 1 D | Electric Match/Squib |

FIGS. 55-63 illustrate various explosive simulant assemblies.

Figure 55:
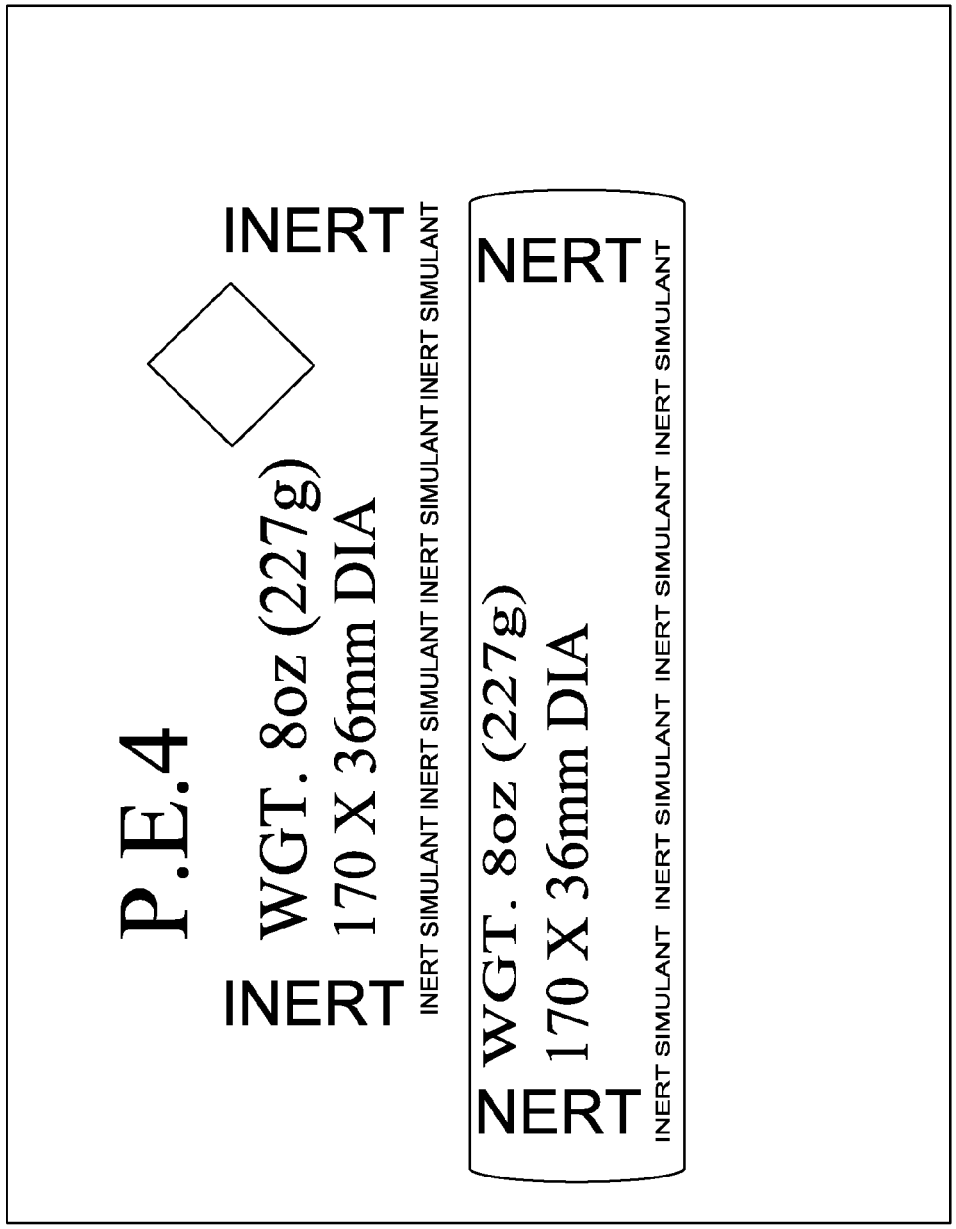
FIG. 55 illustrates an embodiment of an explosive simulant assembly.

FIG. 55 illustrates an inert PE-4 long assembly. This assembly includes simulant mix 9 packed within an 8 inch× 1.25 inch plastic tube sealed with end caps including cap wells. The tube is wrapped in white card stock paper with a wax coating.

Figure 56B:
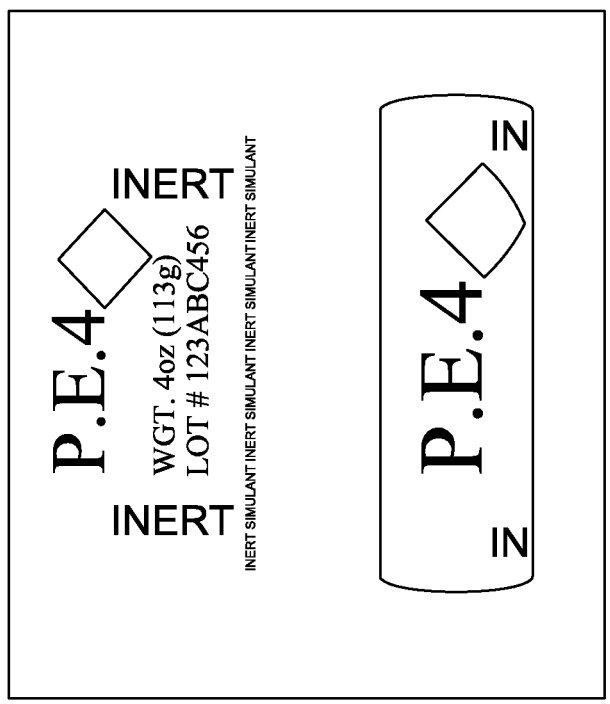
FIG. 56B illustrates an embodiment of an explosive simulant assembly.
Figure 56A:
FIG. 56A illustrates an embodiment of an explosive simulant assembly.

FIGS. 56A and 56B illustrate an inert PE-4 short assembly. This assembly includes simulant mix 9 packed within 5 inch× 1.5 inch mailing tube sealed with end caps including cap wells. The tube is wrapped in white card stock paper with a wax coating.

Figure 57:
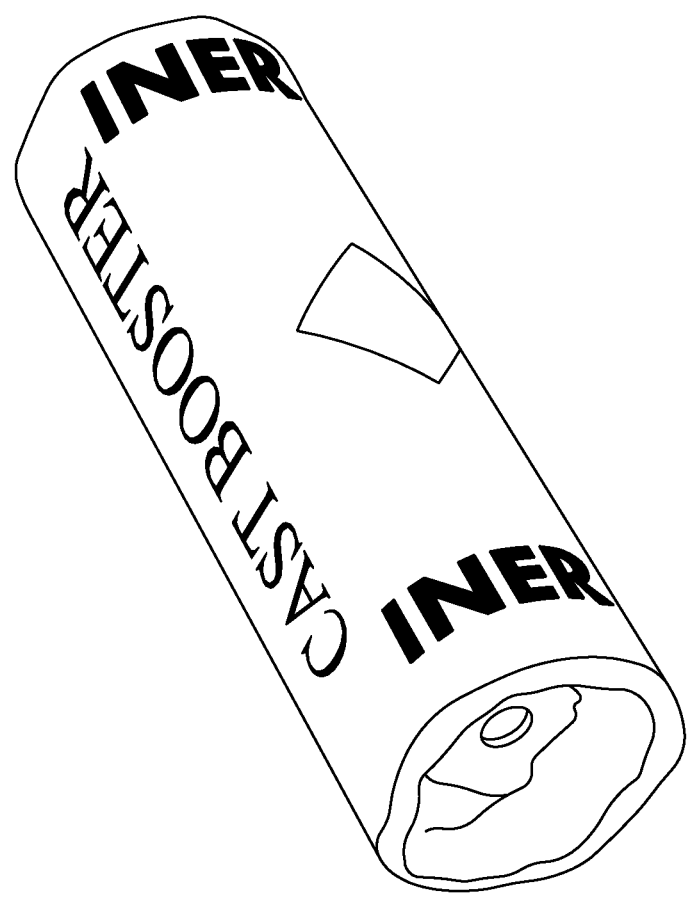
FIG. 57 illustrates an embodiment of an explosive simulant assembly.

FIG. 57 illustrates an inert TNT cast booster assembly. This assembly includes simulant mix 9 packed within 5 inch×1.5 inch mailing tube sealed with end caps. The tube is wrapped in red card stock paper with a mod podge coating. The ends of the assembly are drilled with 0.25 inch×1 inch holes on each end.

Figure 58:
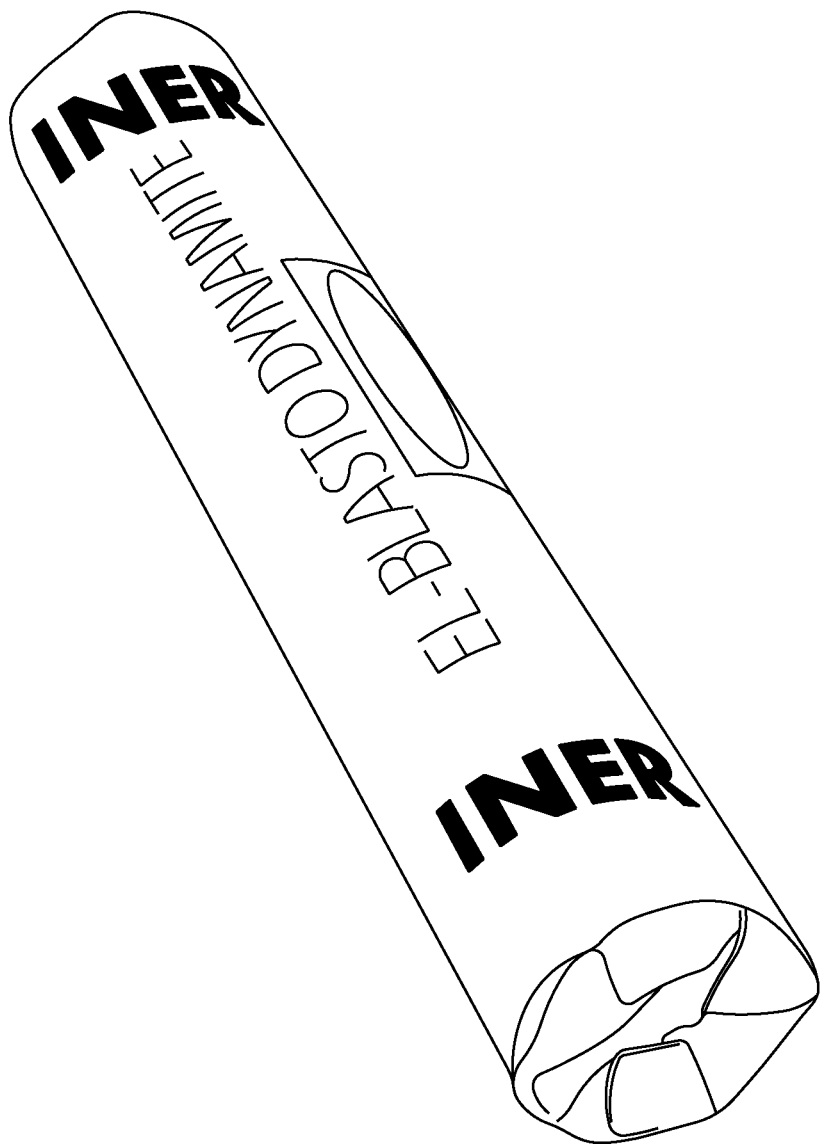
FIG. 58 illustrates an embodiment of an explosive simulant assembly.

FIG. 58 illustrates an inert El Blasto Dynamite assembly. This assembly includes simulant mix 1 packed within an 8 inch×1.25 inch plastic tube sealed with end caps including cap wells. The tube is wrapped in brown card stock paper with a wax coating.

Figure 59A:
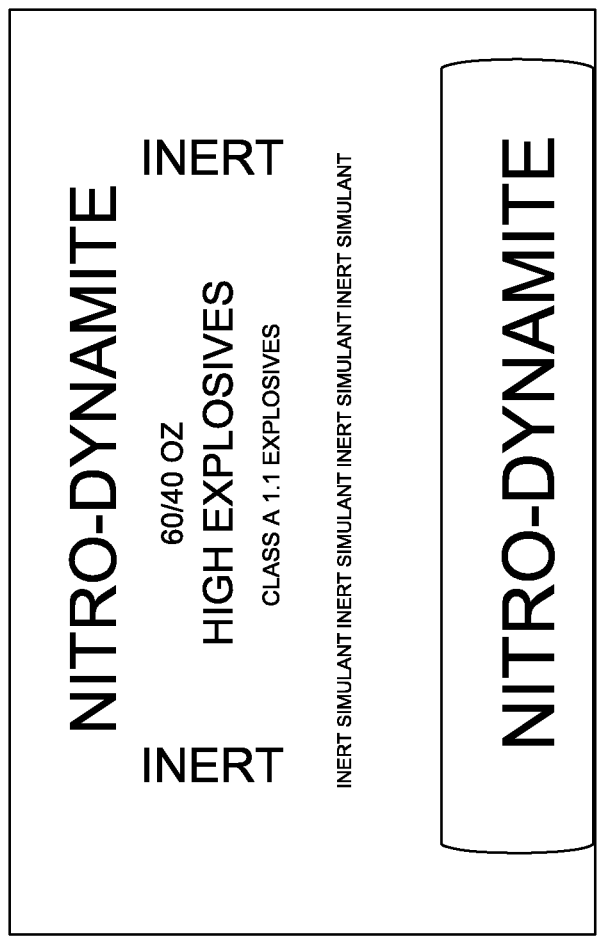
FIG. 59A illustrates an embodiment of an explosive simulant assembly.
Figure 59B:
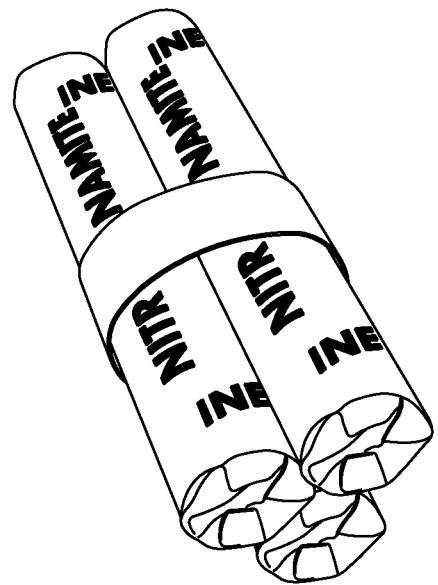
FIG. 59B illustrates an embodiment of an explosive simulant assembly.

FIGS. 59A and 59B illustrate an inert nitro dynamite assembly. This assembly includes simulant mix 1B packed within an 8 inch×1.25 inch plastic tube sealed with end caps including cap wells. The tube is wrapped in red card stock paper with a wax coating.

Figure 60B:
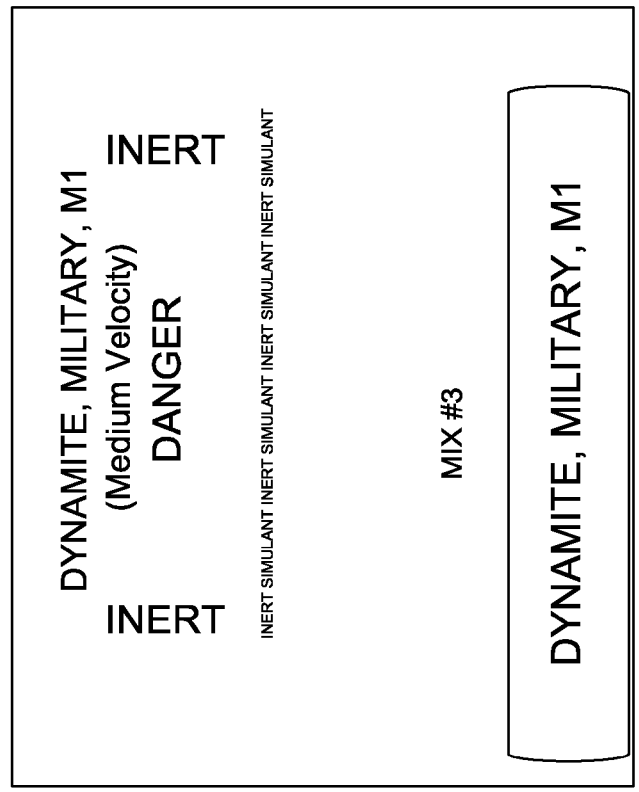
FIG. 60B illustrates an embodiment of an explosive simulant assembly.
Figure 60A:
FIG. 60A illustrates an embodiment of an explosive simulant assembly.

FIGS. 60A and 60B illustrate an inert military M1 dynamite assembly. This assembly includes simulant mix 3 packed within an 8 inch×1.25 inch plastic tube sealed with end caps including cap wells. The tube is wrapped in brown card stock paper with a wax coating.

Figure 61:
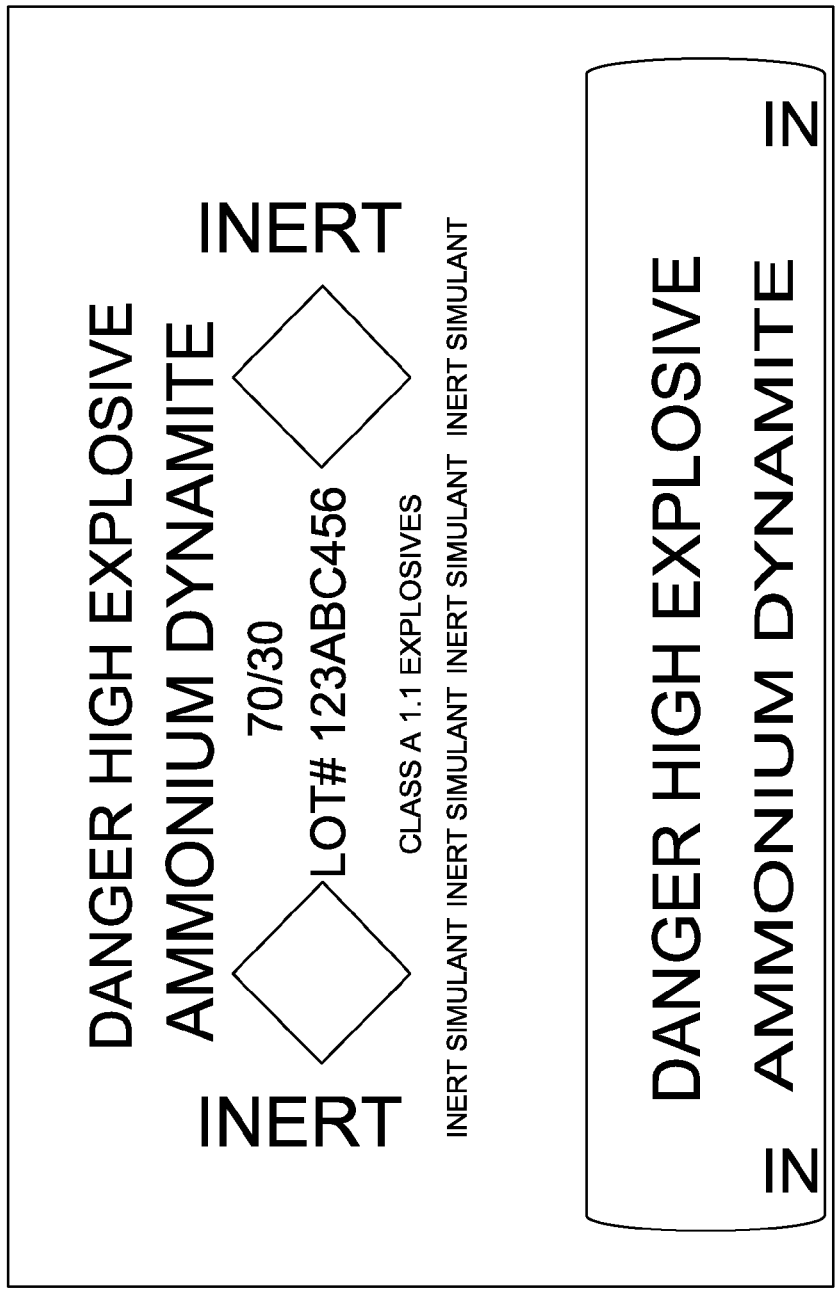
FIG. 61 illustrates an embodiment of an explosive simulant assembly.

FIG. 61 illustrates an inert ammonium dynamite assembly. This assembly includes simulant mix 1A packed within an 8 inch×1.25 inch plastic tube sealed with end caps including cap wells. The tube is wrapped in yellow stock paper with a wax coating.

Figure 62:
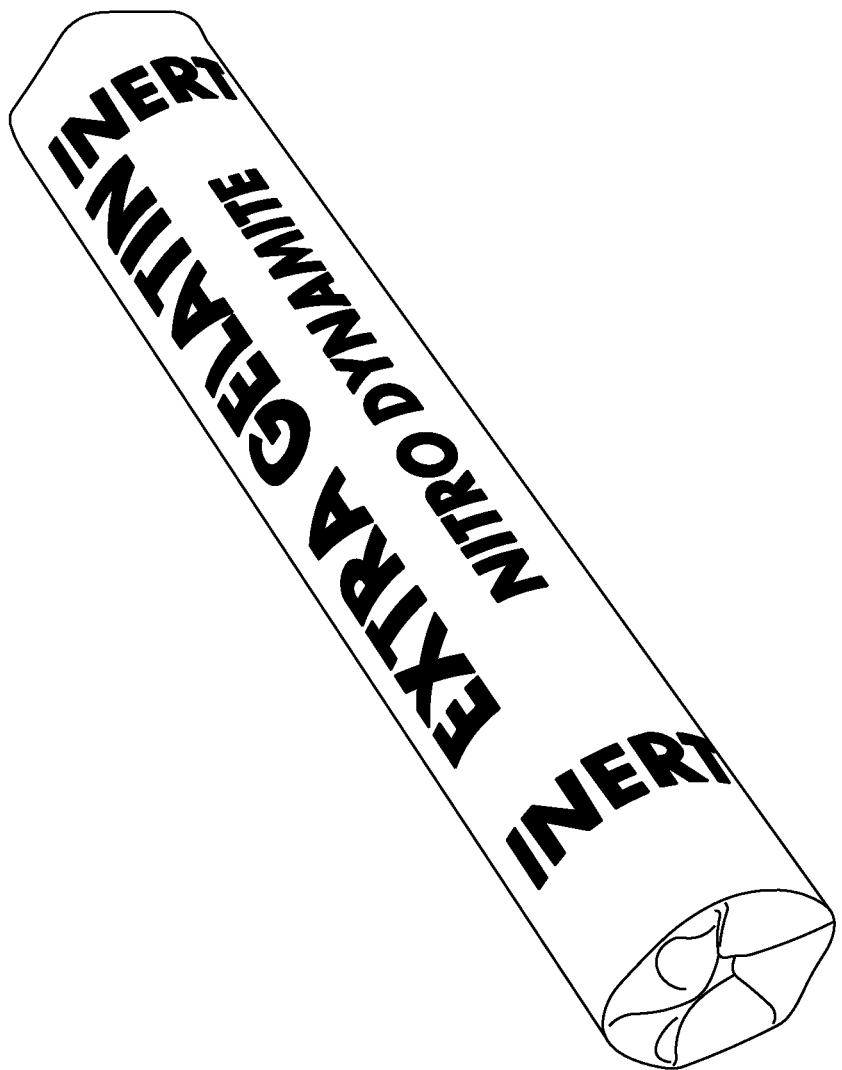
FIG. 62 illustrates an embodiment of an explosive simulant assembly.

FIG. 62 illustrates an extra gelatin dynamite assembly. This assembly includes simulant mix 2 packed within an 8 inch× 1.25 inch plastic tube sealed with end caps including cap wells. The tube is wrapped in brown stock paper with a wax coating.

Figure 63:
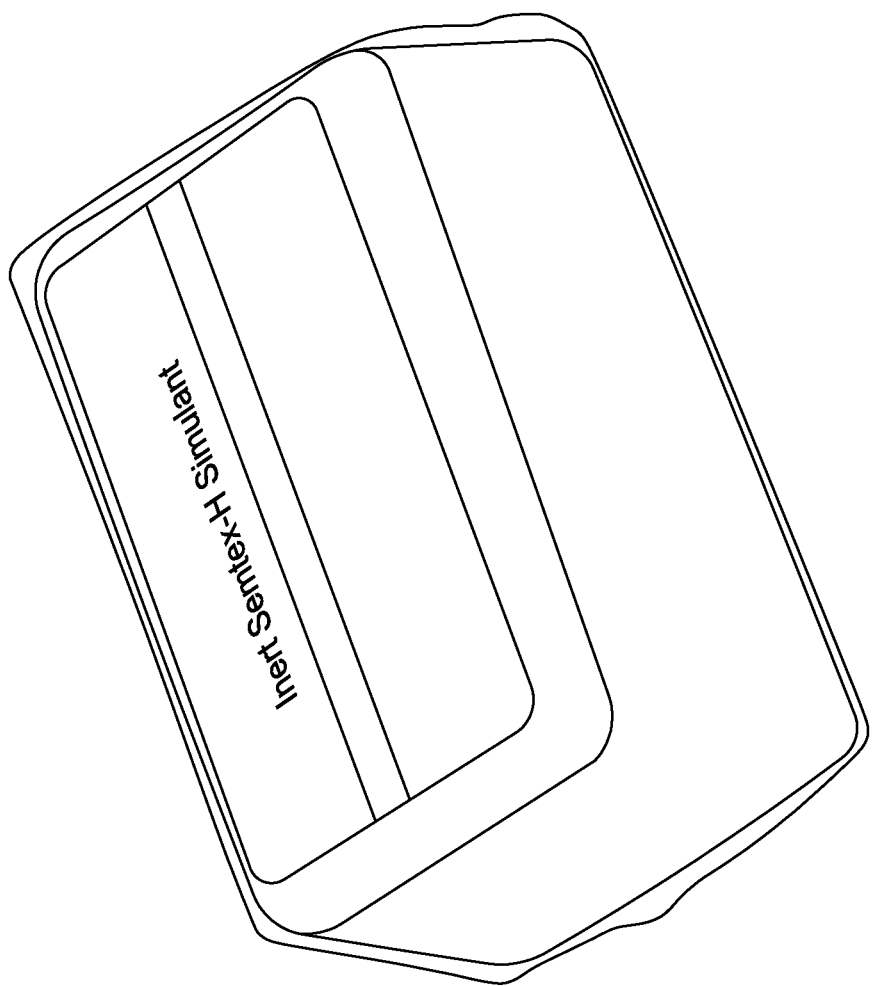
FIG. 63 illustrates an embodiment of an explosive simulant assembly.

FIG. 63 illustrates an inert Semtex assembly. The assembly includes simulant mix 5 and an orange, red, and/or black pigment molded in a baking pan form vacuum sealed and labeled.

Having thus described several aspects of at least one embodiment of this invention, it is to be appreciated various alterations, modifications, and improvements will readily occur to those skilled in the art. For example, it is to be appreciated that any of the features of any of the embodiments disclosed herein may be combined or substituted for features of any other embodiment disclosed herein. Such alterations, modifications, and improvements are intended to be part of this disclosure, and are intended to be within the scope of the invention. Accordingly, the foregoing description and drawings are by way of example only.

What is claimed is:

1. A simulated explosive material consisting essentially of three or more inert components and having a density substantially similar to an explosive material, the density of the simulated explosive material being within a range of from about 0.8 grams per cubic centimeter (g/cm$^3$) to about 4.7 g/cm$^3$, the simulated explosive material configured to produce an output signal consistent with the presence of the explosive material when scanned in an X-ray scanner, the three or more inert components including one or more of sugar, baking soda, corn starch, or calcium chloride.

2. The simulated explosive material of claim 1, wherein the three or more inert components include a mixture of brown sugar and one or more of corn syrup, baking soda, water, or vegetable oil.

3. The simulated explosive material of claim 2, having a density of between about 1.0 g/cm$^3$ and about 1.5 g/cm$^3$ and configured to produce an output signal consistent with the presence of dynamite when scanned in an X-ray scanner.

4. The simulated explosive material of claim 1, wherein the three or more inert components include a confectioner sugar and one or more of corn starch or corn syrup.

5. The simulated explosive material of claim 4, having a density of between about 1.4 g/cm$^3$ and about 1.5 g/cm$^3$ and configured to produce an output signal consistent with the presence of one of dynamite or PE-4 when scanned in an X-ray scanner.

6. The simulated explosive material of claim 1, wherein the three or more inert components include baking soda and one or more of corn syrup, corn starch, water, oil, or paraffin wax.

7. The simulated explosive material of claim 6, having a density of between about 1.2 g/cm and about 1.5 g/cm$^3$ and configured to produce an output signal consistent with the presence of one of TNT or a plastic explosive when scanned in an X-ray scanner.

8. The simulated explosive material of claim 1, wherein the three or more inert components include paraffin wax, corn starch, water, and oil.

9. The simulated explosive material of claim 8, configured to produce an output signal consistent with the presence of one of PE-4, TNT, or nitroglycerine when scanned in an X-ray scanner.

10. The simulated explosive material of claim 1, including a mixture of 900 parts dark brown sugar, 100 parts corn syrup, and 150 parts baking soda.

11. The simulated explosive material of claim 1, including a mixture of water, charcoal, sodium chloride, and calcium chloride in a ratio of 200 ml of water to 200 g of charcoal to 65 g of sodium chloride to 35 g of calcium chloride.

12. The simulated explosive material of claim 1, including a mixture of 200 parts glycerin, 200 parts corn starch, 80 parts hydrogen peroxide, and one of 120 parts alumina, 130 parts alumina, 140 parts alumina, or 190 parts alumina.

13. The simulated explosive material of claim 1, including a mixture of baking soda, water, vegetable oil, and paraffin wax in a ratio of 1340 g baking soda to 15 g water to 218 g vegetable oil to 907 g paraffin wax.

14. The simulated explosive material of claim 1, including a mixture of baking soda, corn starch, water, and vegetable oil in a ratio of 595 g baking soda to 150 g corn starch or 300 g cornstarch to 237 g water or 355 g water to 14 g vegetable oil or 109 g vegetable oil.

15. The simulated explosive material of claim 1, including a mixture of polyethylene powder, cane sugar, glycerin, and powder detergent in a ratio of 800 g polyethylene powder to 400 g cane sugar to 110 g glycerin to 200 g powder detergent.

16. The simulated explosive material of claim 1, including a mixture of polyethylene powder, baking soda, glycerin, and powder detergent in a ratio of one of 600 g polyethylene powder to 250 g baking soda to 81 g glycerin to 150 g powder detergent, 200 g polyethylene powder to 50 g baking soda to 60 g glycerin to 575 g powder detergent, or 50 g polyethylene powder to 150 g baking soda to 60 g glycerin to 700 g powder detergent.

17. The simulated explosive material of claim 1, including a mixture of 75% water, 20% cane sugar, and 5% sodium chloride.

18. The simulated explosive material of claim 1, including a mixture of 62% water, 31% cane sugar, 4% sodium chloride, and 2% corn syrup.

19. A simulated explosive material comprising two or more inert components and having a density substantially similar to a plastic explosive, the density of the simulated explosive material being within a range of from about 1.3 grams per cubic centimeter (g/cm$^3$) to about 1.72 g/cm$^3$, the simulated explosive material configured to produce an output signal consistent with the presence of the plastic explosive when scanned in an X-ray scanner, the two or more inert components selected from among the components of one of the groups consisting of:
  baking soda and corn starch;
  baking soda and paraffin wax;
  sugar and corn syrup;
  corn starch, baking soda, and glycerin; or
  alumina and hydrogen peroxide.

20. The simulated explosive material of claim 19, including a mixture of 900 parts dark brown sugar and one of 50 parts corn syrup or 100 parts corn syrup.

21. The simulated explosive material of claim 19, including a mixture of confectioner sugar and corn syrup in a ratio of 907 g of confectioner sugar to 233 g corn syrup or 250 g confectioner sugar to 155 g corn syrup.

22. The simulated explosive material of claim 19, including a mixture of baking soda and paraffin wax in a ratio of 893 g baking soda to 907 g paraffin wax.

23. The simulated explosive material of claim 19, including a mixture of glycerine, corn starch, alumina, and hydrogen peroxide, having a density of about 1.4 g/cm$^3$, and configured to produce an output signal consistent with the presence of Semtex when scanned in an X-ray scanner.

24. The simulated explosive material of claim 23, further comprising water, vegetable oil, and corn starch.

25. The simulated explosive material of claim 19, including a mixture of glycerine, corn starch, alumina, and hydrogen peroxide, having a density of about 1.6 g/cm$^3$, and configured to produce an output signal consistent with the presence of C4 when scanned in an X-ray scanner.

26. The simulated explosive material of claim 19, including a mixture of baking soda and paraffin wax, having a density of about 1.5 g/cm$^3$, and configured to produce an output signal consistent with the presence of PE 4 when scanned in an X-ray scanner.

27. The simulated explosive material of claim 19, including a mixture of baking soda, corn starch, water, and vegetable oil and having a density of about 1.5 g/cm$^3$.

28. The simulated explosive material of claim 19, including a mixture of corn starch, magnesium citrate, baking soda, water, and vegetable oil and having a density of about 1.2 g/cm$^3$.

29. The simulated explosive material of claim 19, including a mixture of polyethylene powder, sugar, glycerine, powdered detergent, and baking soda, and configured to produce an output signal consistent with the presence of PETN when scanned in an X-ray scanner.

30. The simulated explosive material of claim 19, closely matching the look and feel of the plastic explosive.

* * * * *

UNITED STATES PATENT AND TRADEMARK OFFICE
CERTIFICATE OF CORRECTION

| | | |
|---|---|---|
| PATENT NO. | : 9,291,436 B2 | |
| APPLICATION NO. | : 14/334997 | |
| DATED | : March 22, 2016 | |
| INVENTOR(S) | : Abiy Eshetu et al. | |

It is certified that error appears in the above-identified patent and that said Letters Patent is hereby corrected as shown below:

In the Claims:

Column 30, claim 7, line number 64, delete "1.2 g/cm" and insert -- 1.2 g/cm$^3$ --.

Signed and Sealed this
Seventh Day of June, 2016

Michelle K. Lee
*Director of the United States Patent and Trademark Office*